(12) United States Patent
Otake et al.

(10) Patent No.: US 7,732,456 B2
(45) Date of Patent: Jun. 8, 2010

(54) PYRIDONE DERIVATIVE

(75) Inventors: Norikazu Otake, Tsukuba (JP); Yuji Haga, Tsukuba (JP); Akira Naya, Tsukuba (JP); Sayaka Mizutani, Tsuchiura (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 931 days.

(21) Appl. No.: 10/591,373

(22) PCT Filed: Mar. 4, 2005

(86) PCT No.: PCT/JP2005/004260

§ 371 (c)(1),
(2), (4) Date: Aug. 31, 2006

(87) PCT Pub. No.: WO2005/085200

PCT Pub. Date: Sep. 15, 2005

(65) Prior Publication Data

US 2007/0208046 A1    Sep. 6, 2007

(30) Foreign Application Priority Data

Mar. 5, 2004   (JP) ............................. 2004-062005

(51) Int. Cl.
*A61K 31/444*   (2006.01)
*C07D 401/02*   (2006.01)

(52) U.S. Cl. ...................... 514/269; 514/332; 514/345; 544/314; 546/261; 546/301

(58) Field of Classification Search .................. None
See application file for complete search history.

(56) References Cited

U.S. PATENT DOCUMENTS

| 6,930,185 B2 | 8/2005 | Ishihara et al. |
| 2004/0077628 A1 | 4/2004 | Ishihara et al. |
| 2005/0176795 A1 | 8/2005 | Schwink et al. |

FOREIGN PATENT DOCUMENTS

| EP | 1 283 199 | 2/2003 |
| WO | WO 01/21577 | 3/2001 |
| WO | WO 02/02744 | 1/2002 |
| WO | WO 02/06245 | 1/2002 |
| WO | WO 02/094799 | 11/2002 |
| WO | WO 03/045912 | 6/2003 |
| WO | WO 03/068230 | 8/2003 |

OTHER PUBLICATIONS

Dyke et al., Exp. Opin. Ther. Patents, vol. 15 (2005), pp. 1303-1313, "Recent developments in the discovery of MCH-1R antagonists for the treatment of obesity—an update".

*Primary Examiner*—Zinna N Davis
(74) *Attorney, Agent, or Firm*—Janet E. Fair; John C. Todaro

(57) ABSTRACT

The invention provides pyridone derivatives represented by a general formula (I)

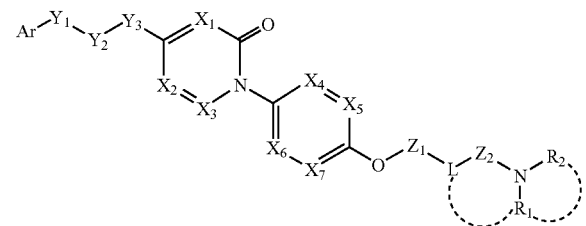

[in the formula, $R_1$ and $R_2$ may be same or different and stands for H, etc., or $R_1$ and $R_2$ may form an aliphatic nitrogen-containing heterocyclic group together with the N to which they bind; $X_1$-$X_3$ may be same or different and stand for methine or N, provided not all of them simultaneously stand for nitrogen; $X_4$-$X_7$ may be same or different and stand for methine or N, provided that three or more of them do not simultaneously stand for N; $Y_1$ and $Y_3$ may be same or different and stand for single bond, —O—, —NR—, —S—, etc; $Y_2$ stands for lower lkylene, etc.; R stands for H, etc., L stands for methylene; $Z_1$ and $Z_2$ may be same or different and stand for single bond or lower alkylene; or $R_1$, L and $Z_2$ may form an aliphatic nitrogen-containing heterocyclic group with the N to which $R_1$ binds; and Ar stands for aromatic carbocyclic group, etc.].

23 Claims, No Drawings

PYRIDONE DERIVATIVE

CROSS-REFERENCE TO RELATED APPLICATIONS

This application is a U.S. National Phase application under 35 U.S.C. §371 of PCT Application No. PCT/JP2005/004260, filed Mar. 4, 2005, which claims priority under 35 U.S.C. §365(b) from Japanese patent application No. JP2004-62005, filed Mar. 5, 2004.

TECHNICAL FIELD

This invention relates to novel pyridone derivatives. The derivatives act as antagonists to melanin concentrating hormone receptor, and are useful as preventing or treating agents of various diseases of cardiovascular system, nervous system, metabolic systems, reproductive system, respiratory system, digestive system and the like.

BACKGROUND OF THE INVENTION

Melanin concentrating hormone (hereafter abbreviated as "MCH") is a cyclic peptide hormone/neuro-peptide, which was for the first time isolated by Kawauchi, et al. in 1983 from sermon hypophysis [cf: Nature, Vol. 305, 321 (1983)]. The hormone is known to functionally antagonize to melanin cell stimulating hormone in fishes, to cause concentration of melanin granules in melanophore and participate in body color change [cf: International Review of Cytology, Vol. 126, 1(1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [cf. The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being accumulated. That is, it has been reported that expression of mRNA, which is a MCH precursor, was accelerated in brains of ob/ob mouse, db/db mouse, $A^y$/a mouse, Zucker fatty rat or the like which are model animals of hereditary obesity, or in brains of fasted mice [cf. Nature, Vol. 380, 243 (1996); Diabetes, Vol. 47,294(1998); Biochemical and Biophysical Research Communications, Vol. 268, 88 (2000); Molecular Brain Research, Vol. 92, 43 (2001)].

Acute ventricular administration of MCH to rats was observed to induce accelerated feeding activity [cf. Nature, Vol. 380,243 (1996)] and chronic administration invites obesity accompanied by polyphagy [cf. Proceedings of the National Academy of Science of the United States of America, Vol. 99, 3240, (2002)]. Moreover, MCH precursor gene-deficient mouse shows reduced food ingestion or rise in oxygen consumption per body weight compared to wild type mice. Its low body weight due to decrease in body fat was observed [cf. Nature, Vol. 396, 670 (1998)].

On the contrary, transgenic mouse which expresses excessive MCH precursor develops obesity accompanied by polyphagy and insulin resistance [cf. The Journal of Clinical Investigation, Vol. 107, 379 (2001)]. Consequently, it is suggested that MCH is an important factor for developing obesity and participates in diseases induced by metabolic disorder or respiratory diseases of which one of risk factors is obesity. Besides, MCH is known to participate also in anxiety-using action, epilepsy, memory, learning, diuretic action, excretory action of sodium and potassium, oxytocin secreting action, reproduction and reproductive function [cf. Peptides, Vol. 17, 171 (1996); Peptides, Vol. 18, 1095 (1997), Peptides, Vol, 15, 757 (1994); Journal of Neuroendocrinology, Vol. 8, 57 (1996); Critical Reviews in Neurobiology, Vol. 8, 221, (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [cf. Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Physical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); and Molecular Pharmacology, Vol. 60, 632 (2001)].

Of those, the pharmacological action observed on rodents is induced mainly via MCH-1R [cf. Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, deficiency of MCH-1R promotes activity amount of mouse [Proceedings of the National Academy of Sciences of the United States of America, Vol. 99, 3240 (2002)], and its participation in central diseases accompanied by behavioral disorder, for example, attention-deficit hyperactivity disorder, schizophrenia, depression and the like also is strongly suggested [cf. Molecular Medicine Today, Vol. 6, 43 (2000); Trends in Neuroscience, Vol. 24, 527 (2001)].

It is also reported that autoantibody to MCH-1R is present in serum of vitiligo vulgaris patient [cf. The Journal of Clinical Investigation, Vol. 109, 923 (2002)]. Furthermore, expression of MCH-1R in certain species of cancer cells was reported, and in vivo expression sites of MCH and MCH-1R also suggest MCH's participation in cancer, sleep, vigil, drug dependence and digestive disorders [cf. Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon its binding to MCH receptors. Therefore, when its binding to MCH receptor is inhibited, expression of MCH action can be inhibited. In consequence, substances which are antagonists to binding of MCH with its receptor are useful as preventing or treating agent of those various diseases in which MCH participates, for example, metabolic disorders represented by obesity, diabetes, hormone disorder, hyperlipidemia, gout, fatty liver, and the like; cardiovascular disorders, represented by stenocardia, acute or congestive heart failure, myocardial infarction, coronary atherosclerosis, hypertension, renal diseases and electrolyte abnormality, central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

PCT International Publications WO 01/21577, WO 01/82925, WO 02/06245 and WO 02/02744 Pamphlets disclosed compounds having MCH receptor antagonism, but none of the disclosed compounds contains pyridone ring.

On the other hand, PCT International Publication WO 03/68232 Pamphlet disclosed a certain kind of pyridone derivatives exhibiting P38MAP kinase activity, but it contained no disclosure about MCH receptor antagonism of the compounds.

DISCLOSURE OF THE INVENTION

We engaged in concentrative studies on compounds which have MCH receptor antagonism, and now discovered that such pyridone derivatives in which a 6-membered ring selected from benzene, pyridine ring and pyrimidine ring binds to N-atom on the pyridone ring, and an oxygen-containing substituent group binds to the 6-membered ring at para-position to the pyridone ring, via the oxygen, possess MCH receptor antagonistic activity and are effective for prevention, treatment and therapy of those various diseases which are associated with MCH receptors. The present invention is whereupon completed.

Thus, the present invention provides pyridone derivatives represented by a general formula (I)

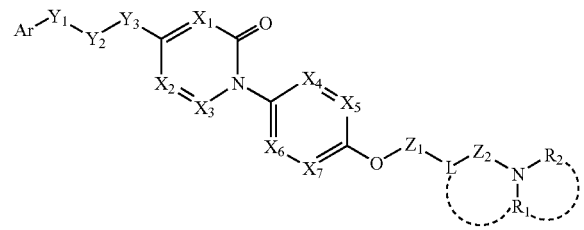

(1)

[in the formula, $R_1$ and $R_2$ may be same or different and each stands for hydrogen, optionally substituted lower alkyl, optionally substituted lower cycloalkyl, optionally substituted lower alkylcarbonyl, optionally substituted lower alkyloxycarbonyl or optionally substituted lower alkylsulfonyl; or $R_1$ and $R_2$ may form an optionally substituted aliphatic nitrogen-containing heterocyclic group together with the nitrogen atom to which they bind;

$X_1$, $X_2$ and $X_3$ may be the same or different, each standing for optionally substituted methine or nitrogen atom, provided not all of $X_1$, $X_2$ and $X_3$ simultaneously stand for nitrogen, $X_4$, $X_5$, $X_6$ and $X_7$ may be same or different and each stands for optionally substituted methine or nitrogen, provided that three or more of $X_4$, $X_5$, $X_6$ and $X_7$ do not simultaneously stand for nitrogen;

$Y_1$ stands for a single bond, —O—, —NR—, —S—, —SO— or —$SO_2$—, $Y_2$ stands for optionally substituted lower alkylene, optionally substituted lower alkenylene or optionally substituted lower cycloalkylene;

$Y_3$ stands for a single bond, —O—, —NR—, —S—, —SO— or —$SO_2$—;

R stands for hydrogen or optionally substituted lower alkyl,

L stands for optionally substituted methylene, $Z_1$ and $Z_2$ may be same or different and each stands for a single bond or optionally substituted lower alkylene;

$R_1$, L and $Z_2$ may together form an optionally substituted aliphatic nitrogen-containing heterocyclic group with the nitrogen to which $R_1$ binds;

and

Ar stands for an optionally substituted aromatic carbocyclic group, optionally substituted heteroaromatic group or optionally substituted aliphatic carbocyclic group]

or pharmaceutically acceptable salts thereof

The invention also provides MCH receptor antagonists containing those compounds of the formula (I) as the active component, and medical compositions containing the compounds of the formula (I).

Hereinafter the present invention is explained in further details.

In the present specification, the term, "lower", signifies that any group or compound designated with this term contains no more than 6 carbons, preferably no more than 4 carbons.

"Lower alkyl" includes $C_1$-$C_6$ straight chain alkyl and $C_3$-$C_6$ branched alkyl, specific examples being methyl, ethyl, n-propyl, isopropyl, n-butyl, isobutyl, sec-butyl, tert-butyl, n-pentyl, isopentyl, neopentyl, tert-amyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

"Lower cycloalkyl" includes $C_3$-$C_6$ cycloalkyl, specific examples being cyclopropyl, cyclobutyl, cyclopentyl and cyclohexyl.

"Lower alkylene" includes $C_1$-$C_6$ straight chain alkylene and $C_3$-$C_6$ branched alkylene, specific examples being methylene, ethylene, propylene, butylene, pentylene and hexylene.

"Lower alkenylene" signifies $C_2$-$C_6$ straight chain or $C_3$-$C_6$ branched alkenylene containing one carbon-to-carbon double bond in the chain, specific examples being vinylene, 1-propenylene, 2-propenylene, 1-butenylene, 2-butenylene, 3-butenylene, 2-pentenylene, 3-pentenylene, 4pentenylene, 1-hexenylene, 2-hexenylene, 3-hexenylene, 4-hexenylene and 5-hexenylene.

"Lower cycloalkylene" includes $C_3$-$C_6$ cycloalkylene, specific examples being 1,1-cyclopropylene, 1,2-cyclopropylene, 1,1-cyclobutanylene, 1,2-cyclobutanylene, 1,3-cyclobutanylene, 1,1-cyclopentenylene, 1,2-cyclohexenylene, 1,3-cyclohexenylene and 1,4-cyclohexenylene.

As the substituents in "optionally substituted lower alkyl", "optionally substituted lower cycloalkyl", "optionally substituted lower alkylene", "optionally substituted lower alkenylene" and "optionally substituted lower cycloalkylene", for example, halogen, cyano, hydroxyl, amino, optionally fluorine- or hydroxyl-substituted lower alkyl, mono-lower alkylamino, di-lower alkylamino, optionally fluorine-substituted lower alkyloxy, lower alkyloxy lower alkyl, lower alkyloxycarbonyl, lower alkyloxycarbonylamino, lower alkyloxycarbonyl-(lower alkyl)amino, lower alkylcarbonyl, lower alkylcarbonyloxy, lower alkylcarbonylamino, lower alkylcarbonyl-(lower alkyl)amino, carbamoyl, mono-lower alkylcarbamoyl, di-lower alkylcarbamoyl, carbamoylamino, mono-lower alkylcarbamoylamino, di-lower alkylcarbamoylamino, mono-lower alkylcarbamoyl-(lower alkyl)amino, di-lower alkylcarbamoyl-(lower alkyl) amino, carbamoyloxy, mono-lower alkylcarbamoyloxy, di-lower alkylcarbamoyloxy, lower alkylsulfonyl, lower alkylsulfonylamino, lower alkylsulfonyl-(lower alkyl)amino, sulfamoyl, mono-lower alkylsulfamoyl, di-lower alkylsulfamoyl, sulfamonylamino, mono-lower alkylsulfamonylamino, di-lower alkylsulfamoylamino, mono-lower alkylsulfamoyl-(lower alkyl)amino and di-lower alkylsulfamoyl-(lower alkyl)amino can be named. Of these groups, lower alkyl and the like groups can contain one or more substituents.

"Aliphatic nitrogen-containing heterocyclic group" includes 3- to 7-membered monocyclic or 5- to 12-membered polycyclic, saturated or partially unsaturated heterocyclic groups containing as a part of the ring-forming members at least one, preferably 1-3, nitrogen atoms and optionally 0-2 oxygen atoms or 0-2 sulfur atoms, specific examples being aziridinyl, azetidinyl, pyrrolidinyl, piperidinyl, homopiperazinyl, homopiperidinyl, morpholinyl, thiomorpholinyl, octahydrocyclopenta [b]-pyrrolyl, hexahydropyrrolidinyl, octahydroindolizinyl, octahydroquinolizinyl, octahydropyrido[2.1-C]-oxazinyl and 2,5,6,7-tetrahydro-5H-pyrrolo[1.2-a]imidazolyl.

"Aromatic carbocyclic group" includes $C_6$-$C_{14}$, preferably $C_6$-$C_{10}$, monocyclic or polycyclic aromatic carbocyclic groups, specific examples being phenyl, naphthyl and phenanthryl.

"Heteroaromatic group" includes 5- to 6-membered monocyclic or 8- to 14-membered polycyclic heteroaromatic groups containing as a part of the ring-constituting members at least one, preferably 1-5, heteroatoms selected from nitrogen, oxygen and sulfur atoms, specific examples being pyridinyl, pyrimidinyl, pyridazinyl, pyrazyl, pyrazolyl, pyrrolyl, imidazolyl, triazolyl, oxazolyl, isoxazolyl, oxadiazolyl, thiazolyl, isothiazolyl, thiaziazolyl, tetrazolyl, pyridazinyl, pyrazinyl, furyl, thienyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthaladinyl, naphthyridinyl, quinoxalinyl, quinazolinyl, cinnolynyl, pteridinyl and pyrido[3,2-b]pyridyl.

"Aliphatic carbocyclic group" includes $C_3$-$C_{10}$, preferably $C_3$-$C_8$ monocyclic or polycyclic, saturated or partially unsaturated carbocyclic groups, specific examples including cyclopropyl, cyclobutenyl, cyclopentyl, cyclohexyl, cycloheptyl, cyclooctyl, cyclononyl, cyclodecyl, bicyclohexyl and adamantyl.

As the substituents which may be in the "optionally substituted aliphatic nitrogen-containing heterocyclic group", "optionally substituted aromatic carbocyclic group", "optionally substituted heteroaromatic group" and "optionally substituted aliphatic carbocyclic group", oxo, lower cycloalkyl and the like can be named in addition to those named in the foregoing as possible substituents in said "optionally substituted lower alkyl". These cyclic groups can be substituted with one or more of these substituent(s).

As the substituent in the "optionally substituted methine", for example, halogen, optionally halogen-substituted lower alkyl and optionally halogen-substituted lower alkyloxy can be named.

As the substituent in the "optionally substituted lower alkyl", the definition of R, for example, halogen, lower alkoxy and lower haloalkoxy are suitable.

In the foregoing definitions, "halogen" includes fluorine, chlorine, bromine and iodine atoms.

"Oxo" signifies such a group (=O) which forms carbonyl group (C=O) together with a carbon atom in an organic compound.

"Optionally fluorine- or hydroxyl-substituted lower alkyl" includes lower alkyl and lower alkyl whose part or all of hydrogen atoms are substituted with fluorine atoms or hydroxyl groups, examples of the latter fluorine- or hydroxyl-substituted lower alkyl being fluoromethyl, difluoromethyl, trifluoromethyl, 2-fluoroethyl, 1,2-difluoroethyl, 2-hydroxyethyl and 1,2-dihydroxyethyl.

"Optionally fluorine-substituted lower alkyloxy" includes those groups in which lower alkyl or fluorine-substituted lower alkyl binds to oxygen, specific examples being: as lower alkyloxy, methoxy, ethoxy, n-propyloxy, isopropyloxy, n-butoxy, isobutoxy, tert-butoxy and n-pentyloxy, and as fluorine-substituted lower alkyloxy, fluoromethoxy, difluoromethoxy, trifluoromethoxy and 1,2-difluoroethoxy.

"Mono-lower alkylamino" is an amino (—$NH_2$) in which one of its hydrogen atoms is substituted with lower alkyl, specific examples being methylamino, ethylamino, n-propylamino, isopropylamino, n-butylamino, sec-butylamino and tert-butylamino.

"Di-lower alkylamino" is an amino (—$NH_2$) whose two hydrogen atoms are substituted with lower alkyl groups, specific examples being dimethylamino, diethylamino, ethylmethylamino, di(n-propyl)amino, methyl(n-propyl)amino and diisopropylamino.

"Lower alkyloxy-lower alkyl" signifies lower alkyloxy-substituted lower alkyl, specific examples including methoxymethyl, ethoxymethyl, n-propyloxymethyl, isopropyloxymethyl, 1-methoxyethyl and 2-methoxyethyl.

"Lower alkyloxycarbonyl" is a carbonyl (—CO—) to which lower alkyloxy is bound, which includes $C_1$-$C_6$alkyloxycarbonyl, specific examples being methoxycarbonyl, ethoxycarbonyl, n-propyloxycarbonyl, isopropyloxycarbonyl, n-butoxycarbonyl, isobutoxycarbonyl, tert-butoxycarbonyl and n-pentyloxycarbonyl.

"Lower alkyloxycarbonylamino" is an amino (—$NH_2$) to which lower alkyloxycarbonyl is bound, which includes $C_1$-$C_6$alkyloxycarbonylamino, specific examples being methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino and n-pentyloxycarbonylamino.

"Lower alkyloxycarbonyl (lower alkyl)amino" is a mono-lower alkylamino whose hydrogen on the nitrogen atom is substituted with a lower alkyloxycarbonyl. As specific examples, methoxycarbonyl(methyl)amino, ethoxycarbonyl (methyl)amino and n-propyloxycarbonyl(methyl)amino can be named.

"Lower alkylcarbonyl" is a carbonyl (—CO—) to which lower alkyl is bound, which includes $C_1$-$C_6$ alkylcarbonyl, specific examples being acetyl, propionyl, butyryl, isobutyryl, valeryl, isovaleryl and pivaloyl.

"Lower alkylcarbonyloxy" is a group in which a lower alkylcarbonyl is bound to oxygen, specific examples including acetoxy, propionyloxy, valeryloxy, isovaleryloxy and pivaloyloxy.

"Lower alkylcarbonylamino" is an amino (—$NH_2$) one of whose hydrogen atoms is substituted with lower alkylcarbonyl, specific examples being acetamido, propionylamino, isobutyrylamino, valerylamino, isovalerylamino and pivaloylamino.

"Lower alkylcarbonyl(lower alkyl)amino" is a mono-lower alkylamino in which the hydrogen on its nitrogen atom is substituted with lower alkylcarbonyl, examples of which including methylcarbonyl(methyl)amino, ethylcarbonyl(methyl)amino and n-propylcarbonyl(methyl)amino.

"Mono-lower alkylcarbamoyl" is a carbamoyl (—$CONH_2$) one of whose hydrogen atoms is substituted with lower alkyl, specific examples including methylcarbamoyl, ethylcarbamoyl, n-propylcarbamoyl, isopropylcarbamoyl, n-butylcarbamoyl, sec-butylcarbamoyl and tert-butylcarbamoyl.

"Di-lower alkylcarbamoyl" is a carbamoyl ($-CONH_2$) whose two hydrogen atoms are substituted with lower alkyl groups, specific examples including dimethylcarbamoyl, diethylcarbamoyl, ethylmethylcarbamoyl, di(n-propyl)carbamoyl, methyl(n-propyl)carbomoyl and diisopropylcarbamoyl.

"Mono-lower alkylcarbamoylamino" is an amino ($-NH_2$) one of whose hydrogen atoms is substituted with mono-lower alkylcarbamoyl group, specific examples including methylcarbamoylamino, ethylcarbamoylamino, n-propylcarbamoylamino, isopropylcarbamoylamino, n-butylcarbamoylamino, sec-butylcarbamoylamino and tert-butylcarbamoylamino.

"Di-lower alkylcarbamoylamino" is an amino ($-NH_2$) one of whose hydrogen atoms is substituted with di-lower alkylcarbamoyl, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino and di(tert-butyl)carbamoylamino.

"Mono-lower alkylcarbamoyl(lower alkyl)amino" is a mono-lower alkylamino whose hydrogen on the nitrogen atom is substituted with mono-lower alkylcarbamoyl, specific examples including monomethylcarbamoyl(methyl) amino, monoethylcarbamoyl(methyl)amino and [mono(n-propyl)carbamoyl](methyl)amino.

"Di-lower alkylcarbamoyl(lower alkyl)amino" is a mono-lower alkylamino whose hydrogen on the nitrogen atom is substituted with di-lower alkylcarbamoyl, specific examples including dimethylcarbamoyl(methyl)amino, diethylcarbamoyl(methyl)amino and [di(n-propyl)carbamoyl](methyl) amino.

"Mono-lower alkylcarbamoyloxy" is a group in which mono-lower alkylcarbamoyl is bound to oxygen, specific examples including methylcarbamoyloxy, ethylcarbamoyloxy, n-propylcarbamoyloxy, isopropylcarbamoyloxy, n-butylcarbamoyloxy, sec-butylcarbamoyloxy and tert-butylcarbamoyloxy.

"Di-lower alkylcarbamoyloxy" is a group in which di-lower alkylcarbamoyl is bound to oxygen, specific examples including dimethylcarbamoyloxy, diethylcarbamoyloxy, ethylmethylcarbamoyloxy, di(n-propyl)carbamoyloxy, methyl(n-propyl)carbamoyloxy and diisopropylcarbamoyloxy.

"Lower alkylsulfonyl" is a group in which lower alkyl is bound to sulfonyl ($-SO_2$), specific examples including methylsulfonyl, ethylsulfonyl, n-propylsulfonyl, isopropylsulfonyl, n-butylsulfonyl, sec-butylsulfonyl and tert-butylsulfonyl.

"Lower alkylsulfonylamino" is an amino ($-NH_2$) one of whose hydrogen atoms is substituted with lower alkylsulfonyl, specific examples including methylsulfonylamino, ethylsulfonylamino, n-propylsulfonylamino, isopropylsulfonylamino, n-butylsulfonylamino, sec-butylsulfonylamino and tert-butylsulfonylamino.

"Lower alkylsulfonyl(lower alkyl)amino" is a group in which hydrogen on nitrogen atom of mono-lower alkylamino is substituted with lower alkylsulfonyl, specific examples including methanesulfonyl, ethanesulfonyl, n-propanesulfonyl and isopropanesulfonyl.

"Mono-lower alkylsulfamoyl" is a sulfamoyl ($-SO_2NH_2$) one of whose hydrogen atoms is substituted with lower alkyl, specific examples including monomethylsulfamoyl, monoethylsulfamoyl, mono(n-propyl)sulfamoyl, monopropylsulfamoyl, mono(n-butyl)sulfamoyl, mono(sec-butyl)sulfamoyl and mono(tert-butyl)sulfamoyl.

"Di-lower alkylsulfamoyl" is a sulfamoyl whose two hydrogen atoms are substituted with lower alkyl groups, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl and di(tert-butyl) sulfamoyl.

"Mono-lower alkylsulfamoylamino" is an amino ($-NH_2$) one of whose hydrogen atoms is substituted with mono-lower alkylsulfamoyl, specific examples including (monomethylsulfamoyl)amino, (monoethylsulfamoyl)amino, [mono(n-propyl)sulfamoyl]amino, (monoisopropylsulfamoyl)amino, [mono(n-butyl)sulfamoyl]amino, [mono(sec-butyl)sulfamoyl]amino and [mono(tert-butyl)sulfamoyl]amino.

"(Di-lower alkylsulfamoyl)amino" is an amino ($-NH_2$) one of whose hydrogen atoms is substituted with di-lower alkylsulfamoyl, specific examples including (dimethylsulfamoyl)amino, (diethylsulfamoyl)amino, (ethylmethylsulfamoyl)amino, [di(n-propyl)sulfamoyl]amino, [methyl(n-propyl)sulfamoyl]amino and (diisopropylsulfamoyl)amino.

"Mono-lower alkylsulfamoyl(lower alkyl)amino" is a mono-lower alkylamino whose hydrogen on the nitrogen atom is substituted with mono-lower alkylsulfamoyl, specific examples including monomethylsulfamoyl(methyl)amino, monoethylsulfamoyl(methyl)amino and [mono(n-propyl)sulfamoyl](methyl)amino.

"Di-lower alkylsulfamoyl(lower alkyl)amino" is a mono-lower alkylamino whose hydrogen on the nitrogen atom is substituted with di-lower alkylsulfamoyl, specific examples including dimethylsulfamoyl(methyl)amino, diethylsulfamoyl(methyl)amino and [di(n-propyl)sulfamoyl](methyl) amino.

"Pharmaceutically acceptable salts" of the pyridone derivatives that are represented by the general formula [I] include those customarily used salts which are permissible to be used as medicine, specific examples including acid addition salts at amino or at nitrogen-containing heterocycle of the compounds of formula (I) or, where the compounds of formula (I) contain carboxyl, base addition salts at the carboxyl.

As such acid addition salts, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonic acid salts such as methanesulfonate, isethionate, benzenesulfonate, p-toluenesulfonate and the like can be named.

As the base addition salts, alkali metal salts such as sodium salt, potassium salt and the like; alkaline earth metal salts such as calcium salt, magnesium salt and the like; and organic amine salts such as ammonium salt, trimethylamine salt, triethylamine salt, dicyclohexylamine salt, ethanolamine salt, diethanolamine salt, triethanolamine salt, procaine salt, N,N'-dibenzylethylenediamine salt and the like can be named.

In the compounds represented by the general formula (I), $X_1$, $X_2$, and $X_3$ may all be optionally substituted methine or any one of $X_1$, $X_2$ and $X_3$ is nitrogen and the other two are optionally substituted methine; in particular, preferably all are unsubstituted methine or any one of $X_1$, $X_2$ and $X_3$ is nitrogen and the other two are unsubstituted methine.

$X_4$, $X_5$, $X_6$ and $X_7$ may all be optionally substituted methine; in particular, preferably unsubstituted methine.

$Y_1$ is preferably a single bond or $-O-$.

$Y_2$ is preferably optionally substituted methylene, optionally substituted ethylene or optionally substituted vinylene; in particular, methylene, ethylene or vinylene.

$Y_3$ is preferably a single bond or $-O-$.

As a combination of $-Y_1-Y_2-Y_3-$, $-O-CH_2-$, $-CH_2-O-$, ethylene or vinylene are particularly preferred.

$Z_1$ is preferably single bond or optionally substituted methylene; in particular, single bond or methylene.

L is preferably optionally substituted methylene or optionally substituted lower cycloalkylene; in particular, optionally lower alkyl-substituted methylene.

$Z_2$ is preferably single bond or optionally substituted methylene; in particular, single bond or optionally lower alkyl-substituted methylene.

As optionally substituted aliphatic nitrogen-containing heterocyclic group which is formed by $R_1$, L and $Z_2$ together with the nitrogen atom to which $R_1$ binds, optionally substituted pyrrolidine ring or optionally substituted piperidine ring are preferred.

Where $R_1$, L and $Z_2$ form an optionally substituted aliphatic nitrogen-containing heterocyclic group together with the nitrogen to which $R_1$ binds, $R_2$ is preferably hydrogen, optionally substituted $C_1$-$C_4$ alkyl or optionally substituted $C_3$-$C_5$ cycloalkyl; in particular, $C_1$-$C_4$ alkyl or $C_3$-$C_5$ cycloalkyl.

Furthermore, $R_1$ and $R_2$ may be same or different and preferably selected from, independently of each other, hydrogen, optionally substituted $C_1$-$C_4$ alkyl and optionally substituted $C_3$-$C_5$ cycloalkyl; in particular, $C_1$-$C_4$ alkyl and $C_3$-$C_5$ cycloalkyl.

As optionally substituted aliphatic nitrogen-containing heterocyclic group which is formed by $R_1$ and $R_2$ together with the nitrogen to which they bind, optionally substituted pyrrolidine ring or optionally substituted piperidine ring is preferred.

Ar is preferably optionally substituted phenyl or optionally substituted pyridinyl, preferred substituent being selected from fluorine, chlorine, methyl, ethyl, hydroxyl, methoxy, ethoxy, trifluoromethyl, difluoromethoxy and trifluoromethoxy. Ar may have, for example, 1-3 of these substituents.

As the compounds of the general formula (I) provided by the present invention, for example, the following can be exemplified.

TABLE 1

| Example | Structural Formula |
|---------|--------------------|
| 1 | 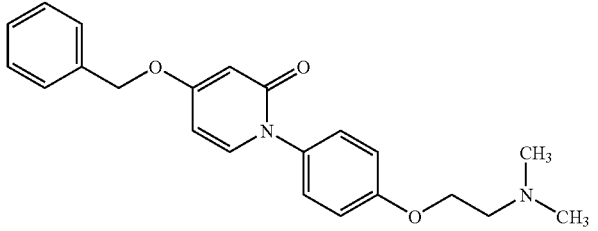 |
| 2 | 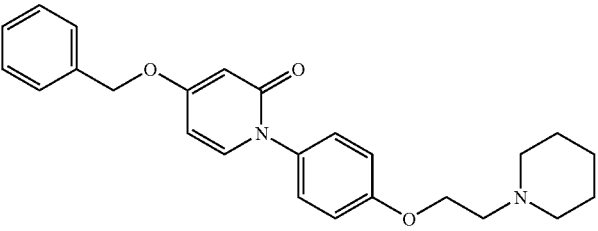 |
| 3 | 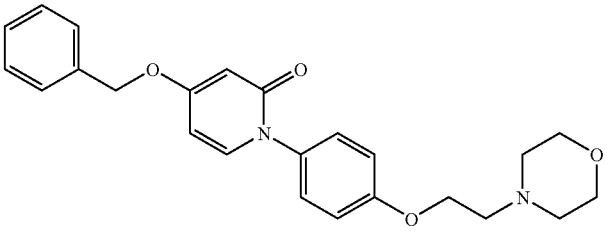 |
| 4 | 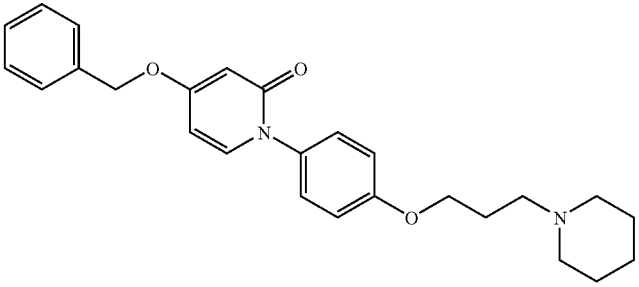 |

TABLE 1-continued
| Example | Structural Formula |
|---|---|
| 5 | 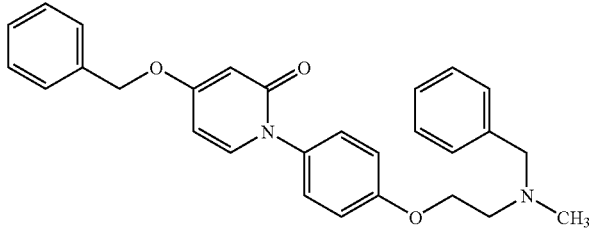 |
| 6 | 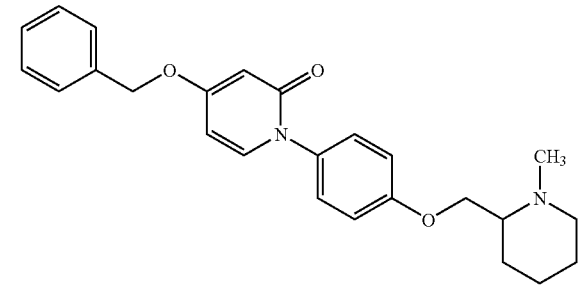 |
| 7 | 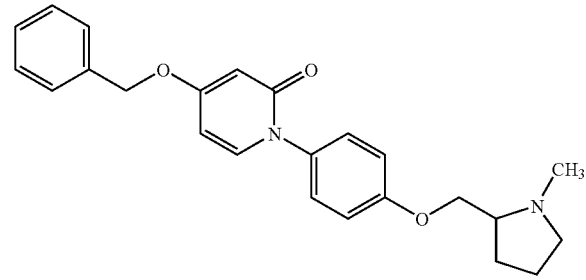 |
| 8 | 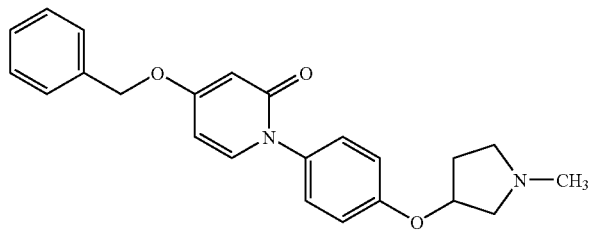 |
| 9 | 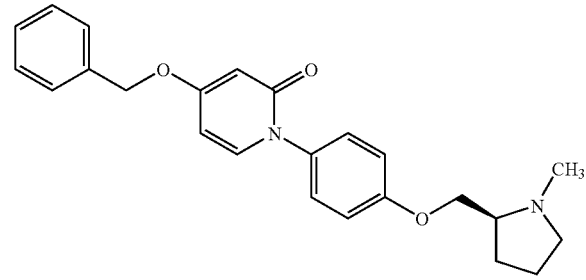 |

TABLE 1-continued

| Example | Structural Formula |
|---------|-------------------|
| 10 | 4-(benzyloxy)-1-{4-[2-(diethylamino)ethoxy]phenyl}pyridin-2(1H)-one |
| 11 | 4-(benzyloxy)-1-{6-[2-(piperidin-1-yl)ethoxy]pyridin-3-yl}pyridin-2(1H)-one |
| 12 | 4-(benzyloxy)-1-{4-[2-(pyrrolidin-1-yl)ethoxy]phenyl}pyridin-2(1H)-one |
| 13 | 4-(benzyloxy)-1-{4-[2-(diisopropylamino)ethoxy]phenyl}pyridin-2(1H)-one |
| 14 | 4-(benzyloxy)-1-{4-[1-(dimethylamino)propan-2-yloxy]phenyl}pyridin-2(1H)-one |
| 15 | 4-(benzyloxy)-1-(4-{[1-(dimethylamino)-2-methylpropan-2-yl]oxy}phenyl)pyridin-2(1H)-one |

TABLE 1-continued

| Example | Structural Formula |
| --- | --- |
| 16 | 4-(benzyloxy)-1-(4-{[(3S)-1-cyclopentylpyrrolidin-3-yl]oxy}phenyl)pyridin-2(1H)-one |
| 17 | 4-(benzyloxy)-1-(4-{[(3S)-1-isopropylpyrrolidin-3-yl]oxy}phenyl)pyridin-2(1H)-one |
| 18 | 4-(benzyloxy)-1-(4-{[(3R)-1-cyclopentylpyrrolidin-3-yl]oxy}phenyl)pyridin-2(1H)-one |
| 19 | 4-(benzyloxy)-1-(4-{[(3R)-1-isopropylpyrrolidin-3-yl]oxy}phenyl)pyridin-2(1H)-one |
| 20 | 4-(benzyloxy)-1-{5-[2-(piperidin-1-yl)ethoxy]pyridin-2-yl}pyridin-2(1H)-one |
| 21 | 4-(benzyloxy)-1-{3-methyl-4-[2-(piperidin-1-yl)ethoxy]phenyl}pyridin-2(1H)-one |

TABLE 1-continued
| Example | Structural Formula |
|---|---|
| 22 | 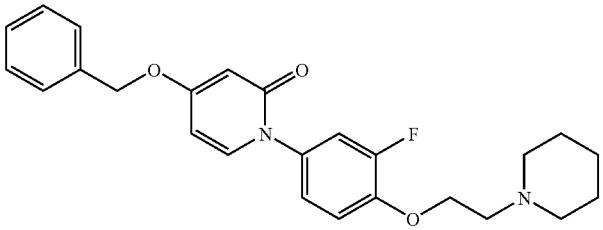 |
| 23 | 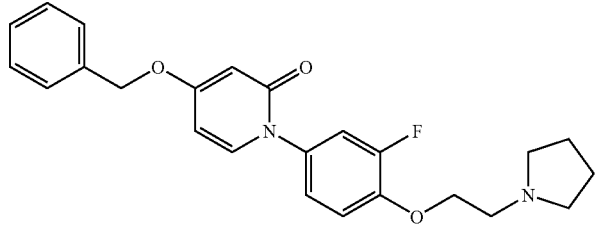 |
| 24 | 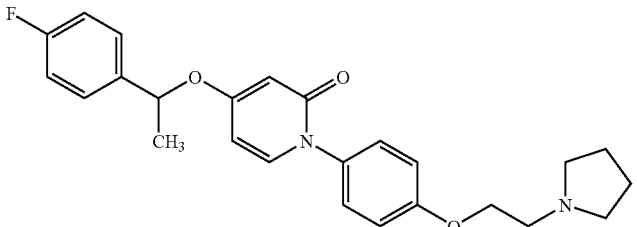 |
| 25 | 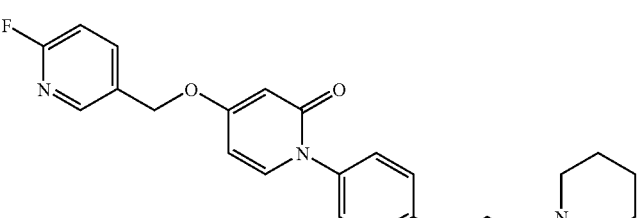 |
| 26 | 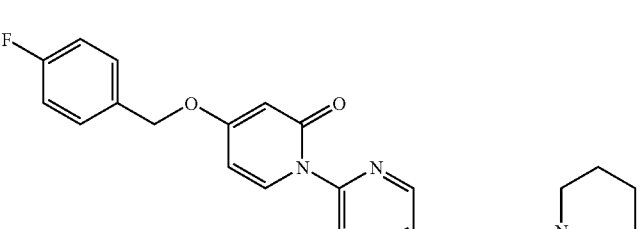 |
| 27 | 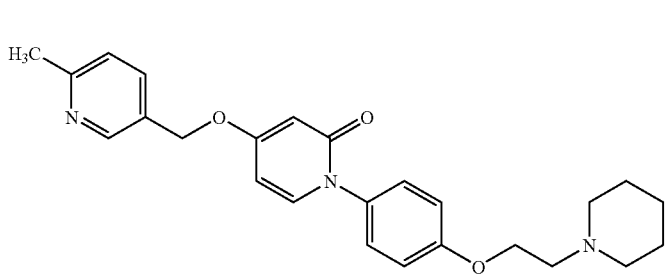 |

TABLE 1-continued

| Example | Structural Formula |
|---|---|
| 28 | 4-((4-fluorobenzyl)oxy)-1-(4-(2-(piperidin-1-yl)ethoxy)phenyl)pyridin-2(1H)-one |
| 29 | 4-((4-fluorobenzyl)oxy)-1-(4-(2-(pyrrolidin-1-yl)ethoxy)phenyl)pyridin-2(1H)-one |
| 30 | 1-(4-(2-(diethylamino)ethoxy)phenyl)-4-((4-fluorobenzyl)oxy)pyridin-2(1H)-one |
| 31 | 4-((4-fluorobenzyl)oxy)-1-(4-(2-morpholinoethoxy)phenyl)pyridin-2(1H)-one |
| 32 | 1-(4-(2-((2R,5R)-2,5-dimethylpyrrolidin-1-yl)ethoxy)phenyl)-4-((4-fluorobenzyl)oxy)pyridin-2(1H)-one |
| 33 | 4-((5-fluoropyridin-2-yl)methoxy)-1-(4-(2-(pyrrolidin-1-yl)ethoxy)phenyl)pyridin-2(1H)-one |

TABLE 1-continued
| Example | Structural Formula |
|---|---|
| 34 | 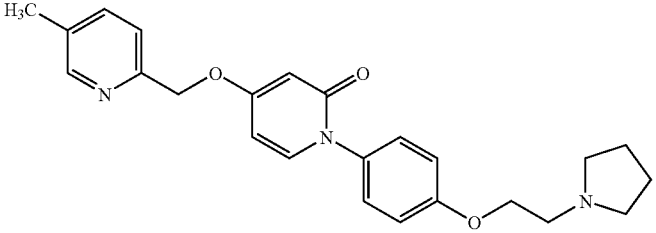 |
| 35 | 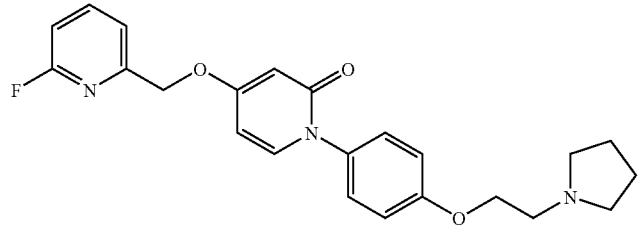 |
| 36 | 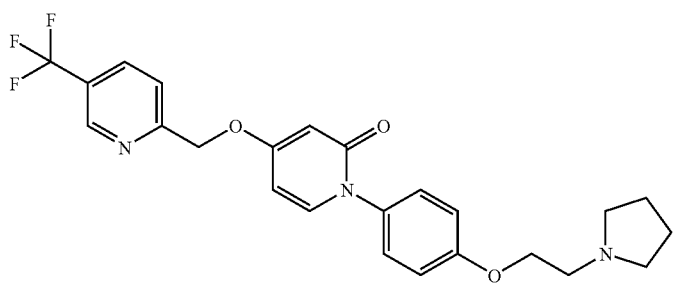 |
| 37 | 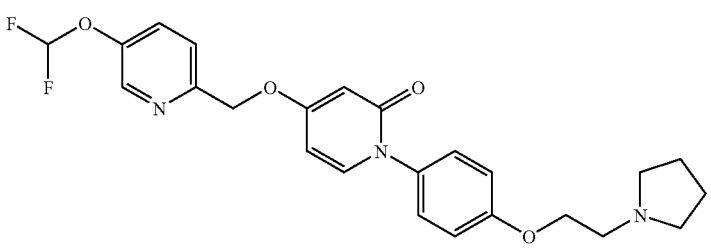 |
| 38 | 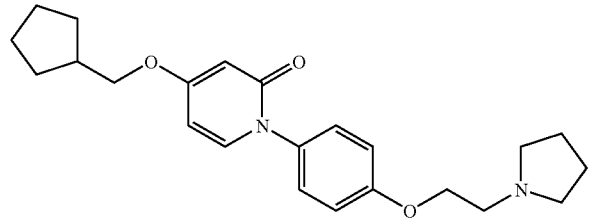 |
| 39 | 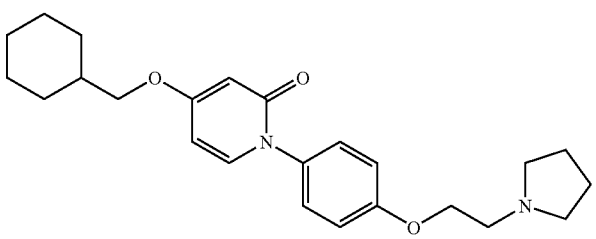 |

TABLE 1-continued
| Example | Structural Formula |
|---------|-------------------|
| 40 | 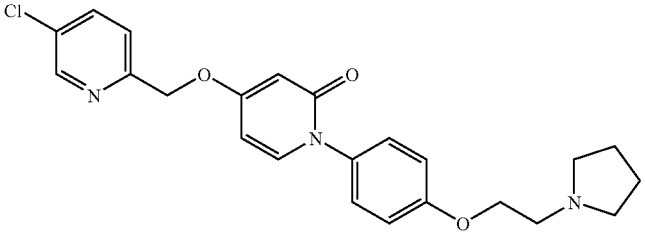 |
| 41 | 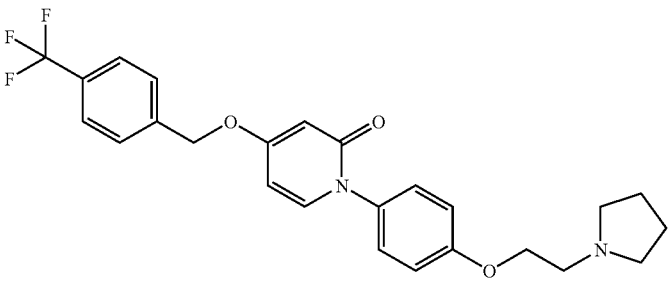 |
| 42 | 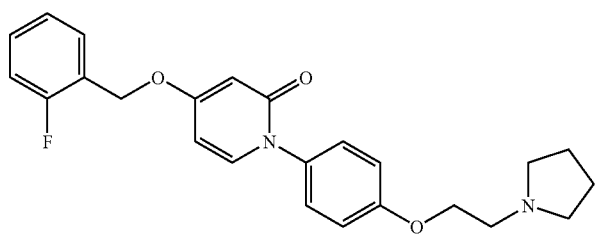 |
| 43 | 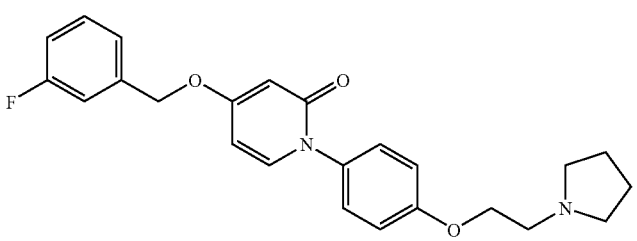 |
| 44 | 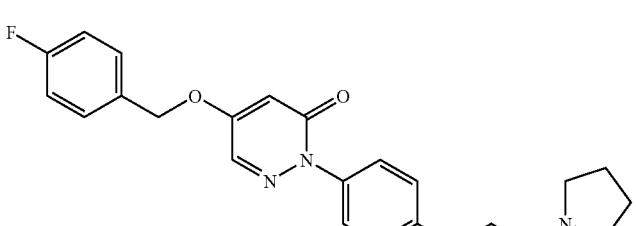 |
| 45 | 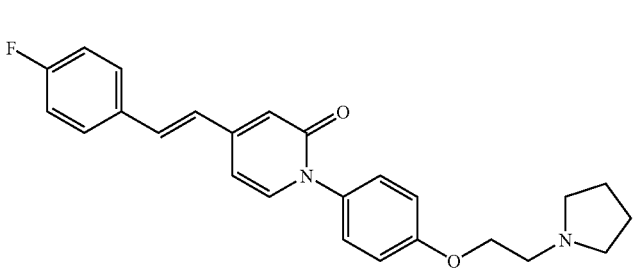 |

TABLE 1-continued
| Example | Structural Formula |
|---|---|
| 46 | 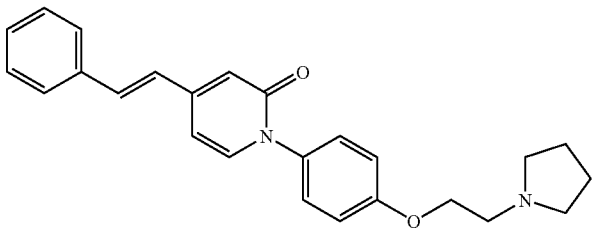 |
| 47 | 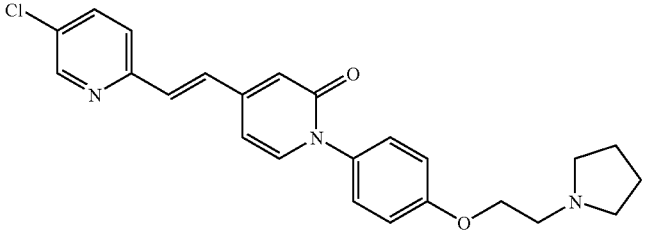 |
| 48 | 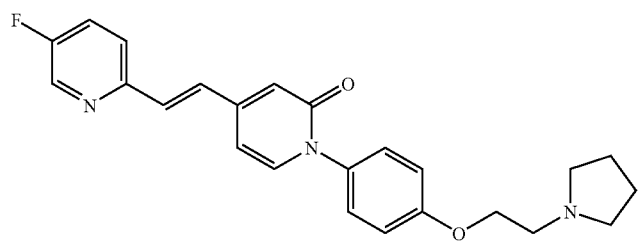 |
| 49 | 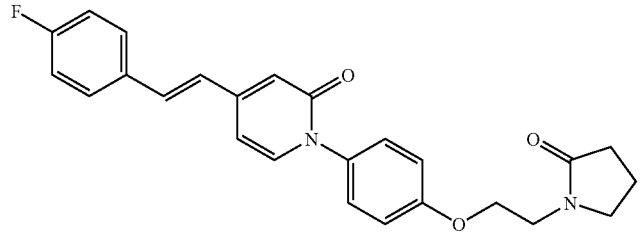 |
| 50 | 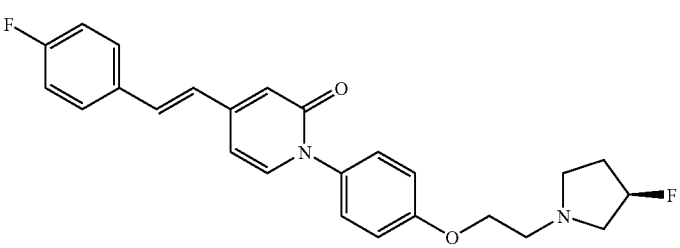 |
| 51 | 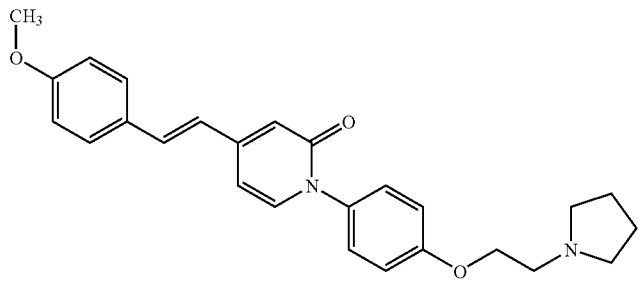 |

TABLE 1-continued

| Example | Structural Formula |
|---|---|
| 52 | |
| 53 | |
| 54 | |
| 55 | |
| 56 | |
| 57 | |

TABLE 1-continued

| Example | Structural Formula |
|---|---|
| 58 | |
| 59 | |
| 60 | |
| 61 | |
| 62 | |
| 63 | |

TABLE 1-continued
| Example | Structural Formula |
|---|---|
| 64 | 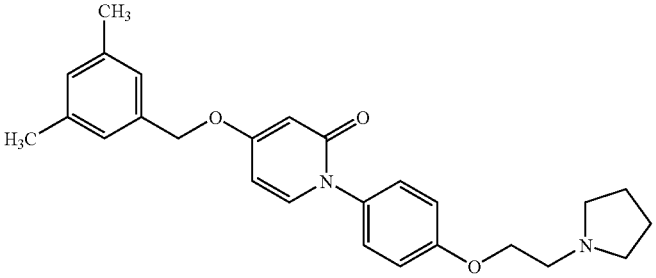 |
| 65 | 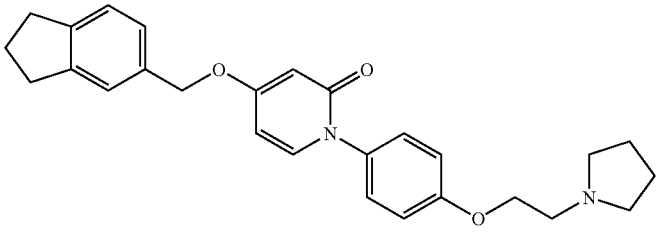 |
| 66 | 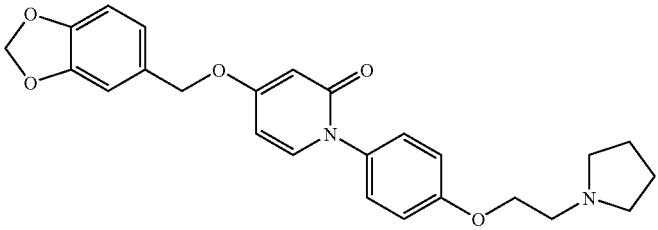 |
| 67 | 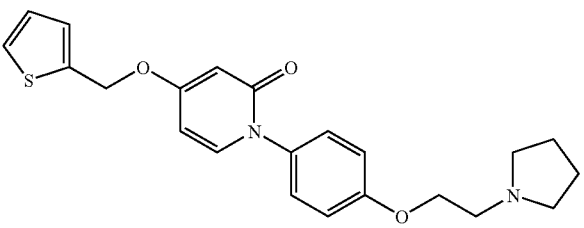 |
| 68 | 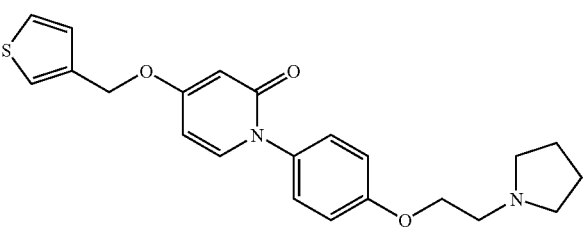 |
| 69 | 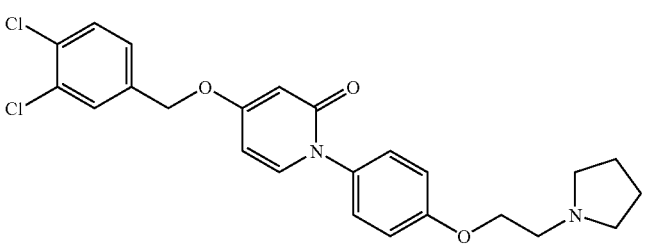 |

TABLE 1-continued

| Example | Structural Formula |
|---|---|
| 70 | (naphthalen-2-ylmethoxy)-substituted pyridin-2(1H)-one with N-[4-(2-pyrrolidin-1-ylethoxy)phenyl] group |
| 71 | 4-[(2-methoxybenzyl)oxy]-1-[4-(2-pyrrolidin-1-ylethoxy)phenyl]pyridin-2(1H)-one |
| 72 | 4-[(3-methoxybenzyl)oxy]-1-[4-(2-pyrrolidin-1-ylethoxy)phenyl]pyridin-2(1H)-one |
| 73 | 4-[(4-methoxybenzyl)oxy]-1-[4-(2-pyrrolidin-1-ylethoxy)phenyl]pyridin-2(1H)-one |
| 74 | 4-[(2-chlorobenzyl)oxy]-1-[4-(2-pyrrolidin-1-ylethoxy)phenyl]pyridin-2(1H)-one |
| 75 | 4-[(3-chlorobenzyl)oxy]-1-[4-(2-pyrrolidin-1-ylethoxy)phenyl]pyridin-2(1H)-one |

TABLE 1-continued
| Example | Structural Formula |
|---|---|
| 76 | 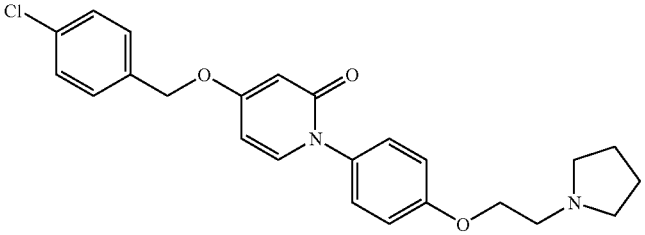 |
| 77 | 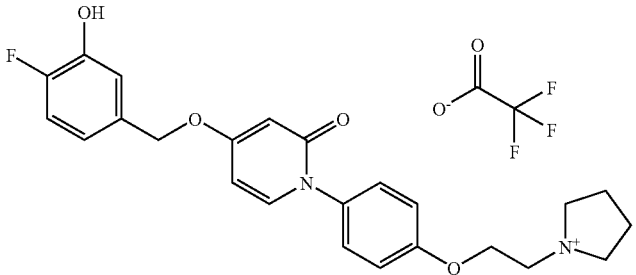 |
| 78 | 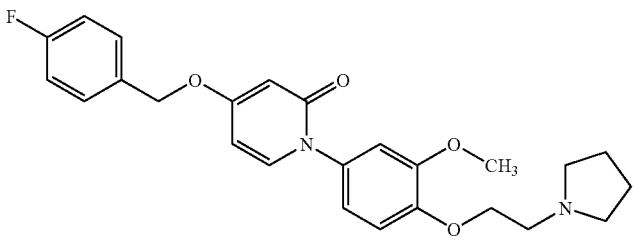 |
| 79 | 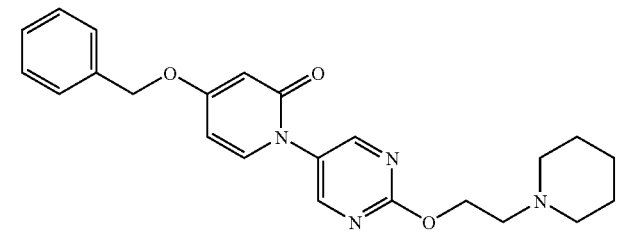 |
| 80 | 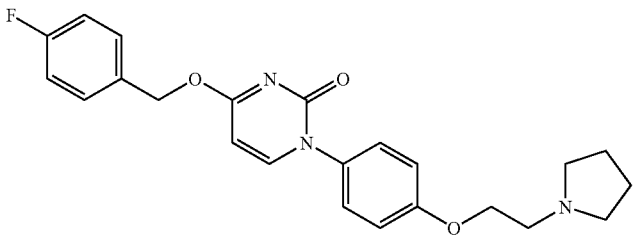 |
| 81 | 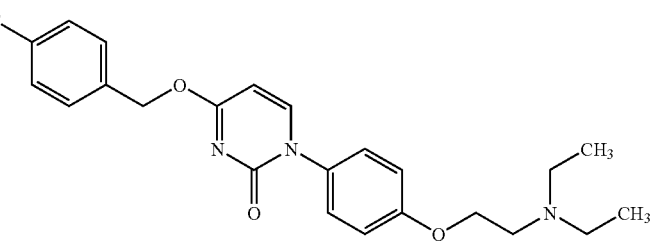 |

TABLE 1-continued
| Example | Structural Formula |
|---|---|
| 82 | 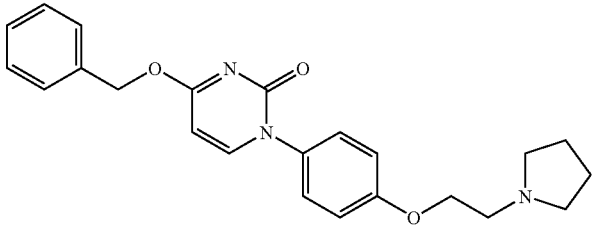 |
| 83 | 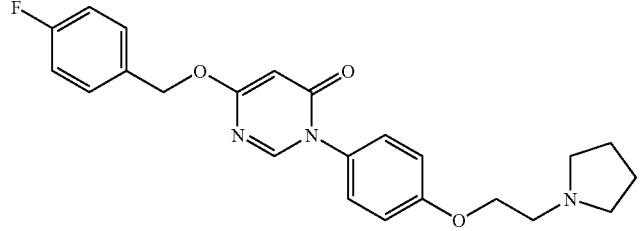 |
| 84 | 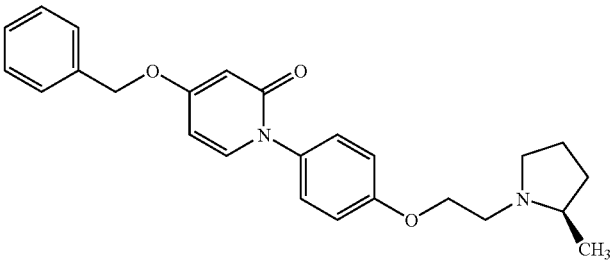 |
| 85 | 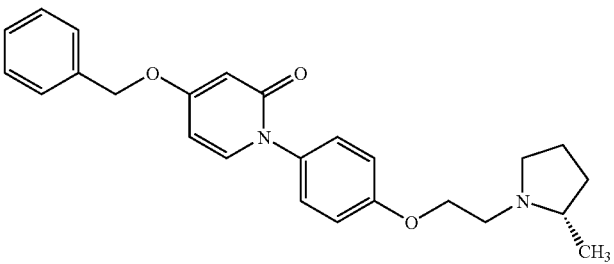 |
| 86 | 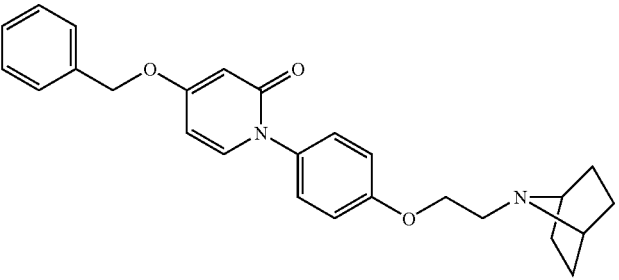 |
| 87 | 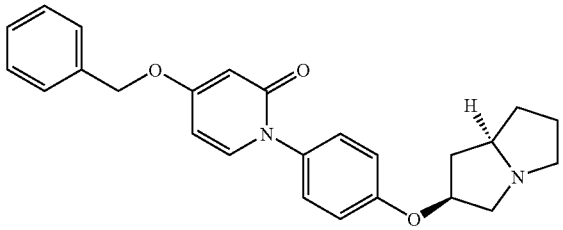 |

TABLE 1-continued
| Example | Structural Formula |
|---|---|
| 88 | 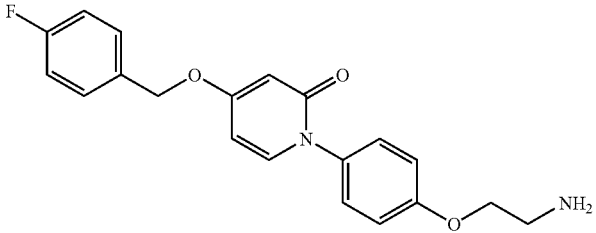 |
| 89 | 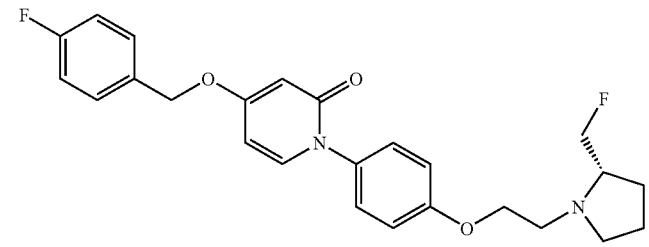 |
| 90 | 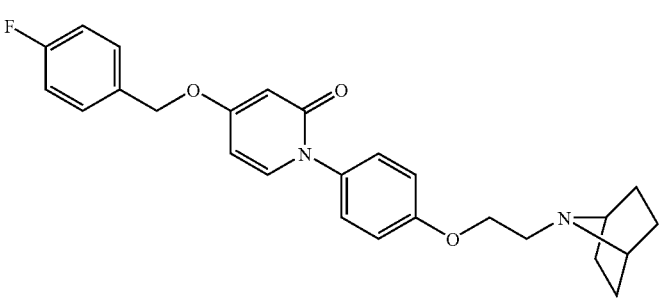 |
| 91 | 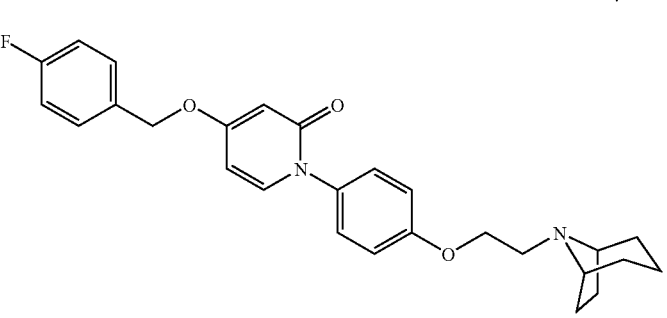 |
| 92 | 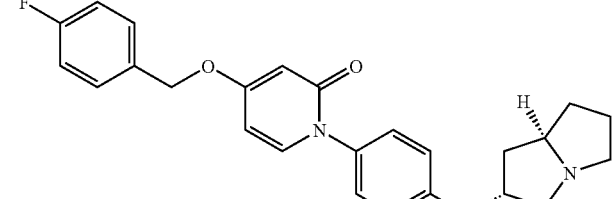 |
| 93 | 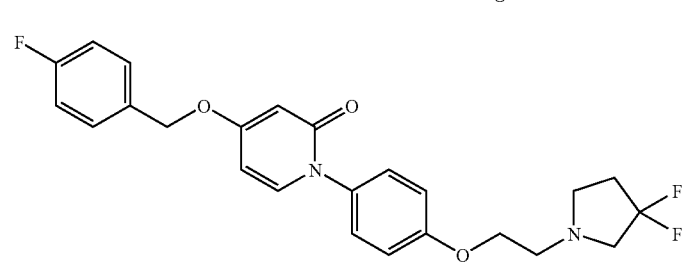 |

TABLE 1-continued
| Example | Structural Formula |
|---|---|
| 94 | 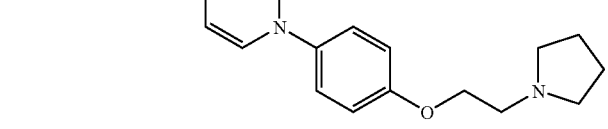 |
| 95 | 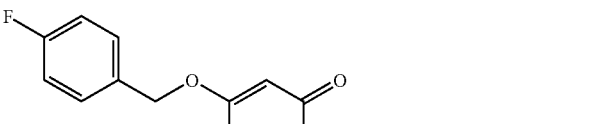 |
| 96 | 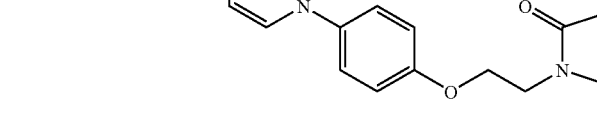 |
| 97 | 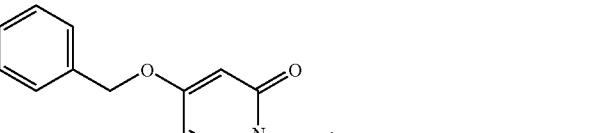 |
| 98 | 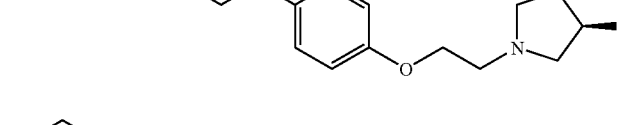 |
| 99 | 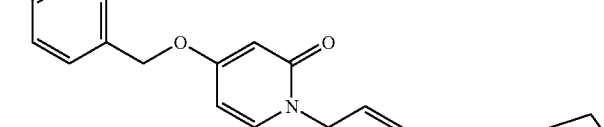 |

TABLE 1-continued

| Example | Structural Formula |
|---|---|
| 100 | (5-chloropyridin-2-yl)methoxy-pyridin-2(1H)-one N-substituted with 4-(2-(dimethylamino)ethoxy)phenyl |
| 101 | (5-chloropyridin-2-yl)methoxy-pyridin-2(1H)-one N-substituted with 4-(2-(diethylamino)ethoxy)phenyl |
| 102 | (5-chloropyridin-2-yl)methoxy-pyridin-2(1H)-one N-substituted with 4-(3-(2-oxopyrrolidin-1-yl)propoxy)phenyl |
| 103 | (5-chloropyridin-2-yl)methoxy-pyridin-2(1H)-one N-substituted with 4-(2-((2S,5S)-2,5-dimethylpyrrolidin-1-yl)ethoxy)phenyl |
| 104 | (5-chloropyridin-2-yl)methoxy-pyridin-2(1H)-one N-substituted with 4-(2-((2S)-2-methylpyrrolidin-1-yl)ethoxy)phenyl |
| 105 | (5-chloropyridin-2-yl)methoxy-pyridin-2(1H)-one N-substituted with 4-(2-((3S)-3-fluoropyrrolidin-1-yl)ethoxy)phenyl |

TABLE 1-continued

| Example | Structural Formula |
|---------|--------------------|
| 106 | |
| 107 | |
| 108 | |
| 109 | |
| 110 | |
| 111 | |

TABLE 1-continued

| Example | Structural Formula |
|---|---|
| 112 | (5-chloropyridin-2-yl)methoxy-pyridin-2(1H)-one, N-[4-(2-(N-ethyl-N-propylamino)ethoxy)phenyl] |
| 113 | (5-chloropyridin-2-yl)methoxy-pyridin-2(1H)-one, N-[4-(2-(N-ethyl-N-isopropylamino)ethoxy)phenyl] |
| 114 | (5-chloropyridin-2-yl)methoxy-pyridin-2(1H)-one, N-[4-(2-(N-ethyl-N-methylamino)ethoxy)phenyl] |
| 115 | (5-chloropyridin-2-yl)methoxy-pyridin-2(1H)-one, N-[4-(2-(N-isopropyl-N-methylamino)ethoxy)phenyl] |
| 116 | (5-chloropyridin-2-yl)methoxy-pyridin-2(1H)-one, N-[4-(2-(N-methyl-N-propylamino)ethoxy)phenyl] |
| 117 | (4-fluorobenzyl)oxy-pyridin-2(1H)-one, N-[4-(2-(N-methyl-N-propylamino)ethoxy)phenyl] |

TABLE 1-continued

| Example | Structural Formula |
|---|---|
| 118 | |
| 119 | |
| 120 | |
| 121 | |
| 122 | |
| 123 | |

TABLE 1-continued

| Example | Structural Formula |
|---|---|
| 124 | |
| 125 | |
| 126 | |
| 127 | |
| 128 | |
| 129 | |

TABLE 1-continued

| Example | Structural Formula |
|---------|-------------------|
| 130 | |
| 131 | |
| 132 | |
| 133 | |
| 134 | |

TABLE 1-continued
| Example | Structural Formula |
|---|---|
| 135 | 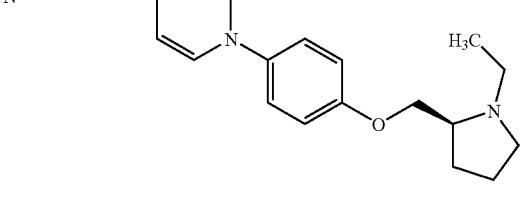 |
| 136 | 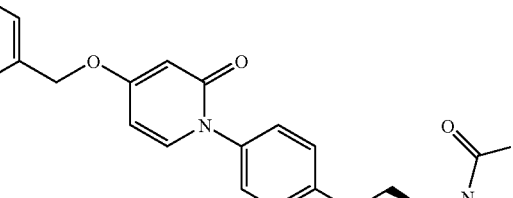 |
| 137 | 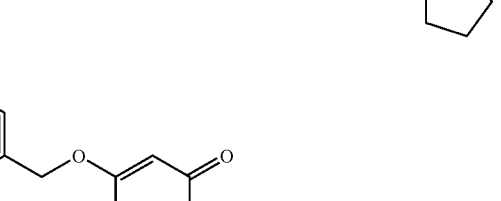 |
| 138 | 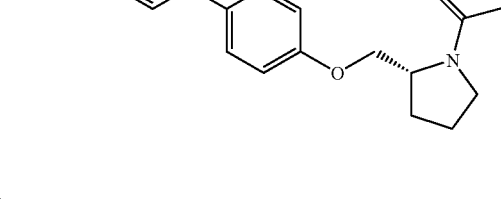 |
| 139 | 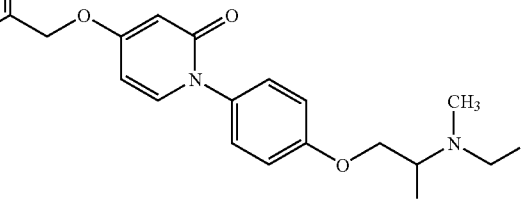 |

TABLE 1-continued

| Example | Structural Formula |
|---------|--------------------|
| 140 | |
| 141 | |
| 142 | |
| 143 | |
| 144 | |

TABLE 1-continued

| Example | Structural Formula |
| --- | --- |
| 145 | [5-chloropyridin-2-yl-methoxy-pyridin-2(1H)-one with N-(4-(2-(propylamino)ethoxy)phenyl) substituent] |
| 146 | [5-chloropyridin-2-yl-methoxy-pyridin-2(1H)-one with N-(4-(2-(isopropylamino)ethoxy)phenyl) substituent] |
| 147 | [5-chloropyridin-2-yl-methoxy-pyridin-2(1H)-one with N-(4-(2-((S)-sec-butylamino)ethoxy)phenyl) substituent] |
| 148 | [5-chloropyridin-2-yl-methoxy-pyridin-2(1H)-one with N-(4-(2-((R)-sec-butylamino)ethoxy)phenyl) substituent] |
| 149 | [5-chloropyridin-2-yl-methoxy-pyridin-2(1H)-one with N-(4-(2-(tert-butylamino)ethoxy)phenyl) substituent] |

TABLE 1-continued
| Example | Structural Formula |
|---|---|
| 150 | 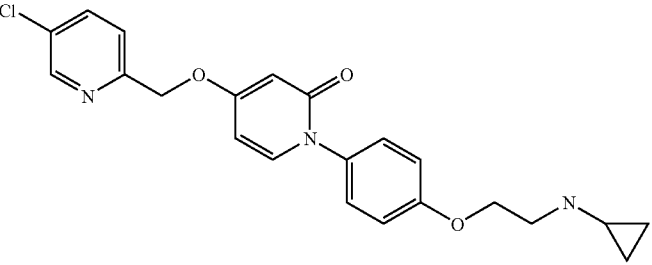 |
| 151 | 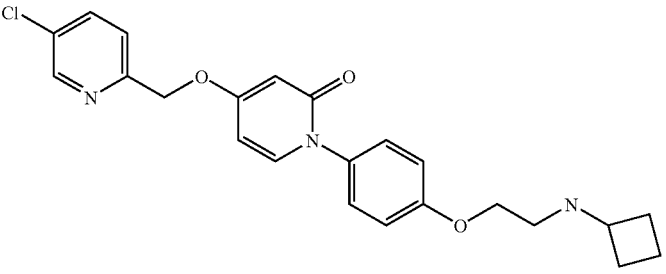 |
| 152 | 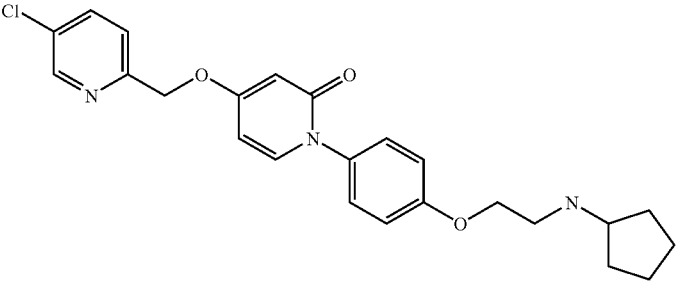 |
| 153 | 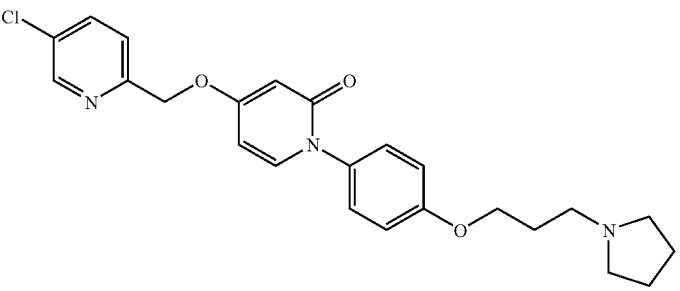 |
| 154 | 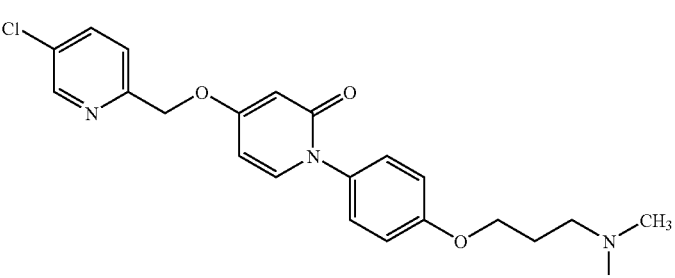 |

TABLE 1-continued
| Example | Structural Formula |
|---|---|
| 155 | 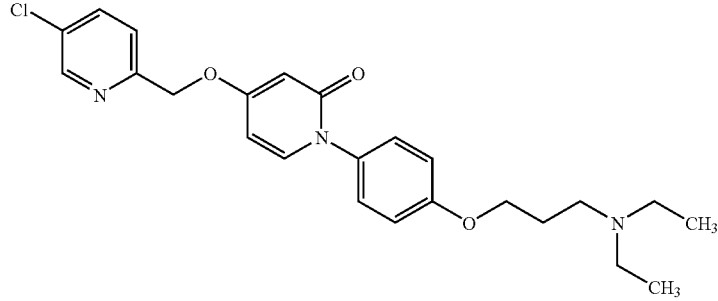 |
| 156 | 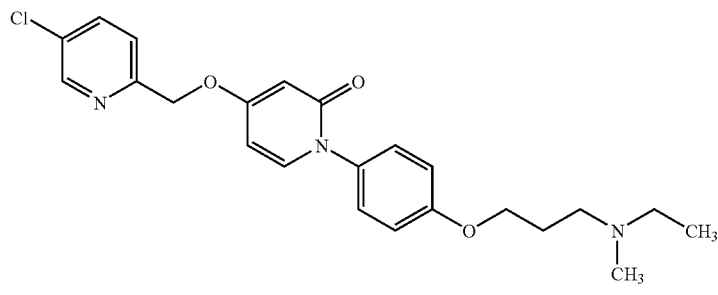 |
| 157 | 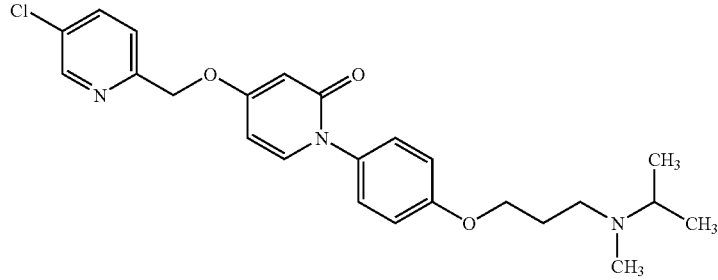 |
| 158 | 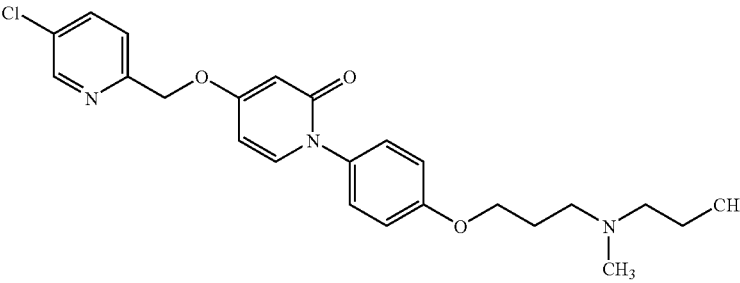 |
| 159 | 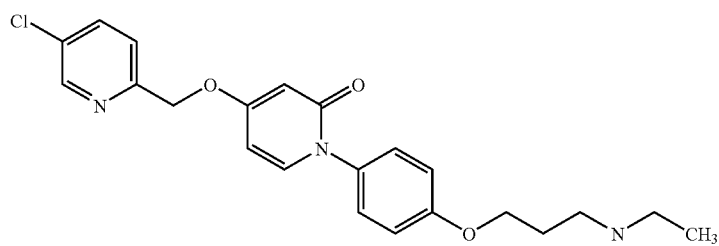 |

TABLE 1-continued

| Example | Structural Formula |
|---|---|
| 160 | |

Of those compounds represented by the general formula (I), preferred specific examples are as follows:

4-benzyloxy-1-{4-[2-(dimethylamino)ethoxy]phenyl}-1H-pyridin-2-one
4-benzyloxy-1-{4-[2-(1-piperidinyl)ethoxy]phenyl}-1H-pyridin-2-one
4-benzyloxy-1-{4-[3-(1-piperidinyl)propyloxy]phenyl}-1H-pyridin-2-one
4-benzyloxy-1-(4-{2-[benzyl(methyl)amino]ethoxy}phenyl)-1H-pyridin-2-one
4-benzyloxy-1-(4-{[(2S)-1-methyl-2-pyrrolidinyl]methoxy}phenyl)-1H-pyridin-2-one
4-benzyloxy-1-{4-[2-(diethylamino)ethoxy]phenyl}-1H-pyridin-2-one
4-benzyloxy-1-{4-[2-(1-pyrrolidinyl)ethoxy]phenyl}-1H-pyridin-2-one
4-benzyloxy-1-{4-[2-(diisopropylamino)ethoxy]phenyl}-1H-pyridin-2-one
4-benzyloxy-1-(4-{[(3R)-1-cyclopentyl-3-pyrrolidinyl]oxy}phenyl)-1H-pyridin-2-one
4-benzyloxy-1-(4-{[(3R)-1-isopropyl-3-pyrrolidinyl]oxy}phenyl)-1H-pyridin-2-one
4-benzyloxy-1-{3-methyl-4-[2-(1-piperidinyl)ethoxy]phenyl}-1H-pyridin-2-one
4-benzyloxy-1-{3-fluoro-4-[2-(1-piperidinyl)ethoxy]phenyl}-1H-pyridin-2-one
4-benzyloxy-1-{3-fluoro-4-[2-(1-pyrrolidinyl)ethoxy]phenyl}-1H-pyridin-2-one
4-(4-fluorobenzyloxy)-1-{4-[2-(1-piperidinyl)ethoxy]phenyl}-1H-pyridin-2-one
4-(4-fluorobenzyloxy)-1-{4-[2-(1-pyrrolidinyl)ethoxy]phenyl}-1H-pyridin-2-one
1-{4-[2-(diethylamino)ethoxy]phenyl}-4-(4-fluorobenzyloxy)-1H-pyridin-2-one
4-(4-fluorobenzyloxy)-1-{4-[2-(trans-2,5-dimethyl-1-pyrrolidinyl)-ethoxy]phenyl}-1H-pyridin-2-one
4-[(5-chloro-2-pyridinyl)methoxy]-1-{4-[2-(1-pyrrolidinyl)ethoxy]-phenyl}-1H-pyridin-2-one
4-[4-(trifloromethyl)benzyloxy]-1-{4-[2-(1-pyrrolidinyl)ethoxy]-phenyl}-1H-pyridin-2-one
4-(2-fluorobenzyloxy)-1-{4-[2-(1-pyrrolidinyl)ethoxy]phenyl}-1H-pyridin-2-one
4-(3-fluorobenzyloxy)-1-{4-[2-(1-pyrrolidinyl)ethoxy]phenyl}-1H-pyridin-2-one
4-[(E)-2-(4-fluorophenyl)vinyl]-1-{4-[2(1-(pyrrolidinyl)ethoxy]phenyl}-1H-pyridin-2-one
4-[(E)-2-phenylvinyl]-1-{4-[2-(1-pyrrolidinyl)ethoxy]phenyl}-1H-pyridin-2-one
4-[(E)-2-(5-chloro-2-pyridinyl)vinyl]-1-{4-[2-(1-pyrrolidinyl)ethoxy]phenyl}-1H-pyridin-2-one
4-[(E)-2-(5-fluoro-2-pyridinyl)vinyl]-1-{4-[2-(1-pyrrolidinyl)ethoxy]phenyl}-1H-pyridin-2-one
4-[(E)-2-(4-fluorophenyl)vinyl]-1-{4-[2-(2oxo-1-pyrrolidinyl)ethoxy]phenyl{-1H-pyridin-2-one
4-[(E)-2-(4-fluorophenyl)vinyl]-1-(4-{2-[(3R)-3-fluoro-1-pyrrolidinyl]ethoxy}-phenyl)-1H-pyridin-2-one
4-(2-phenylethyl)-1-{4-[2-(1-pyrrolidinyl)ethoxy]phenyl}-1H-pyridin-2-one
4-[2-(4-fluorophenyl)ethyl]-1-{4-[2-(1-pyrrolidinyl)ethoxy]phenyl}-1H-pyridin-2-one
4-(2,3-dihydro-1H-inden-5-ylmethoxy)-1-{4-[2-(1-pyrrolidinyl)-ethoxy]phenyl}-1H-pyridin-2-one
1-{4-[2-(1-pyrrolidinyl)ethoxy]phenyl}-4-(3-thienyl-methoxy)-1H-pyridin-2-one
4-[(3,4-dichlorobenzyl)oxy]-1-{4-[2-(1-pyrrolidinyl)ethoxy]phenyl}-1H-pyridin-2-one
4-(4methoxybenzyloxy)-1-{4-[2-(1-pyrrolidinyl)ethoxy]phenyl}-1H-pyridin-2-one
4-(3-chlorobenzyloxy)-1-{4-[2-(1-pyrrolidinyl)ethoxy]phenyl}-1H-pyridin-2-one
4-(4-chlorobenzyloxy)-1-{4-[2-(1-pyrrolidinyl)ethoxy]phenyl}-1H-pyridin-2-one
4-[(4-fluorobenzyloxy)-1-{3-methoxy-4-[2-(1-pyrrolidinyl)ethoxy]phenyl}-1H-pyridin-2-one
4-(4-fluorobenzyloxy)-1-{4-[2-(1-pyrrolidinyl)ethoxy]phenyl}-1H-pyrimidin-2-one
4-(4-fluorobenzyloxy)-1-{4-[2-(diethylamino)ethoxy]phenyl}-1H-pyrimidin-2-one
4-benzyloxy-1-{4-[2-(1-pyrrolidinyl)ethoxy]phenyl}-1H-pyrimidin-2-one
4-benzyloxy-1-(4-{2-[(2R)-2-methyl-1-pyrrolidinyl]ethoxy}phenyl)-1H-pyridin-2-one
4-benzyloxy-1-(4-{2-[(2S)-2-methyl-1-pyrrolidinyl]ethoxy}phenyl)-1H-pyridin-2-one
1-{4-[2-(7-azabicyclo[2.2.1]hept-7-yl)ethoxy]phenyl}-4-benzyloxy-1H-pyridin-2-one
1-{4-[2-(7-azabicyclo[2.2.1]hept-7-yl)ethoxy]phenyl}-4-(4-fluorobenzyloxy-1H-pyridin-2-one
1-{4-[2-(8-azabicyclo[3.2.1]oct-8-yl)ethoxy]phenyl}-4-(4-fluorobenzyloxy)-1H-pyridin-2-one
4-(4-fluorobenzyloxy)-1-{4-[(2R,7aR)-hexahydro-1H-pyrrolidin-2-yloxy]phenyl}-1H-pyridin-2-one
4-(4-fluorobenzyloxy)-1-(4-{2-[(3S)-3-fluoro-1-pyrrolidinyl]ethoxy}phenyl)-1H-pyridin-2-one
4-(4-fluorobenzyloxy)-1-(4-{2-[(3R)-3-methoxy-1-pyrrolidinyl]ethoxy}phenyl)-1H-pyridin-2-one
4-(4-chlorobenzyloxy)-1-(4-{2-[(3R)-3-fluoro-1-pyrrolidinyl]ethoxy}phenyl)-1H-pyridin-2-one
4-[(5-chloro-2-pyridinyl)methoxy]-1-{4-[2(dimethylamino)ethoxy]phenyl}-1H-pyridin-2-one 4-[(5-chloro-2-pyridinyl)methoxy]-1-{4-[2-(diethylamino)ethoxy]phenyl}-1H-pyridin-2-one 4-[(5-chloro-2-pyridinyl)methoxy]-1-(4-{2-[(2R,5R)-2,5-dimethyl-1-pyrrolidinyl]ethoxy}phenyl)-1H-pyridin-2-one 4-[(5-chloro-2-pyridinyl)methoxy]-1-(4-{2-[(2R)-2-methyl-1-pyrrolidinyl]-ethoxy}phenyl)-1H-pyridin-2-one 4-[(5-chloro-2-pyridinyl)methoxy]-1-(4-{2-[(3R)-3-fluoro-1-pyrrolidinyl]-ethoxy}phenol)-1H-pyridin-2-one 4-[(5-chloro-2-pyridinyl)methoxy]-1-(4-{2-[(3R)-3-methoxy-1-pyrrolidinyl]-ethoxy}phenyl)-1H-pyridin-2-one 4-[(5-chloro-2-pyridinyl)methoxy]-1-(4-[2-(diisopropylamino)ethoxy]-phenyl}-1H-pyridin-2-one 4-[(5-chloro-2-pyridinyl)methoxy]-1-(4-{2-[(3R)-3-hydroxy-1-pyrrolidinyl]-ethoxy}phenyl)-1H-pyridin-2-one 4-[(5-chloro-2-pyridinyl)methoxy]-1-(4-{2-[(3S)-3-hydroxy-1-pyrrolidinyl]-ethoxy}phenyl)-1H-pyridin-2-one 4-[(5-chloro-2-pyridinyl)methoxy]-1-(4-{2-[(3R)-3-(2-fluoroethoxy)-1-pyrrolidinyl]ethoxy}phenyl)-1H-pyridin-2-one 4-[(5-chloro-2-pyridinyl)methoxy]-1-(4-{2-[ethyl(propyl)amino]ethoxy}-phenyl)-1H-pyridin-2-one 4-[(5-chloro-2-pyridinyl)methoxy]-1-(4-{2-[ethyl(isopropyl)amino]ethoxy}-phenyl)-1H-pyridin-2-one 4-[(5-chloro-2-pyridinyl)methoxy]-1-(4-{2-[ethyl(methyl)amino]ethoxy}-phenyl)-1H-pyridin-2-one 4-[(5-chloro-2-pyridinyl)methoxy]-1-(4-{2-[(isopropyl(methyl)amino]-ethoxy}phenyl)-1H-pyridin-2-one 4-[(5-chloro-2-pyridinyl)methoxy]-1-(4-{2-[(methyl(propyl)amino]ethoxy}-phenyl)-1H-pyridin-2-one 4-(4-fluorobenzyloxy)-1-(4-{2-[methyl(propyl)amino]ethoxy}phenyl)-1H-pyridin-2-one 4-(4-fluorobenzyloxy)-1-(4-{2-[isopropyl(methyl)amino]ethoxy}phenyl)-1H-pyridin-2-one 4-[(5-chloro-2-pyridinyl)methoxy]-1-{4-[(2R)-2-diethylamino)propoxy]-phenyl}-1H-pyridin-2-one 4-[(5-chloro-2-pyridinyl)methoxy]-1-{4-[(2S)-2-(diethylamino)propoxy]-phenyl}-1H-pyridin-2-one 4-[(5-chloro-2-pyridinyl)methoxy]-1-(4-{[(3R)-3-pyrrolidinyl]oxy}phenyl)-1H-pyridin-2-one 4-[(5-chloro-2-pyridinyl)methoxy]-1-(4-{[(3R)-1-isopropyl-3-pyrrolidinyl]-oxy}phenyl)-1H-pyridin-2-one 4-[(5-chloro-2-pyridinyl)methoxy]-1-(4-{[(3R)-1-ethyl-3-pyrrolidinyl]oxy}-phenyl)-1H-pyridin-2-one 4-[(5-chloro-2-pyridinyl)methoxy]-1-(4-{[(3R)-1-methyl-3-pyrrolidinyl]oxy}-phenyl)-1H-pyridin-2-one 4-[(5-chloro-2-pyridinyl)methoxy]-1-(4-{[(2R)-2-pyrrolidinyl]methoxy}-phenyl)-1H-pyridin-2-one 4-[(5-chloro-2-pyridinyl)methoxy]-1-{(4-{[(2S)-2-pyrrolidinyl]methoxy}-phenyl)-1H-pyridin-2-one 4-[(5-chloro-2-pyridinyl)methoxy]-1-(4-{[(2S)-1-isopropyl-2-pyrrolidinyl]-methoxy}phenyl)-1H-pyridin-2-one 4-[(5-chloro-2-pyridinyl)methoxy]-1-(4-{[(2R)-1-isopropyl-2-pyrrolidinyl]-methoxy}phenyl)-1H-pyridin-2-one 4-[(5-chloro-2-pyridinyl)methoxy]-1-(4-{[(2R)-1-cyclobutyl-2-pyrrolidinyl]-methoxy}phenyl)-1H-pyridin-2-one 4-[(5-chloro-2-pyridinyl)methoxy]-1-(4-{[(2S)-1-methyl-2-pyrrolidinyl]-methoxy}phenyl)-1H-pyridin-2-one 4-[(5-chloro-2-pyridinyl)methoxy]-1-(4-{[(2S)-1-ethyl-2-pyrrolidinyl]-methoxy}phenyl)-1H-pyridin-2-one 4-[(5-chloro-2-pyridinyl)methoxy]-1-(4-{(2R)-2-[ethyl(methyl)amino]-propoxy}phenyl-1H-pyridin-2-one 4-[(5-chloro-2-pyridinyl)methoxy]-1-{(4-{(2S)-2-[ethyl(methyl)amino]-propoxy}phenyl)-1H-pyridin-2-one 4-[(5-chloro-2-pyridinyl)methoxy]-1-{4-[(2R)-2-(dimethylamino)propoxy]-phenyl}-1H-pyridin-2-one 4-[(5-chloro-2-pyridinyl)methoxy]-1-{4-[(2S)-2-(dimethylamino)propoxy]-phenyl}-1H-pyridin-2-one 4-[(5-chloro-2-pyridinyl)methoxy]-1-(4-{(2R)-2-[methyl(propyl)amino]-propoxy}phenyl)-1H-pyridin-2-one 4-[(5-chloro-2-pyridinyl)methoxy]-1-(4-{(2S)-2-[methyl(propyl)amino]-propoxy}phenyl)-1H-pyridin-2-one 4-[(5-chloro-2-pyridinyl)methoxy]-1-(4-{(2R)-2-isopropyl(methyl)amino]-propoxy}phenyl)-1H-pyridin-2-one 4-[(5-chloro-2-pyridinyl)methoxy]-1-(4-{(2S)-2-[isopropyl(methyl)amino]-propoxy}phenyl)-1H-pyridin-2-one 4-[(5-chloro-2-pyridinyl)methoxy]-1-{4-[(2R)-2-(1-pyrrolidinyl)propoxy]-phenyl}-1H-pyridin-2-one 4-[(5-chloro-2-pyridinyl)methoxy]-1-{4-[(2S)-2-(1-pyrrolidinyl)propoxy]-phenyl}-1H-pyridin-2-one 4-[(5-chloro-2-pyridinyl)methoxy]-1-{4-[2-(isopropylamino)ethoxy]phenyl}-1H-pyridin-2-one 4-[(5-chloro-2-pyridinyl)methoxy]-1-(4-{2-[(2R)-2-butylamino]ethoxy}-phenyl)-1H-pyridin-2-one 4-[(5-chloro-2-pyridinyl)methoxy]-1-(4-{2-[(2S)-2-butylamino]ethoxy}-phenyl)-1H-pyridin-2-one 4-[(5-chloro-2-pyridinyl)methoxy]-1-{4-[2-(cyclopentylamino)ethoxy]-phenyl}-1H-pyridin-2-one 4-[(5-chloro-2-pyridinyl)methoxy]-1-{4-[3(diethylamino)propoxy]phenyl}-1H-pyridin-2-one 4-[(5-chloro-2-pyridinyl)methoxy]-1-(4-{3-[methyl(propyl)amino]propoxy}-phenyl)-1H-pyridin-2-one Among the above compounds, particularly the following compound groups are advantageously used.

Group A:

4-benzyloxy-1-{4-[2-(dimethylamino)ethoxy]phenyl}-1H-pyridin-2-one 4-benzyloxy-1-{4-[2-(diethylamino)ethoxy]phenyl}-1H-pyridin-2-one 1-{4-[2-(diethylamino)ethoxy]phenyl}-4-(4-fluorobenzyloxy)-1H-pyridin-2-one 4-(4-fluorobenzyloxy)-1-{4-[2-(diethylamino)ethoxy]phenyl}-1H-pyrimidin-2-one 4-[(5-chloro-2-pyridinyl)methoxy]-1-{4-[2-(dimethylamino)ethoxy]phenyl}-1H-pyridin-2-one 4-[(5-chloro-2-pyridinyl)methoxy]-1-{4-[2-(diethylamino)ethoxy]phenyl}-1H-pyridin-2-one 4-[(5-chloro-2-pyridinyl)methoxy]-1-(4-{2-[ethyl(methyl)amino]-ethoxy}-phenyl)-1H-pyridin-2-one 4-[(5-chloro-2-pyridinyl)methoxy]-1-(4-{2-[isopropyl(methyl)amino]-ethoxy}phenyl)-1H-pyridin-2-one 4-(4-fluorobenzyloxy)-1-(4-{2-[isopropyl(methyl)amino]ethoxy}phenyl)-1H-pyridin-2-one 4-[(5-chloro-2-pyridinyl)methoxy]-1-{4-[2-(isopropylamino)ethoxy]phenyl}-1H-pyridin-2-one 4-[(5-chloro-2-pyridinyl)methoxy]-1-(4-{2-[(2R)-2-butylamino]ethoxy}-phenyl)-1H-pyridin-2-one 4-[(5-chloro-2-pyridinyl)methoxy]-1-(4-{2-[(2S)-2-butylamino]ethoxy}-phenyl)-1H-pyridin-2-one and 4-[(5-chloro-2-pyridinyl)methoxy]-1-{4-[2-(cyclopentylamino)ethoxy]phenyl}-1H-pyridin-2-one Group B:

4-benzyloxy-1-(4-{[(2S)-1-methyl-2-pyrrolidinyl]methoxy}phenyl)1H-pyridin-2-one

4-[(5-chloro-2-pyridinyl)methoxy]-1-{4-[(2R)-2-(diethylamino)propoxy]phenyl}-1H-pyridin-2-one 4-[(5-chloro-2-pyridinyl)methoxy]-1-{4-[(2S)-2-(diethylamino)propoxy]-phenyl}-1H-pyridin-2-one 4-[(5-chloro-2-pyridinyl)methoxy]-1-(4-{[(2S)-1-isopropyl-2-pyrrolidinyl]-methoxy}phenyl-1H-pyridin-2-one 4-[(5-chloro-2-pyridinyl)methoxy]-1-(4-{[(2S)-1-methyl-2-pyrrolidinyl]-methoxy}phenyl)-1H-pyridin-2-one 4-[(5-chloro-2-pyridinyl)methoxy]-1-(4-{[(2S)-1-ethyl-2-pyrrolidinyl]-methoxy}phenyl)-1H-pyridin-2-one
4-[(5-chloro-2-pyridinyl)methoxy]-1-{4-[(2R)-2-(dimethylamino)propoxy]-phenyl}-1H-pyridin-2-one
4-[(5-chloro-2-pyridinyl)methoxy]-1-{4-[(2S)-2-(dimethylamino)propoxy]-phenyl}-1H-pyridin-2-one
4-[(5-chloro-2-pyridinyl)methoxy]-1-{4-[(2R)-2-(1-pyrrolidinyl)propoxy]-phenyl}-1H-pyridin-2-one and
4-[(5-chloro-2-pyridinyl)methoxy]-1-{4-[(2S)-2(1-pyrrolidinyl)-propoxy]phenyl}-1H-pyridin-2-one Group C:
4-benzyloxy-1-{4-[2-(1-pyrrolidinyl)ethoxy]phenyl}-1H-pyridin-2-one
4-fluorobenzyloxy)-1-{4-[2(1-pyrrolidinyl)ethoxy]phenyl}-1H-pyridin-2-one
4-[(5-chloro-2-pyridinyl)methoxy]-1-{4-[2-(1-pyrrolidinyl)ethoxy]phenyl}-1H-pyridin-2-one
4-[(E)-2-(4-fluorophenyl)vinyl]-1-{4-[2-(1-pyrrolidinyl)ethoxy]phenyl}-1H-pyridin-2-one
4-[(E)-2-phenylvinyl]-1-{4-[2-(1-pyrrolidinyl)ethoxy]phenyl}-1H-pyridin-2-one
4-(4-chlorobenzyloxy)-1-{4-[2-(1-pyrrolidinyl)ethoxy]phenyl}-1H-pyridin-2-one
4-(4-fluorobenzyloxy)-1-{4-[2-(1-pyrrolidinyl)ethoxy]phenyl}-1H-pyrimidin-2-one
4-[(5-chloro-2-pyridinyl)methoxy]-1-(4-{[(3R)-1-isopropyl-3-pyrrolidinyl]-oxy}phenyl)-1H-pyridin-2-one
4-[(5-chloro-2-pyridinyl)methoxy]-1-(4-{[(3R)-1-ethyl-3-pyrrolidinyl]oxy}-phenyl)-1H-pyridin-2-one and
4-[(5-chloro-2-pyridinyl)methoxy]-1-(4-{[(3R)-1-methyl-3-pyrrolidinyl]-oxy}phenyl)-1H-pyridin-2-one.

According to the present invention, those compounds represented by a general formula (I-3)

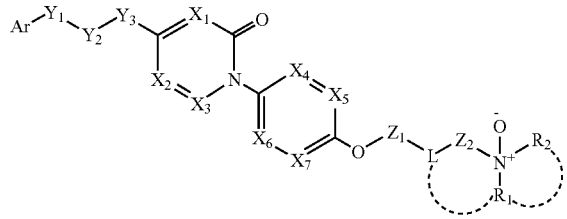

(I-3)

[in the formula,
$R_1, R_2, X_1, X_2, X_3, X_4, X_5, X_6, X_7, Y_1, Y_2, Y_3, L, Z_1, Z_2$ and Ar have the previously given significations] are preferred.

As examples of the compounds represented by the general formula (I-3), the following can be named:
4-benzyloxy-1-{4-[2-(1-oxido-dimethylamino)ethoxy]phenyl}-1H-pyridin-2-one
4-benzyloxy-1-(4-{[(2S)-1-oxido-1-methyl-2-pyrrolidinyl]methoxy}-phenyl)-1H-pyridin-2-one
4-benzyloxy-1-{4-[2-(1-oxido-diethylamino)ethoxy]phenyl}-1H-pyridin-2-one
4-benzyloxy-1-{4-[2-(1-oxido-1-pyrrolidinyl)ethoxy]phenyl}-1H-pyridin-2-one
4-(4-fluorobenzyloxy)-1-{4-[2-(1-oxido-1-pyrrolidinyl)ethoxy]phenyl}-1H-pyridin-2-one
1-{4-[2-(1-oxido-diethylamino)ethoxy]phenyl}-4-(4-fluorobenzyloxy)-1H-pyridin-2-one
4-[(5-chloro-2-pyridinyl)methoxy]-1-{4-[2-(1-oxido-1-pyrrolidinyl)ethoxy]-phenyl}-1H-pyridin-2-one
4-[(E)-2-(4-fluorophenyl)vinyl]-1-{4-[2-(1-oxido-1-pyrrolidinyl)ethoxy]-phenyl}-1H-pyridin-2-one
4-[(E)-2-phenylvinyl]-1-{4-[2-(1-oxido-1-pyrrolidinyl)ethoxy]phenyl}-1H-pyridin-2-one
4-(4-chlorobenzyloxy)-1-{4-[2-(1-oxido-1-pyrrolidinyl)ethoxy]phenyl}-1H-pyridin-2-one
4-(4-fluorobenzyloxy)-1-{4-[2-(1-oxido-1-pyrrolidinyl)ethoxy]phenyl}-1H-pyrimidin-2-one
4-(4-fluorobenzyloxy)-1-{4-[2-(1-oxido-diethylamino)ethoxy]phenyl}-1H-pyrimidin-2-one
4-[(5-chloro-2-pyridinyl)methoxy]-1-{4-[2-(1-oxido-dimethylamino)ethoxy]-phenyl}-1H-pyridin-2-one
4-[(5-chloro-2-pyridinyl)methoxy]-1-{4-[2-(1-oxido-diethylamino)ethoxy]-phenyl}-1H-pyridin-2-one
4-[(5-chloro-2-pyridinyl)methoxy]-1-(4-{2-[1-oxido-ethyl(methyl)amino]-ethoxy}phenyl)-1H-pyridin-2-one
4-[(5-chloro-2-pyridinyl)methoxy]-1-(4-{2-[1-oxido-isopropyl(methyl)amino]-ethoxy}phenyl)-1H-pyridin-2-one
4-(4-fluorobenzyloxy)-1-(4-{2-[1-oxido-isopropyl(methyl)amino]ethoxy}-phenyl)-1H-pyridin-2-one
4-[(5-chloro-2-pyridinyl)methoxy]-1-{4-[(2R)-2-(1-oxido-diethylamino)-propoxy]phenyl}-1H-pyridin-2-one
4-[(5-chloro-2-pyridinyl)methoxy]-1-{4-[(2S)-2-(1-oxido-diethylamino)-propoxy]phenyl}-1H-pyridin-2-one
4-[(5-chloro-2-pyridinyl)methoxy]-1-(4-{[(3R)-1-oxido-1-isopropyl-3-pyrrolidinyl]oxy}phenyl)-1H-pyridin-2-one
4-[(5-chloro-2-pyridinyl)methoxy]-1-(4-{[(3R)-1-oxido-1-ethyl-3-pyrrolidinyl]oxy}phenyl-1H-pyridin-2-one
4-[(5-chloro-2-pyridinyl)methoxy]-1-(4-{[(3R)-1-oxido-1-methyl-3-pyrrolidinyl]oxy}phenyl)-1H-pyridin-2-one
4-[(5-chloro-2-pyridinyl)methoxy]-1-(4-{[(2S)-1-oxido-1-isopropyl-2-pyrrolidinyl]methoxy}phenyl)-1H-pyridin-2-one
4-[(5-chloro-2-pyridinyl)methoxy]-1-(4-{[(2S)-1-oxido-1-methyl-2-pyrrolidinyl]methoxy}phenyl)-1H-pyridin-2-one
4-[(5-chloro-2-pyridinyl)methoxy]-1-(4-{[(2S)-1-oxido-1-ethyl-2-pyrrolidinyl]methoxy}phenyl)-1H-pyridin-2-one
4-[(5-chloro-2-pyridinyl)methoxy]-1-{4-[(2R)-2-(1-oxido-dimethylamino)propoxy]phenyl}-1H-pyridin-2-one
4-[(5-chloro-2-pyridinyl)methoxy]-1-{4-[(2S)-2-(1-oxido-dimethylamino)-propoxy]phenyl}-1H-pyridin-2-one
4-[(5-chloro-2-pyridinyl)methoxy]-1-{4-[(2R)-2-(1-oxido-1-pyrrolidinyl)-propoxy]phenyl}-1H-pyridin-2-one and
4-[(5-chloro-2-pyridinyl)methoxy]-1-{4-[(2S)-2-(1-oxido-1-pyrrolidinyl)-propoxy]phenyl}-1H-pyridin-2-one.

Compounds of the general formula (I) provided by the present invention can be prepared by, for example, the following production processes or those shown in the later appearing working examples, it being understood that the production processes of the compounds of this invention are not limited to these reaction examples.

Production Processes 1
Through reaction of a compound represented by a general formula (II)

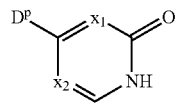

(II)

[in which $x_1$ and $x_2$ are same or different and each stands for optionally substituted methine or nitrogen, $D^P$ signifies a group resented by the following formula (a) or (b)

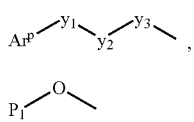
(a)

(b)

wherein $y_1$ stands for single bond, —O—, —NR$^P$—, —S—, —SO— or —SO$_2$—, $y_2$ stands for optionally substituted lower alkylene, optionally substituted lower alkenylene or optionally substituted lower cycloalkylene, $y_3$ stands for single bond, —O—, —NR$^P$—, —S—, —SO— or —SO$_2$—, $R^P$ stands for hydrogen, optionally substituted lower alkyl or a protective group of amino or imino, $Ar^P$ stands for optionally substituted aromatic carbocyclic group, optionally substituted heteroaromatic group or optionally substituted aliphatic carbocyclic group, and $P_1$ stands for a protective group of hydroxyl]

or a salt thereof with a compound of a general formula (III)

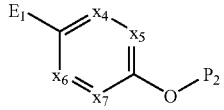
(III)

[in which $x_4$, $x_5$, $x_6$ and $x_7$ are same or different, and each stands for optionally substituted methine or nitrogen, provided that three or more of $x_4$, $x_5$, $x_6$ and $x_7$ do not simultaneously stand for nitrogen, $E_1$ stands for a leaving group, (HO)$_2$B— group or (R$_3$)$_3$Sn— group, wherein $R_3$ stands for $C_1$-$C_8$ alkyl, and $P_2$ stands for a protective group of hydroxyl]

or a salt thereof, a compound represented by a general formula (IV)

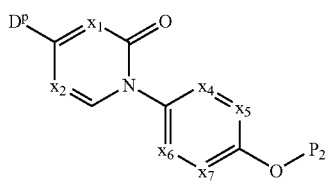
(IV)

[in which $D^P$, $x_1$, $x_2$, $x_4$, $x_5$, $x_6$, $x_7$ and $P_2$ have the previously given significations] can be obtained.

The free hydroxyl compounds or salts thereof which are obtained by removing the protective group $P_1$ from the compounds represented by the general formula (IV) in which $D^P$ is a group expressed by a formula (b), i.e., the compounds represented by a formula (IV-b),

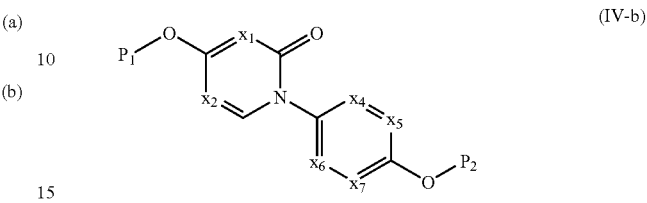
(IV-b)

[in which $x_1$, $x_2$, $x_4$, $x_5$, $x_6$, $x_7$, $P_1$ and $P_2$ have the previously given significations], can be converted to compounds of the above general formula (IV) in which $D^P$ is expressed by the following formula (c)

(c)

[in which $Ar^P$, $y_1$ and $y_2$ have the previously given significations], i.e., the compounds represented by a general formula (IV-c),

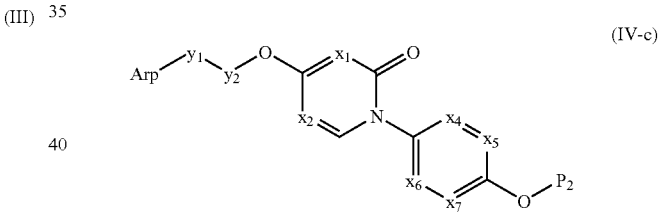
(IV-c)

[in which $Ar^P$, $y_1$, $y_2$, $x_1$, $x_2$, $x_4$, $x_5$, $x_6$, $x_7$ and $P_2$ have the previously given significations]

by first converting the hydroxyl group to a leaving group, if desired, and reacting with compounds of a general formula (V)

(V)

[in which

J stands for hydroxyl or leaving group, and $Ar^P$, $y_1$ and $y_2$ have the previously given significations].

The free hydroxyl compounds or salts thereof which can be obtained by removing protective group $P_2$ from those compounds represented by the general formula (IV) can be converted to the compounds represented by a general formula (VII)

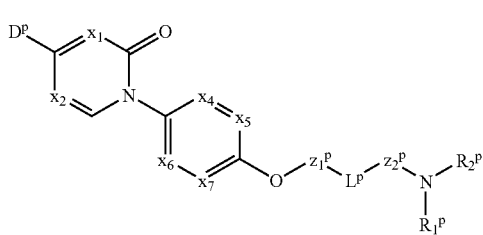

(VII)

[in which
$D^P$, $x_1$, $x_2$, $x_4$, $x_5$, $x_6$, $x_7$, $Z_1^P$, $Z_2^P$, $L^P$, $R_1^P$ and $R_2^P$ have the previously given significations], by converting the hydroxyl group to leaving group where desired, and then reacting them with the compounds represented by a general formula (VI)

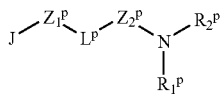

(VI)

[in which
J stands for hydroxyl or leaving group,
$R_1^P$ and $R_2^P$ are same or different and each stands for hydrogen, optionally substituted lower alkyl, optionally substituted lower cycloalkyl, optionally substituted lower alkylcarbonyl, optionally substituted lower alkyloxycarbonyl, or optionally substituted lower alkylsulfonyl; or $R_1^P$ and $R_2^P$ may form an optionally substituted aliphatic nitrogen-containing heterocyclic group together with the nitrogen atom to which they bind;
$Z_1^P$ and $Z_2^P$ may be same or different and each stands for single bond or optionally substituted lower alkylene,
$L^P$ stands for optionally substituted methylene; and $R_1^P$, $L^P$ and $Z_2^P$ may form optionally substituted aliphatic nitrogen-containing heterocyclic group together with the nitrogen atom to which $R_1^P$ binds]

or salts thereof.

The free hydroxyl compounds or salts thereof which are obtained by removing protective group $P_2$ from the compounds represented by the general formula (IV) can be converted to the compounds represented by a general formula (VII-1)

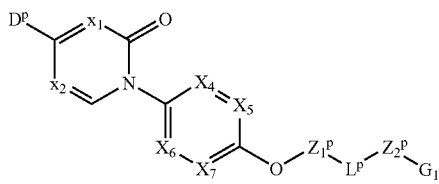

(VII-1)

[in the formula,
$D^P$, $x_1$, $x_2$, $x_4$, $x_5$, $x_6$, $x_7$, $Z_1^P$, $Z_2^P$ and LP have the previously given significations]

by converting the hydroxyl group to leaving group where desired, and then reacting them with the compounds represented by a general formula (VI-1)

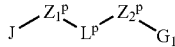

(VI-1)

[in the formula,
J, $Z_1^P$, $Z_2^P$ and $L^P$ have the previously given significations]
or salts thereof.

The compounds represented by the general formula (VII-1) or salts thereof can be converted to the compounds resented by a general formula (VII), by first converting hydroxyl group to leaving group when $G_1$ is hydroxyl and where desire, and thereafter reacting them with compounds represented by a general formula (VI-2)

(VI-2)

[in the formula,
$R_1^P$ and $R_2^P$ have the previously given significations]
or salts thereof.

The compounds resented by the general formula (VII) wherein $R_1^P$ and $R_2^P$ are same or different and at least one of them is hydrogen or salts thereof can be converted to the compounds of the general formula (VII), through reaction with compounds of a general formula (VI-3)

(VI-3)

[in the formula,
$R_2^P$ has the previously given signification, and
$G_2$ either stands for hydroxyl or a leaving group, or may form carbonyl together with $R_2^P$]

or salts or anhydrides thereof.

Where the compounds represented by the general formula (VII) have a group expressed by a formula (b) as $D^P$, i.e., where the compounds are represented by a general formula (VII-b)

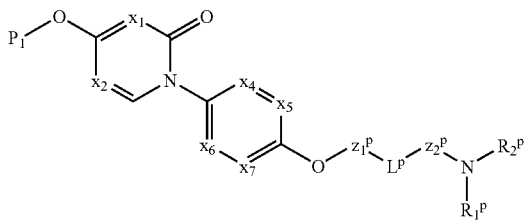

(VII-b)

[in the formula,
$P_1$, $x_1$, $x_2$, $x_4$, $x_5$, $x_6$, $x_7$, $Z_1^P$, $Z_2^P$, $L^P$, $R_1^P$, and $R_2^P$ have the previously given significations], the free hydroxyl compounds or salts thereof as obtained by removing the protective group $P_1$ from the compounds (VII-b) can be converted to those represented by a general formula (VII-c)

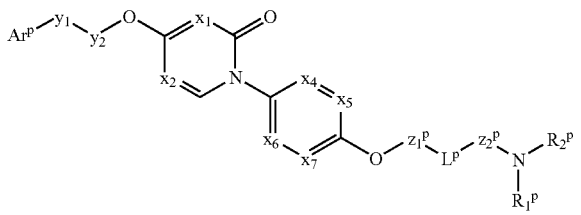

(VII-c)

[in the formula,
Ar$^P$, y$_1$, y$_2$, x$_1$, x$_2$, x$_4$, x$_5$, x$_6$, x$_7$, Z$_1^P$, Z$_2^P$, L$^P$, R$_1^P$ and R$_2^P$ have the previously given significations]

by reaction with the compounds represented by the general formula (V), after optional conversion of the hydroxyl group to leaving group.

Where the compounds represented by the general formula (VII) have a group expressed by a formula (a) as D$^P$, i.e., the compounds represented by the general formula (VII-a)

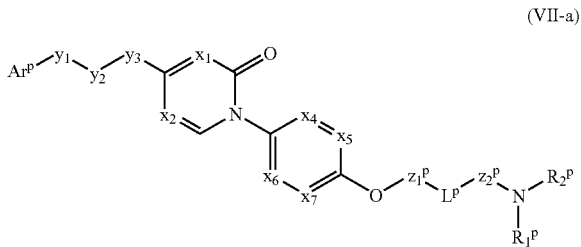

(VII-a)

[in the formula,
Ar$^P$, y$_1$, y$_2$, y$_3$, x$_1$, x$_2$, x$_4$, x$_5$, x$_6$, x$_7$, Z$_1^P$, Z$_2^P$, L$^P$, R$_1^P$ and R$_2^P$ have the previously given significations]

can be converted to the compounds of the general formula (I-1) which is covered by the general formula (I) of the present invention

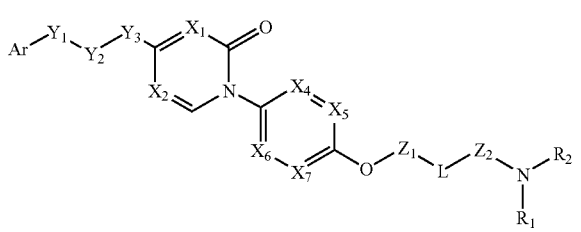

(I-1)

[in the formula,
R$_1$, R$_2$, X$_1$, X$_2$, X$_4$, X$_5$, X$_6$, X$_7$, Y$_1$, Y$_2$, Y$_3$, L, Z$_1$, Z$_2$, and Ar have the previously given significations], upon removing the protective groups from said compounds.

Production process 1 as described in the above concerns methods for producing the compounds within the scope of the general formula (I), in which X$_1$ and X$_2$ are same or different and each stands for optionally substituted methine or nitrogen, and X$_3$ stands for methine; i.e., the compounds represented by the above general formula (I-1).

As the leaving groups represented by J, E$_1$, G$_1$ or G$_2$, for example, halogen such as chlorine, bromine and iodine; organic sulfonyl such as methanesulfonyl, ethanesulfonyl and benzenesulfonyl; and organic sulfonyloxy such as methanesulfonyloxy, trifluoromethanesulfonyloxy and p-toluenesulfonyloxy can be named.

Where functional groups which do not participate in the above reactions, such as amino, imino, hydroxyl, carboxyl, oxo, carbonyl and the like are present in the reactants, these functional groups can be suitably protected with protective groups before the reactions. The protective groups can be removed after the reactions.

Protective groups for amino and imino groups are subject to no particular limitation so long as they have the required function. For example, aralkyl such as benzyl, p-methoxybenzyl, 3,4dimethoxybenzyl, o-nitrobenzyl, p-nitrobenzyl, benzhydril, trityl and the like; lower alkanoyl such as formyl, acetyl, propionyl, butyryl, pivaloyl and the like; benzoyl; arylalkanoyl such as phenylacetyl, phenoxyacetyl and the like; lower alkoxycarbonyl such as methoxycarbonyl, ethoxycarbonyl, propyloxycarbonyl, tert-butoxycarbonyl and the like; aralkyloxycarbonyl such as benzyloxycarbonyl, p-nitrobenzyloxycarbonyl, phenethyloxycarbonyl and the like; lower alkylsilyl such as trimethylsilyl, tert-butyldimethylsilyl and the like; tetrahydropyranyl; trimethylsilylethoxymethyl; lower alkylsulfonyl such as methylsulfonyl, ethylsulfonyl and the like; and arylsulfonyl such as benzenesulfonyl, toluenesulfonyl and the like can be named, acetyl, benzoyl, tert-butoxycarbonyl, trimethylsilylethoxymethyl, methylsulfonyl and the like being particularly preferred.

Hydroxyl-protective groups are subject to no particular limitation so long as they have the required function, examples of which including lower alkyl such as methyl, ethyl, propyl, isopropyl, tert-butyl and the like; lower alkylsilyl such as trimethylsilyl, tert-butyldimethylsilyl and the like; lower alkoxymethyl such as methoxymethyl, 2-methoxyethoxymethyl and the like; tetrahydropyranyl; trimethylsilylethoxymethyl; aralkyl such as benzyl, p-methoxybenzyl, 2,3-dimethoxybenzyl, o-nitrobenzyl, p-nitrobenzyl, trityl and the like; and acyl such as formyl, acetyl and the like. In particular, methyl, methoxymethyl, tetrahydropyranyl, trityl, trimethylsilylethoxymethyl, tert-butyldimethylsilyl and acetyl are preferred.

Carboxyl-protective groups are subject to no particular limitation so long as they have the required function, examples of which including lower alkyl such as methyl, ethyl, propyl, isopropyl, tert-butyl and the like; lower haloalkyl such as 2,2,2-trichloroethyl and the like; lower alkenyl such as 2-propenyl; and aralkyl such as benzyl, p-methoxybenzyl, p-nitrobenzyl, benzhydryl, trityl and the like. In particular, methyl, ethyl, tertbutyl, 2-propenyl, benzyl, p-methoxybenzyl and benzhydryl are preferred.

Oxo- and carbonyl-protective groups are subject to no particular limitation so long as they have the required function, examples of which including acetals and ketals such as ethyleneketal, trimethyleneketal, dimethylketal and the like.

The reaction of a compound of the general formula (II) with a compound of the general formula (III) can be normally conducted using 0.5 mol to molar excess, preferably equimolar to 5 mols excess of the compound (III), per mol of the compound (II).

The reaction is normally conducted in the absence of solvent or in an inert solvent, preferred examples of the inert solvent including methylene chloride, chloroform, tetrahydrofuran, dioxane, dimethylformamide, N-methylpyrrolidone, dimethylsulfoxide, benzene, toluene, nitrobenzene, or mixtures of these solvents.

It is preferred to carry out the reaction in the presence of base. Examples of useful base include amines such as triethylamine, diisopropylethylamine, pyridine, 4-dimethylaminopyridine, tetrabutylammonium fluoride and the like; organic bases such as sodium acetate, potassium acetate, sodium t-butoxide, potassium t-butoxide and the like; and inorganic bases such as sodium hydrogencarbonate, sodium carbonate, potassium carbonate, cesium carbonate, sodium hydroxide, potassium hydroxide, potassium phosphate and the like.

Use rate of the base can normally be equimolar to molar excess, preferably 1-5 mols, per mol of the compound of the general formula (II).

It is also preferred to carry out the reaction in the presence of a metal compound selected from copper compounds and palladium compounds, examples of such metal compounds including copper compounds, e.g., copper (0), copper (I) chloride, copper (II) chloride, copper (I) bromide, copper (II) bromide, copper (I) iodide, copper (II) iodide, copper (I) oxide, copper (II) oxide, copper (II) acetate, copper (II) acetyl acetonate and the like; an palladium compounds, e.g., palladium acetate, dipalladium tris (dibenzylideneacetone) and the like.

Use rate of the metal compound can normally be 0.01 mol to molar excess, preferably 0.05-5 mols, per mol of the compound of the general formula (II).

When a palladium compound is used, the reaction is preferably carried out in the concurrent presence of organophosphorus compound and as the organophosphorus compound, for example, tri-t-butylphosphine, triphenylphosphine, diphenylphosphinoferrocene, 2,2'-bisdiphenylphosphino)1, 1'-binaphthyl and the like can be used.

Use rate of the organophosphorus compound can normally be equimolar to molar excess, preferably 1-3 mols, per mol of the palladium compound used in the reaction.

The suitable reaction temperature normally ranges 0°-300° C., preferably 20°-200° C., and the reaction time can normally ranges 5 minutes to 14 days, preferably from about 2 hours to 7 days.

After termination of the reaction, customary procedures can be applied to give crude product of a compound of the general formula (IV). Thus obtained compound of the general formula (IV) can be used in subsequent reactions after accepted purification or without purification.

The reaction of a free hydroxyl compound or a salt thereof which is obtained by removing protective group $P_1$ from a compound of the general formula (IV-b), or the same compound in which the hydroxyl group is converted to a leaving group, with a compound of the general formula (V) can normally be carried out, using 0.5 mol—molar excess, preferably 0.5-2 mols of the compound (V), per mol of the free hydroxyl compound obtained by removing a protective group $P_1$ from a compound of the general formula (IV-b) or a salt thereof or the same compound in which the hydroxyl group is converted to a leaving group.

The reaction is normally carried out in the absence of a solvent or in an inert solvent, preferred examples of the inert solvent including methylene chloride, chloroform, dichloroethane, carbon tetrachloride, n-heptane, n-hexane, benzene, toluene, xylene, diethyl ether, tetrahydrofuran, 1,4-dioxane, ethylene glycol, dimethyl ether, methyl acetate, ethyl acetate, N,N-dimethylformamide, N-methylpyrrolidone, dimethylsulfoxide or mixed solvents of the foregoing.

Suitable reaction temperature normally ranges −20° C.-200° C., preferably 0°-100° C., and the reaction time can normally be 5 minutes-14 days, preferably from about 30 minutes to 2 days.

Where both of the free hydroxyl compound obtained by removing the protective group $P_1$ from a compound of the general formula (IV-b) or a salt thereof or the same compound in which the hydroxyl group is converted to a leaving group, and the compound of the general formula (V) contain free hydroxyl groups, the reaction is preferably carried out by Mitsunobu Reaction using as a condensing agent, for example, azo compound such as dialkylazodicarboxylate, 1,1'-(azodicarbonyl)diamide and the like; or organophosphorus compound such as triaryl phosphine, trialkylposphine and the like. As the azo compound, for example, dimethylazodicarboxylate, diethylazodicarboxylate, diisopropylazodicarboxylate, di-t-butylazodicarboxylate, dibenzylazodicarboxylate, 1,1'-azodicarbonyl)bis(dimethylamide), 1,1'-(azodicarbonyl)dipiperidide, 1,1'-(azodicarbonyl) dimorpholide and the like can be used, and as the organophosphorus compound, for example, triphenylphosphine, tritolylphosphine, triethylphosphine, tributylphosphine, trioctylphosphine and the like can be used.

Use rate of the azo compound or organophosphorus compound can normally be equimolar to a molar excess, preferably 1-10 mols, per mol of the free hydroxyl compound obtained by removing the protective group $P_1$ from a compound of the general formula (IV-b) or a salt thereof.

Where either of the free hydroxyl compound obtained by removing the protective group $P_1$ from a compound of the general formula (IV-b), or a salt thereof or the same compound in which the hydroxyl group is converted to a leaving group; and the compound of the general formula (V) is a free hydroxyl compound and the other has a leaving group, the reaction is preferably carried out in the presence of a base. Examples of useful base include amines such as trietylamine, diisopropylethylamine, pyridine, 4-dimethylaminopyridine, tetrabutylammonium fluoride and the like; organic bases such as sodium acetate, potassium acetate, sodium t-butoxide, potassium t-butoxide and the like; and inorganic bases such as lithium metal, sodium metal, potassium metal, lithium hydride, sodium hydride, potassium hydride, sodium hydrogencarbonate, sodium carbonate, potassium carbonate, cesium carbonate, sodium hydroxide, potassium hydroxide, potassium phosphate and the like.

Use rate of the base can normally be 0.5 mol to molar excess, preferably 1-1.5 mols, per mol of the free hydroxyl compound obtained by removing a protective group $P_1$ from a compound of the general formula (IV-b) or a salt thereof or the same compound in which the hydroxyl group is converted to a leaving group.

After termination of the reaction, customary processing can be conducted to provide crude product of a compound represented by the general formula (IV-a).

The reaction of a free hydroxyl compound obtained by removing the protective group $P_2$ from a compound of the general formula (IV) or a salt thereof or the same compound in which the hydroxyl group is converted to a leaving group, with a compound of the general formula (VI) or (VI-1) can be carried out under the conditions similar to those of the previously described reaction between a free hydroxyl compound which is obtained by removing the protective group $P_1$ from a compound of the general formula (IV-b) or a salt thereof or the same compound in which the hydroxyl group is converted to a leaving group, with a compound of the general formula (V), to provide a crude product of the corresponding compound of the general formula (VII).

The reaction of a compound of the general formula (VII-1) or a salt thereof or, when the compound's $G_1$ is hydroxyl, the same compound in which the hydroxyl is converted to a leaving group where desired, with a compound of the general formula (VI-2) can normally be conducted using 0.5 mol to molar excess, preferably 0.5-5 mols of the compound of the general formula (VI-2) per mol of the compound of the general formula (VII-1) or a salt thereof or the compound whose $G_1$ is hydroxyl group which may have been converted to a leaving group.

The reaction is normally carried out in the absence of a solvent or in an inert solvent, preferred examples of the inert solvent including water, methanol, ethanol, n-propanol, methylene chloride, chloroform, dichloroethane, carbon tetrachloride, n-heptane, n-hexane, benzene, toluene, xylene, diethyl ether, tetrahydrofuran, 1,4-dioxane, ethylene glycol, dimethyl ether, methyl acetate, ethyl acetate, acetonitrile, N,N-dimethylformamide, N-methylpyrrolidone, dimethylsulfoxide or mixed solvents of the foregoing.

Suitable reaction temperature normally ranges –20°-200° C., preferably 0°-100° C., and the reaction time can normally be 5 minutes-14 days, preferably from about 30 minutes to 2 days.

Where the compound of the general formula (VII-1) in which $G_1$ is hydroxyl and the hydroxyl has been converted to a leaving group, or a salt thereof, is used, the reaction can be carried out in the presence or absence of a base. As the base, for example, inorganic bases such as lithium metal, sodium metal, potassium metal, lithium hydride, sodium hydride, potassium hydride, sodium hydrogencarbonate, sodium carbonate, potassium carbonate, cesium carbonate, sodium hydroxide, potassium hydroxide, potassium phosphate and the like can be used.

The use rate of the base can normally be 0.5 mol to a molar excess, preferably 1-2 mols, per mol of the compound of the general formula (VII-1) or a salt thereof Where the compound of the general formula (VII-1) or a salt thereof or the same compound whose $G_1$ is hydroxyl group which may have been converted to a leaving group if desired, contains carbonyl group, the reaction can be conducted in the presence of a reducing agent. As the reducing agent, for example, lithium borohydride, sodium borohydride, potassium borohydride, cesium borohydride, tetramethylammonium borohydride, tetraethylammonium borohydride, tetra-n-butylammonium borohydride, sodium cyanoborohydride, tetra-n-butylammonium cyanoborohydride, sodium triacetoxyborohydride, tetramethylammonium triacetoxyborohydride, borane-diethylsulfide complex, borane-pyridine complex, borane-tetrahydrofuran complex, borane-N,N-diethylaniline complex and the like can be used.

The use rate of the reducing agent can normally range 0.5 mol—a molar excess, preferably 1-10 mols, per mol of the compound of the general formula (VII-1) or a salt thereof or the compound whose $G_1$ is hydroxyl which may have been converted to a leaving group where desire.

The above reaction can also be conducted in the presence or absence of an acid. As the acid, for example, protonic acids such as acetic acid, trifluoroacetic acid, citric acid, methanesulfonic acid, toluenesulfonic acid, hydrochloric acid, hydrobromic acid, sulfuric acid and the like; and Lewis acids such as zinc dichloride, zinc dibromide, zinc diiodide, titanium tetrachloride, tetraisopropoxytitanium, tetra-n-butylammonium chloride and the like can be used.

The use rate of the acid can normally range 0.5 mol—a molar excess, preferably 1-10 mols, per mol of the compound of the general formula (VII-1) or a salt thereof or the compound whose $G_1$ is hydroxyl which may have been converted to a leaving group if desired Where the compound of the general formula (VII-1) or a salt thereof contains hydroxyl, the reaction is preferably conducted, for example, by Mitsunobu Reaction using as a condensing agent, azo compound such as dialkylazodicarboxylate, 1,1'-(azodicarbonyl)diamide and the like; or organophosphorus compound such as triarylphosphine, trialkylposhine and the like. As the azo compound, for example, dimethylazodicarboxylate, diethylazodicarboxylate, diisopropylazodicarboxylate, di-t-butylazodicarboxylate, di-benzylazodicarboxylate, 1,1'-(azodicarbonyl)bis (dimethylamide), 1,1'-(azodicarbonyl)dipiperidide, 1,1'-(azodicarbonyl)dimorpholide and the like can be used, and as the organophosphorus compound, for example, triphenylphosphine, tritolylphosphine, triethylphosphine, tributylphosphine, trioctylphosphine and the like can be used.

Use rate of the azo compound or organophosphorus compound can normally be equimolar to a molar excess, preferably 1-10 mols, per mol of the compound of the general formula (VII-1) or a salt thereof After termination of the reaction, customary processing can be conducted to provide crude product of a compound of the general formula (VII).

The reaction of a compound of the general formula (VII) in which $R_1^P$ and $R_2^P$ are same or different and at least one of them is hydrogen, or a salt thereof, with a compound of the general formula (VI-3) or a salt thereof, can normally be conducted by using 0.5 mol—a molar excess, preferably 0.5 mol-5 mols, of the compound of the general formula (VI-3), per mol of the compound of the general formula (VII) in which $R_1^P$ and $R_2^P$ are same or different and at least one of them is hydrogen, or a salt thereof.

The reaction is normally carried out in the absence of a solvent or in an inert solvent, preferred examples of the inert solvent including water, methanol, ethanol, n-propanol, methylene chloride, chloroform, dichloroethane, carbon tetrachloride, n-heptane, n-hexane, benzene, toluene, xylene, diethyl ether, tetrahydrofuran, 1,4-dioxane, ethylene glycol, dimethyl ether, methyl acetate, ethyl acetate, acetonitrile, N,N-dimethylformamide, N-methylpyrrolidone, dimethylsulfoxide or mixed solvents of the foregoing.

Suitable reaction temperature normally ranges –20°-200° C., preferably 0°-100° C., and the reaction time can normally be 5 minutes-14 days, preferably from about 30 minutes to 2 days.

Where the compound of the general formula (VI-3) has a leaving group, the reaction can be carried out in the presence or absence of a base. As the base, for example, inorganic bases such as lithium metal, sodium metal, potassium metal, lithium hydride, sodium hydride, potassium hydride, sodium hydrogencarbonate, sodium carbonate, potassium carbonate, cesium carbonate, sodium hydroxide, potassium hydroxide, potassium phosphate and the like can be used.

The use rate of the base can normally be 0.5 mol to a molar excess, preferably 1-2 mols, per mol of the compound of the general formula (VII) in which $R_1^P$ and $R_2^P$ are same or different and at least one of them is hydrogen, or a salt thereof.

Where the compound of the general formula (VI-3) contains carbonyl group, the reaction can be carried out in the presence of a reducing agent As the reducing agent, for example, lithium borohydride, sodium borohydride, potassium borohydride, cesium borohydride, tetramethylammonium borohydride, tetraethylammonium borohydride, tetra-n-butylammonium borohydride, sodium cyanoborohydride, tetra-n-butylammonium cyanoborohydride, sodium triacetoxyborohydride, tetramethylammonium triacetoxyborohydride, borane-dimethylsulfide complex, borane-pyridine complex, borane-tetrahydrofuran complex, borane-N,N-diethylaniline complex and the like can be used.

The use rate of the reducing agent can normally range 0.5 mol—a molar excess, preferably 1-10 mols, per mol of the compound of the general formula (VII) in which $R_1^P$ and $R_2^P$ are same or different and at least one of them is hydrogen, or a salt thereof.

The above reaction can also be conducted in the presence or absence of an acid. As the acid, for example, protonic acids such as acetic acid, trifluoroacetic acid, citric acid, methanesulfonic acid, toluenesulfonic acid, hydrochloric acid, hydrobromic acid, sulfuric acid and the like; and Lewis acids such as zinc dichloride, zinc dibromide, zinc diiodide, titanium tetrachloride, tetraisopropoxytitanium, tetra-n-butylammonium chloride and the like can be used.

The use rate of the acid can normally range 0.5 mol—a molar excess, preferably 1-10 mols, per mol of the compound of the general formula (VII) in which $R_1^P$ and $R_2^P$ are same or different and at least one of them is hydrogen, or a salt thereof.

Where the compound of the general formula (VI-3) or a salt thereof contains hydroxyl, the reaction is preferably carried out by Mitsunobu Reaction using as a condensing agent, for example, azo compound such as dialkylazodicarboxylate, 1,1'-(azodicarbonyl)diamide and the like; or organophosphorus compound such as triarylphosphine, trialkylphosphine and the like. As the azo compound, for example, dimethylazodicarboxylate, diethylazodicarboxylate, diisopropylazodicarboxylate, di-t-butylazodicarboxylate, dibenzylazodicarboxylate, 1,1'-(azodicarbonyl)bis(dimethylamide), 1,1'-(azodicarbonyl)dipiperidide, 1,1'-(azodicarbonyl)dimorpholide and the like can be used, and as the organophosphorus compound, for example, triphenylphosphine, tritolylphosphine, triethylphosphine, tributylphosphine, trioctylphosphine and the like can be used.

Use rate of the azo compound or organophosphorus compound can normally be equimolar to a molar excess, preferably 1-10 mols, per mol of the compound of the general formula (VI-3) or a salt thereof.

Where $D^P$ of a compound of the general formula (VII) is a group represented by the formula (b), i.e., where the compound is covered by the general formula (VII-b), the reaction of the free hydroxyl compound as obtained by removing the protective group $P_1$ or salt thereof or the same compound in which the hydroxyl group is converted to a leaving group, with a compound of the general formula (V) can be carried out under the conditions similar to those of the previously described reaction between a flee hydroxyl compound which is obtained by removing the protective group $P_1$ from a compound of the general formula (IV-b) or a salt thereof or the same compound in which the hydroxyl group is converted to a leaving group, with a compound of the general formula (V), to provide compound of the general formula (VII-c).

Where $D^P$ of a compound of the general formula (VII) is a group represented by the formula (a), i.e., where the compound is covered by the general formula (VII-a), the compound can be optionally purified by customarily practiced means and then subjected to reactions for removing protective groups of amino, hydroxyl, carboxyl, oxo and carbonyl groups in suitable combination, to provide the corresponding compound of the general formula (I-1).

Means for removing protective groups differ depending on kind of the protective groups and stability of individual compounds represented by the general formula [I-1]. For example, the removal is conducted following those methods described in literature [cf. Protective Groups in Organic Synthesis, T. W. Greene, John Wiley & Sons (1981)] or those analogous thereto, by solvolysis using acid or base, i.e., a method of having, for example, from 0.01 mol to a large molar excess of acid, preferably trifluoroacetic acid, formic acid, hydrochloric acid or the like; or from equimolar to a large molar excess of base, preferably potassium hydroxide, calcium hydroxide or the like, act on the object compound, chemical reduction using hydrogenated metal complex or by catalytic reduction using palladium-carbon catalyst or Raney nickel catalyst.

Production Process 2

A compound of a general formula (XIII)

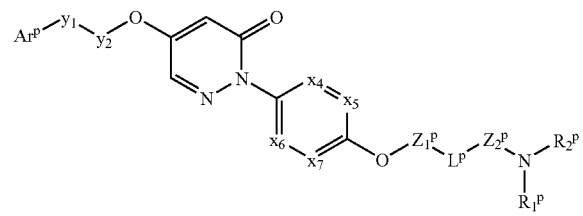

(XIII)

[in the formula, $Ar^P$, $x_4$, $x_5$, $x_6$, $x_7$, $y_1$, $y_2$, $R_1^P$, $R_2^P$, $L^P$, $Z_1^P$ and $Z_2^P$ have the previously given significations]

can be prepared through the steps of reacting a compound of a general formula (VII)

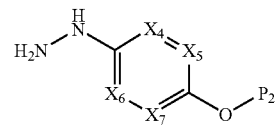

(VIII)

[in the formula, $x_4$, $x_5$, $x_6$, $x_7$ and $P_2$ have the previously given significations]

or a salt thereof with mucobromic acid to form a compound of a general formula (IX)

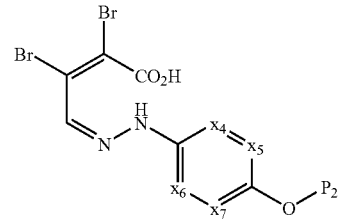

(IX)

[in the formula, $x_4$, $x_5$, $x_6$, $x_7$ and $P_2$ have the previously given significations];

then converting it to a compound of a general formula (X)

(X)

[in the formula,
$x_4$, $x_5$, $x_6$, $x_7$ and $P_2$ have the previously given significations]

by intramolecular cyclizing reaction; reacting the same with compound of the general formula (V-a)

(V-a)

[in the formula,
$Ar^P$, $y_1$ and $y_2$ have the previously given significations]

or a salt thereof to convert it to a compound of the general formula (XI)

(XI)

[in the formula,
$Ar^P$, $x_4$, $x_5$, $x_6$, $x_7$, $y_1$, $y_2$ and $P_2$ have the previously given significations];

then reducingly removing the bromine atom therefrom to convert it to a compound of a general formula (XII)

(XII)

[in the formula,
$Ar^P$, $x_4$, $x_5$, $x_6$, $x_7$, $y_1$, $y_2$ and $P_2$ have the previously given significations];

removing the protective group $P_2$; and reacting the resulting free hydroxyl compound or a salt thereof, after optionally converting the hydroxyl group to a leaving group, with a compound of the general formula (VI) or a salt thereof Said free hydroxyl compound or the salt thereof as obtained by removing the protective group $P_2$ from the compound of the general formula (XII) can be converted to the corresponding compound of a general formula (XII-1)

(XIII-1)

[in the formula,
$x_4$, $x_5$, $x_6$, $x_7$, $y_1$, $y_2$, $Ar^P$, $G_1$, $Z_1^P$, $Z_2^P$ and $L^P$ have the previously given significations], through the steps of optionally converting the hydroxyl group to a leaving group, and then reacting it with a compound of the general formula (VI-1) or a salt thereof.

A compound of the general formula (XIII-1) or a salt thereof can be converted to the corresponding compound of the general formula (XIII), through the steps of optionally converting hydroxyl group to a leaving group when $G_1$ is hydroxyl, and then reacting it with a compound of the general formula (VI-2) or a salt thereof.

A compound of the general formula (XII) in which $R_1^P$ and $R_2^P$ are same or different and at least one of them is hydrogen, or a salt thereof, can be converted to a compound of the general formula (XIII) in which $R_1^P$ and $R_2^P$ are same or different and at least one of them is not hydrogen, through reaction with a compound of the general formula (VI-3) or a salt or an acid anhydride thereof.

By removing protective groups from compounds of the general formula (XIII), compounds represented by a general formula (I-2)

(I-2)

[in the formula,
Ar, $X_4$, $X_5$, $X_6$, $X_7$, $Y_1$, $Y_2$, $R_1$, $R_2$, L, $Z_1$, and $Z_2$ have the previously given significations]

belonging to the given general formula of the present invention can be prepared.

Production process 2 as described in the above is a process for preparing, among the compounds of the general formula (I), those in which both $X_1$ and $X_2$ are unsubstituted methane, $X_3$ is nitrogen and $Y_3$ is oxygen, i.e., the compounds of above formula (I-2).

The reaction of mucobromic acid with a compound of the general formula (VIII) can normally be conducted using 0.5 mol—a molar excess, preferably equimolar to 10 mols, of the compound of the general formula (VIII), per mol of mucobromic acid.

The reaction is normally carried out in solvent, examples of preferred solvent being water, methanol, ethanol, propanol, butanol, pentanol, 1,4-dioxane, dimethoxyethane, dimethylformamide, N-methylpyrrolidone, dimethylsulfoxide, benzene, toluene, xylene and mixed solvents of the foregoing.

The above reaction can also be carried out in the presence or absence of base or acid, examples of the base including organic bases such as triethylamine, diisopropylethylamine, pyridine, 4-dimethylaminopyridine and the like or inorganic bases such as sodium hydrogencarbonate, sodium carbonate, potassium carbonate, cesium carbonate, sodium hydroxide, potassium hydroxide and the like; and examples of the acid including protonic acids such as acetic acid, trifluoroacetic acid, methanesulfonic acid, toluenesulfonic acid, hydrochloric acid, hydrobromic acid, sulfuric acid, phosphoric acid and the like and Lewis acids such as zinc dichloride, titanium tetrachloride, scandium trifluoromethanesulfonate, ytterbium trifluoromethanesulfonate, lanthanum trifluoromethanesulfonate and the like.

The use rate of the base or acid can normally be 0.01 mol—a molar excess, preferably 0.1-5 mols, per mol of mucobromic acid.

Suitable reaction temperature normally ranges 0°-300° C., preferably 20°-200° C., and the reaction time can normally be 5 minutes-7 days, preferably 30 minutes-about 24 hours.

After termination of the reaction, the reaction product is given customary post-treatment to provide a crude product of the compound of the general formula (IX), which is useful for subsequent reaction with or without intervening purification.

The intramolecular ring-closing reaction of a compound of the general formula (IX) is normally carried out in solvent, examples of preferred solvent being water, methanol, ethanol, propanol, butanol, pentanol 1,4-dioxane, dimethoxyethane, dimethylformamide, N-methylpyrrolidone, dimethylsulfoxide, benzene, toluene, xylene and mixed solvents of the foregoing.

It is preferred to conduct the reaction in the presence of an acid, examples of the acid including protonic acids such as acetic acid, trifluoroacetic acid, methanesulfonic acid, toluenesulfonic acid, hydrochloric acid, hydrobromic acid, sulfuric acid, phosphoric acid and the like and Lewis acids such as zinc dichloride, titanium tetrachloride, scandium trifluoromethanesulfonate, ytterbium trifluoromethanesulfonate, lanthanum trifluoromethanesulfonate and the like.

The use rate of the acid can normally be 0.01 mol—a molar excess, per mol of the compound of the general formula (IX).

Suitable reaction temperature normally ranges 0°-300° C., preferably 20°-200° C., and the reaction time can normally be 5 minutes-7 days, preferably 30 minutes-about 24 hours.

After termination of the reaction, the reaction product is given customary post-treatment to provide a crude product of the compound of the general formula (X), which is useful for subsequent reaction with or without intervening purification.

The reaction of a compound of the general formula (X) with a compound of the general formula (V-a) can be carried out under the conditions similar to those used for the reaction of free hydroxyl compound resulting from removing protective group $P_1$ from a compound of the general formula (IV-b) or a salt thereof or the same compound in which the hydroxyl is converted to a leaving group, with a compound of the general formula (V), wherein either of the free hydroxyl compound as obtained by removing the protective group $P_1$ from the compound of the general formula (IV-b) or a salt thereof or the same compound in which the hydroxyl is converted to a leaving group, or the compound of the general formula (V) is free hydroxyl compound and the other has a leaving group, to provide a crude product within a scope of the general formula (XI). Thus obtained compound of the general formula (X) can be used for the subsequent reaction with or without intervening purification.

The reaction of a free hydroxyl compound obtained by removing the protective group $P_2$ from a compound of the general formula (XI) or a salt thereof or the same compound in which the hydroxyl group is converted to a leaving group, with a compound of the general formula (VI) can be carried out under the conditions similar to those of the previously described reaction between a free hydroxyl compound which is obtained by removing the protective group $P_1$ from a compound of the general formula (IV-b) or a salt thereof or the same compound in which the hydroxyl group is converted to a leaving group, with a compound of the general formula (V), to provide a compound of the general formula (XIII).

The reaction of a free hydroxyl compound obtained by removing the protective group $P_2$ from a compound of the general formula (IV) or a salt thereof or the same compound in which the hydroxyl group is converted to a leaving group, with a compound of the general formula (VI-1) or a salt thereof can be carried out under the conditions similar to those of the previously described reaction between a free hydroxyl compound which is obtained by removing the protective group $P_1$ from a compound of the general formula (IV-b) or a salt thereof or the same compound in which the hydroxyl group is converted to a leaving group, with a compound of the general formula (V), to provide a crude product of the corresponding compound of the general formula (XIII-1).

The reaction of a compound of the general formula (XIII-1) or a salt thereof or, when the compound's $G_1$ hydroxyl, the same compound in which the hydroxyl is converted to a leaving group where desired, with a compound of the general formula (VI-2) or a salt thereof can be carried out under the conditions similar to those of the previously described reaction between a compound of the general formula (VII-1) or a salt thereof or, when the compound's $G_1$ is hydroxyl, the same compound in which the hydroxy is converted to a leaving group where desired, with a compound of the general formula (VI-2), to provide a crude product of the corresponding compound of the general formula (XIII).

The reaction of a compound of the general formula (XIII) in which $R_1^P$ and $R_2^P$ are same or different and at least one of them is hydrogen, or a salt thereof, with a compound of the general formula (VI-3) or a salt or acid anhydride thereof can be carried out under the conditions similar to those of the reaction of a compound of the general formula (VII) in which $R_1^P$ and $R_2^P$ are same or different and at least one of them is hydrogen, with a compound of the general formula (VI-3) or a salt or acid anhydride thereof, to provide a compound of the general formula (XIII) in which $R_1^P$ and $R_2^P$ are same or different and at least one of them is not hydrogen.

The compounds of the general formula (XIII) are subjected to customary post-treatment with or without preceding purification or, when the reaction product contains protective groups, after removal of the protective groups and when the product contains no protective group, with no intervening treatment, to provide the corresponding compounds of the general formula (I-2).

Removal of protective groups and post-treatments can be conducted following the methods as described in the explanation of the Production process 1.

Thus obtained compounds of the general formula (I-1) or (I-2) can be easily isolated and purified by ordinary separation means, for example, solvent extraction, recrystallization, column chromatography, preparative thin layer chromatography and the like.

These compounds can be converted to pharmaceutically acceptable salts or esters according to accepted practice. Conversely, conversion of such salts or esters to free compounds can be done accordingly to accepted practice.

In the Production processes 1 and 2, mucobromic acid and compounds of the general formulae (II), (III), (IV), (V), (VI), (VI-1), (VI-2), (VI-3), (VII), (VIII), (IX), (X), (XI), (XII) and (XIII) which are used as the starting materials are either commercially available or can be prepared by adequately combining methods known per se or those analogous thereto or those described in the later appearing Examples where necessary.

Salts of compounds of the general formulae (II), (III), (IV), (V), (VI), (VI-1), (VI-2), (VI-3), (VII), (VIII), (IX), (X), (XI), (XII) and (XIII) are subject to no particular limitation so long as they do not adversely affect the reactions. As examples of the salts, where the compounds have, for example, carboxyl groups, base addition salts at the carboxyl groups; or where the compounds have amino or basic heterocyclic groups, acid addition salts at the amino or basic heterocyclic groups can be named.

As such base addition salts, for example, alkali metal salt such as sodium salt potassium salt and the like; alkaline earth metal salt such as calcium salt magnesium salt and the like; ammonium salt and organic amine salts such as trimethylamine salt triethylamine salt dicyclohexylamine salt ethanolamine salt diethanolamine salt triethanolamine salt, procaine salt, N,N'-dibenzylethylenediamine salt and the like can be named. As the acid addition salts, for example, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonates such as methanesulfonate, isethionate, benzenesulfonate, p-toluenesulfonate and the like can be named.

Activities of those compounds represented by the general formula (I) of the present invention as MCH receptor antagonists are verified, for example, by the following pharmacological test examples.

PHARMACOLOGICAL TEST EXAMPLE 1

(MCH Binding Inhibition Test)

A human MCH-1R encoding cDNA sequence [FEBS Letters, Vol. 398, p. 253 (1996); Biochimica et Biophisica Acta, Vol. 1401, p. 216 (1998)) was cloned to plasmid vector pEF/myc/cyto (Invitrogen Corporation). The obtained expression vector was transfected to a host cell CHO-K1 (American Type Culture Collection) using Lipofectamine Plus Reagent (Life Technology Inc.) to provide MCH-1R expression cells.

Membrane samples eared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through Glass Filter GF/C (Wattman Co.). After washing the glass filter with 50 mM Tris buffer (pH7.4) comprising 10 mM magnesium chloride, 2 mM ethylenediamine tetraacetate and 0.04% Tween-20, radiative activity on the glass filter was measured. Non-specific binding was measured in the presence of 1 μM human MCH and 50% inhibition concentration ($IC_{50}$ value) of each test compound to specific [$^{125}$I] MCH binding was determined. The results were as shown in Table 2.

TABLE 2

| Test Compound | $IC_{50}$(nM) |
| --- | --- |
| Example 1 | 9.5 |
| Example 2 | 4.4 |
| Example 5 | 3.8 |
| Example 12 | 5.8 |
| Example 18 | 4.3 |
| Example 19 | 5.1 |
| Example 21 | 2.9 |
| Example 23 | 5.2 |
| Example 28 | 4.9 |
| Example 29 | 5.6 |
| Example 30 | 4.8 |
| Example 32 | 3.5 |
| Example 45 | 1.5 |
| Example 53 | 4.4 |
| Example 68 | 4.5 |
| Example 73 | 7.0 |
| Example 75 | 4.2 |
| Example 81 | 7.8 |
| Example 86 | 1.9 |
| Example 90 | 2.7 |
| Example 91 | 3.5 |
| Example 92 | 8.8 |
| Example 101 | 5.4 |
| Example 114 | 5.4 |
| Example 115 | 5.5 |
| Example 124 | 6.8 |
| Example 133 | 4.7 |
| Example 134 | 8.6 |

As above, compound of the present invention potently inhibited binding of MCH to MCH-1R and acted as MCH-1R antagonist

PHARMACOLOGICAL TEST EXAMPLE 2

(Brain/Cerebrospinal Fluid Migration Test)

A test compound was orally or intravenously administered to SD male rats (7 to 10 weeks-age, 200 to 400 g). Under anesthesia with ether for a predetermined period of time, from each of the rats whole blood was collected from its abdominal aorta using a heparin-processed syringe. Thereafter the brain skin was cut open and a 30 G needle for dental use was pierced between the cervical vertebrae and inserted into the subarachnoid cavity. Through the tube connected with the dental 30 G needle, 50-100 μL of the cerebrospinal fluid was collected into a 1-mL syringe, and then the brain was taken out. Each blood sample was centrifuged (4° C., 6,000 rpm,10 minutes) and the resulting plasma was stirred with three-fold the amount thereof of ethanol (including an internal standard substance). The brain sample was added with 2 mL of water and homogenized, a part of which was taken and stirred with three-fold the amount thereof of ethanol (including an internal standard substance). The cerebrospinal fluid was stirred with three-fold the amount thereof of ethanol (including an internal standard substance). Those samples were allowed to stand for 20 minutes at −20° C., and then centrifuged (4° C., 12,000 g, 10 minutes). The supernatant was analyzed through LC/MS/MS, and the concentration levels of the test compound in the plasma, in the brain and in the cerebrospinal fluid were quantified according to a relative calibration curve method.

In consequence, after 2 hours of oral administration (10 mg/kg), the brain concentration of the compound of Example 1 was 2.33 nmol/g, its cerebrospinal fluid concentration was 0.046 μM and its plasma concentration was 0.25 μM.

PHARMACOLOGICAL TEST EXAMPLE 3

(Internal Kenetics Test)

A test compound was orally or intravenously administered to SD male rats (7 to 10 weeks-age, 200 to 400 g) which had fasted overnight, and within a predetermined period of time, about 100 μL of the blood per rat was collected via the tail vein, using a heparinized capillary. The blood was centrifuged (4° C., 6,000 rpm, 10 minutes) to provide plasma. To the plasma tree-fold the amount thereof of ethanol (including an internal standard substance) was added and stored, followed by standing at −20° C. for 20 minutes and then centrifuge (4° C., 10,000 rpm, 10 minutes). The supernatant was analyzed through LC/MS/MS, and the plasma concentration of the test compound was quantified according to a relative calibration curve method. In consequence, the compound of Example 29 showed a bioavailability of 79% and the half-value period in blood of 3.9 hours.

As above, compounds of the present invention potently inhibited binding of MCH to MCH-1R and acted as MCH-1R antagonist.

Therefore, compounds of the present invention are useful as preventing, treating or therapeutic agents for various diseases associated with MCH, such as metabolic disorders represented by obesity, diabetes, hormone disorder, hyperlipidemia, gout, fatty liver and the like; cardiovascular disorders represented by stenocardia, acute or congestive heart failure, myocardial infarction, coronary atherosclerosis, hypertension, renal diseases and electrolyte abnormality, central nervous system or peripheral nervous system disorders represented by bulimia, emotional disturbance, depression, anxiety, epilepsy, delirium, dementia, schizopherenia, attention-deficit hyperactivity disorder, memory impairment, sleep disorders, cognitive failure, dyskinesia, paresthesias, smell disorders, morphine tolerance, drug dependence and alcoholism, reproductive disorders represented by infertility, preterm labor and sexual dysfunction; digestive disorders; respiratory disorders; and cancer or pigmentation.

Those compounds of the present invention can be administered orally or parenterally, and when formulated into preparation forms adapted for administration, can provide preventing, treating or therapeutic agents for diseases as named in the above.

In the occasions of actual clinical use of the compounds of the present invention, they can be normally formulated into various forms of preparation with addition of pharmaceutically acceptable adjuvants according to the mode of administration, and thereafter administered. As adjuvants in such occasions, various additives heretofore known in the field of medical preparations can be used, specific examples of which include gelatine, lactose, sucrose, titanium dioxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropylcyclodextrin and the like.

As the preparation forms formulated using these adjuvants, for example, solid preparations such as tablet, capsule, granule, powder or suppository; and liquid preparations such as syrup, elixir, or injection and the like can be named, which can be prepared following customary methods in the field of medical preparations. Furthermore, liquid preparations may take such a form as to be dissolved or suspended in water or in other suitable medium immediately before use. Particularly, injections can be dissolved or suspended in physiological saline solution or glucose solution where necessary, and buffer or preservative may further be added thereto.

Those preparations can contain the compounds of the present invention at a rate of 1-100% by weight, preferably 1-60% by weight, based on individual pharmaceutical preparation. These preparations may also contain other therapeutically active compounds.

In case of using the compounds of the present invention as preventing, treating or therapeutic agents of said diseases, their dosage and administration frequency differ depending on sex, age, body weight and seriousness of symptoms of individual patients and the kind and scope of intended therapeutic effect. Whereas, generally normal dosage can be 0.001-50 mg per day per kg body weight, which can be administered in single time or in plural times. Preferably the dosage ranges about 0.01-about 25 mg/kg per day, inter alia, about 0.05-about 10 mg/kg per day.

The compounds of the present invention can be used in combination with drugs effective for hypertension, obesity-associated hypertension, hypertension-associated diseases, cardiac hypertrophy, left ventricular hypertrophy, metabolic disorder, obesity, obesity-associated diseases and the like (hereafter referred to as "drug for combined use"). Such drugs can be administered simultaneously, separately or in succession, for prevention or treatment of above-named diseases. When a compound of the present invention is used simultaneously with one, two or more of drugs for combined use, they may be formulated into a medical preparation suited for single administration form. Whereas, in combination therapy, a composition containing the compound of the present invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to individual object of medication, administration route, specific disease, combination of drugs, and the like. Form of administering drug(s) for combined use is not critical but it is sufficient that the compound of the present invention is combined with selected drug(s) for at the time of administration.

As adoptable administration forms, for example, 1) administration of single preparation obtained by simultaneously formulating a compound of the present invention and drug(s) for combined use, 2) simultaneous administration of two kinds of preparations obtained by separately formulating a compound of the present invention and drug(s) for combined use, via a same administration route, 3) administration at a certain time interval, via a same administration route, of two kinds of preparations obtained by separately formulating a compound of the present invention and drug(s) for combined use, 4) simultaneous administration of two kinds of preparations obtained by separately formulating a compound of the present invention and drug(s) for combined use, via different administration routes, and 5) administration of two kinds of preparations obtained by separately formulating the compound of the present invention and drug(s) for combined use, via different administration routes, at a certain time interval (e.g., administration by the order of the compound of the present invention and then the drug(s) for combined use, or by the reversed order) can be adopted. The use ratio of a compound of the present invention and drug(s) for combined use can be suitably selected, according to individual object of medication, administration route, disease and the like.

As drugs for combined use which can be used in the present invention, for example, those for treating diabetes, hyperlipidemia, hypertension, obesity and the like can be named. Two or more of such drugs for combined use may be combined at an adequate ratio and used.

As drug for treating diabetes, for example, 1) PPAR γ agonists such as glitazones [e.g., ciglitazone, darglitazone, englitazone, isaglitazone (MCC-555) and the like], pioglitazone, rosiglitazone, troglitazone, BRL49653, CLX-0921, 5-BTZD, GW-0207, LG-100641, LY-300512 and the like; 2) biganides such as metformin, buformin, phenformin and the like; 3) protein tyrosine phosphatase-1B inhibitor, 4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like; 5) meglitinides such as repaglinide, nateglinide and the like; 6) α-glucosidehydroxylase inhibitors such as acarbose, adiposine, camiglibose, emiglitate, miglitol, voglibose, pradimicin-Q, salbostatin, CKD-711, MDL-25,673, MDL-73,945, MOR 14 and the like; 7) α-amylase inhibitors such as tendamistat, trestatin, A1 3688 and the like; 8) insulin secretion promoters such as linogliride, A-4166 and the like; 9) fatty acid oxidation repressors such as clomoxir, etomoxir and the like; 10) A2 antagonists such as midaglizole, isaglidole, deriglidole, idazoxan, earoxan, fluparoxan and the like; 11) insulin or insulin mimetics such as biota, LP-100, novarapid, insulin detemir, insulini lispro, insulin glargine, insulin zinc, Lys-Pro-insulin, GLP-1(73-7), GLP 1 amide (7-36) and the like; 12) non-thiazolidindione such as JT-501, farglitazar and the like; and 13) PPARα/γdual agonists such as MK-0767, CLX-0940, GW-1536, GW-1929, GW-2433, KRP-297, L-796449, LR-90 and SB219994 and the like; can be named.

As said treating agent for hyperlipidermia, for example, 1) cholic acid absorbefacients such as colestrylamine, colesevelem, colestipol, dialkylaminoalkyl derivatives of crossdextran, Colestid™, LoCholest™, Ovestram™ and the like; 2) HMG-CoA reductase inhibitors such as atorvastatin, itavastatin, fluvastatin, lovastatin, pravastatin, rivastatin, rosuvastatin, simvastatin, ZD-4522 and the like; 3)HMG-CoA synthesis inhibitors; 4) cholesterol absorption inhibitors such as snatol ester, β-sitosterol, sterol gluoside, ezetimibe and the like; 5) acyl coenzyme A cholesterol acyl transferase inhibitors such as avasimibe, eflucimibe, KY-505, SMP-709 and the like; 6) CETP inhibitors such as JTT 705, torcetrapib, CP532632, BAY-63-2149, SC-591, SC-795 and the like; 7) squalene synthesis inhibitors; 8) antioxidants such as probucol; 9) PPARα agonists such as beclofibrate, benzafibrate, ciprofibrate, clofibrate, ethofibrate, fenofibrate, gemcabene, gemfibrozil, GW-7647, BM-170744, LY-518674, fibric acid derivatives [e.g., Atromid™, Lopid™, Tricor™ and the like; 10) FXR receptor antagonists such as GW-4064, SR-103912 and the like; 11) LXR receptor agonists such as GW3965, T9013137, XTCO-179628 and the like; 12) lipoprotein synthesis inibitors such as niacin; 13) renin-angiotensin inhibitors; 14) microsome-triglyceride transport inhibitors; 15) cholic acid resorption inhibitors such as BARA 1453, SC435, PHA384640, S435, AZD7706 and the like; 16) PPAR δ agonists such as GW501516, GW590735 and the like; 17) triglyceride synthesis inhibitors; 18) MTTP inhibitors such as LAB687, CP346086 and the like; 19) low density lipoprotein receptor inducer, 20) squalene epoxidase inhibitors; 21) thrombocyte agglutination inhibitors; and 22) 5-lypoxygenase-activating protein inhibitors such as MK-591; can be named.

As said treating agents for hypertension, for example, 1) diuretic such as thiazide-type diuretic, e.g., chlorothialidon, chlorothiazide, dichlorophenamide, hydrofluorothiazide, indapamide, hydrochlorothiazide and the like; loop-type diuretic, e.g., bumetanide, ethacrynic acid, furosemide, torsemide and the like; sodium-type diuretic such as amiloride, triamterene and the like; and aldosterone antagonist-type diuretic, e.g., spironolactone, epirenone and the like; 2) β-adrenaline blockers such as acebutolol, atenolol, betaxolol, bevantolol, bisoprolol, bopindolol, carteolol, carvedilol, celiprolol, esmolol, indenolol, metaproplol, nadolol, nebivolol, penbutolol, pindolol, propanolol, sotalol, tertatolol, tilisolol, timolol and the like; 3) calcium channel blockers such as amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine nitrendipine, manidipine, pranidipine, verapamil and the like; 4) angiotensin converting enzyme inhibitors such as benazepril, captopril, cilazapril, delapril, enalapril, fosinopril, imidapril, losinopril, moexipril quinapril, quinaprilat, ramipril, perindopril, peridropril, quanipril, spirapril, tenocapril, trandolapril, zofenopril and the like; 5) neutral endopeptidase inhibitors such as omapatrilat, cadoxatril, ecadotril, fosidotril, sampatrilat, AVE 7688, ER 4030 and the like; 6) endothelin antagonists such as tezosentan, A308165, YM62899 and the like; 7) vasodilators such as hydrazidine, clonidine, minoxidil, nicotinyl alcohol and the like; 8) angiotension II antagonists such as candesartan, eprosartan, irbesartan, losartan, pratosartan, tasosartan, telmisartan, valsartan, EXP-3137, FI6828K, RNH6270 and the like; 9) α/β adrenaline blockers such as nipradilol, arotinolol, amosulalol and the like; 10) α1 blockers such as terazosin, urapidil, prazosin, bunazosin, trimazosin, doxazosin, naftopidil, indoramin, WHIP164, XEN010 and the like; 11) α2 agonists such as lofexidine, tiamenidine, moxonidine, rilmenidine, guanobenz and the like; and 12) aldosteron inhibitors can be named.

As said anti-obesity agents, for example, 1) 5HT (serotonin) transporter inhibitors such as paroxetine, fluoxetine, fenfluramine, fluvoxamine, sertraline, imipramine and the like; 2) norepinephrine transporter inhibitors such as GW320659, desipramine, talsupram, nomifensine and the like; 3) cannabinoid 1 receptor 1(CB-1) antagonist/inverse agonist such as rimonabant (Sanofi Synthelabo), SR-147778 (Sanofi Synthelabo), BAY-65-2520 (Bayer), SLV-319 (Sorbay) and those compounds disclosed in U.S. Pat. No. 5,532,237, U.S. Pat. No. 4,973,587, U.S Pat. No. 5,013,837, U.S. Pat. No. 5,081, 122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546, and the like; 4) ghrelin antagonists such as those compounds disclosed in, e.g., WO01/87355 and WO02/08250; 5) histamine (H3) antagonist/inverse agonist such as thioperamide, 3-(1H-imidazol-4-yl) propyl N-(pentenyl) carbonate, clobenpropit, iodophenpropit, imoproxifan, GT2395, A331440, compounds disclosed in WO02/15905, 0-[3-(1H-imidazo-4-yl)propanol]carbamate, piperazin-containing H3 receptor antagonist (Lazewska D. et al., Pharmazie, 56:927-32 (2001), benzophenone derivatives (Sasse, A. et al., Arch.

Pharm. (Weinheim) 334:45-52 (2001)), substituted N-phenylcarbamate (Reidemeister, S. et al., Pharmazie, 55:83-6 (2000)), proxyphene derivatives (Sasse, A. et al., J. Med. Chem. 43:3335-43(2000)) and the like; 6) MCH-1R antagonists such as T-226296 (Takeda), SNP-7941 (Synaptic) and other compounds disclosed in WO01/82925, WO01/87834, WO02/051809, WO02/06245, WO02/076929, WO02/076947, WO02/04433, WO02/51809, WO02/083134, WO02/094799, WO03/004027 and JP2001-226269A, and the like; 7) MCH-2R agonist/antagonists; 8) NPY1 antagonists such as 3-chloro-5-(1-(6-[2-(5-ethyl-4-methyl-thiazol-2-yl)-ethyl]-4-morpholinyl-4-yl-pyridin-2-ylamino)-ethyl) phenyl]carbamic acid isopropyl ester, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528, and the like; 9) NPY5 antagonists such as 152804, GW-569180A, GW-594884A, GW-587081X, GW-548118X FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO01/107409, WO00/185714, WO00/185730, WO00/64880, WO00/68197, WO00/69849, WO01/09120, WO01/14376, WO01/85714, WO01/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789 and Norman et al., J. Med. Chem. 43:4288-4312 (2000), and the like; 10) leptins such as human recombinant leptin (PEG-OB, Hoffman La Ròche), recombinant methionyl-leptin (Amgen) and the like; 11) leptin derivatives such as those compounds which are disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519 and WO96/23520, and the like; 12) opioid antagonists such as Nalmefene (registered trademark to Revex), 3-methoxynaltrexone, naloxone, naltrexone, compounds disclosed in WO00/21509 and the like; 13) orexin antagonists such as SB-334867A and other compounds disclosed in WO01/96302, WO01/68609, WO02/51232, WO02/51838, WO03/023561, and the like; 14) bombesin receptor subtype 3 agonist; 15) cholecystokinin A (CCK-A) agonists such as AR-R15849, GI-181771, JMV-180, A-71378, A-71623, SR-146131, other compounds disclosed in U.S. Pat. No. 5,739,106, and the like; 16) CNTF (ciliary neurotrophic factors) such as GI-181771 (Glaxo-SmithKine), SR146131 (Sanofi Synthelabo), butabindide, PD170,292, PD149164 (Pfizer) and the like; 17) CNTF derivatives such as axokine (Regeneron), other compounds which are disclosed in WO94/09134, WO98/22128 and WO99/43813, and the like; 18) growth hormone secretion receptor agonists such as NN 703, hexarelin, MK-0677, SM-130686, CP-424,391, L-692,429, L-163,255, U.S. Pat. No. 6,358,951, U.S. Patent Application Nos. 2002/049196 and 2002/022637, WO01/56592 and WO02/32888, and the like; 19) serotonin receptor 2C agonists such as BVT933, DPCA37215, IK264, PNU22394, WAY161503, R-1065, YM348, other compounds disclosed in U.S. Pat. No. 3,914,250, WO02/36596, WO02/48124, WO02/10169, WO01/66548, WO02/44152, WO02/51844, WO02/40456 and WO02/40457, and the like; 20) melanocortin 3 receptor agonist; 21) melanocortin 4 receptor agonists such as CHIR86036 (Chiron), ME-10142, ME-10145 (Melacure), other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847, and the like; 22) monoamine resorption inhibitors such as Sibutramine (registered trademark to Meridia/Reductil) and salts thereof, other derivatives disclosed in U.S. Pat. No. 4,746,680, U.S. Pat. No. 4,806,570, U.S. Pat. No. 5,436,272, US Patent Application No. 2002/0006964, WO01/27068 and WO01/62341, and the like; 23) Serotonin re-introjection inhibitors such as dexfenfluramine, fluoxetine, other compounds disclosed in U.S. Pat. No. 6,365,633, WO01/27060 and WO01/162341, and the like; 24) glucagons-like peptide 1 agonist 25) Topiramate (registered trademark to Topimax); 26) phytopharm compound 57 (e.g., CP644,673); 27) acetyl CoA carboxylase 2 (ACC2) inhibitor, 28) β-adrenalin receptor 3 agonists such as AD9677/TAK677(Dainippon Pharmaceutical/Takeda Pharmaceutical), CL-316,243, SB418790, BRL-37344, L-796568, BMS-196085, BRL-35135A, CGP12177A, BTA-243, W427353, Trecadrine, ZenecaD7114, SR59119A, other compounds disclosed in U.S. Pat. No. 5705515,U.S. Pat. No. 5,451,677, WO01/74782 and WO02/32897, and the like; 29) diacylglycerolacyl transferase 1 inhibitor, 30) diacylglycerolacyl transferase 2 inhibitor, 31) fatty acid synthesis inhibitors such as Cerulenin, C75 and the like; 32) phosphodiesterase inhibitors such as theofylline, pentoxyfylline, zaprinast, sildenafil, amrinone, milrinone, cilostamide, rolipram, cilomilast and the like; 32) thyroid hormone β agonists such as KB-2611 (KaroBio BMS), other compounds disclosed in WO02/15845 and JP2000-256190A, and the like; 33) UCP (uncoupling protein)-1,2 or 3-activating substances such as phytanic acid, 4-[(E)-2-(5,6,7,8-tetrahydro-5,5,8,8-tetramethyl-2-naphthalenyl)-1-propenyl] benzoic acid (TTNPB), retinoic acid, other compounds disclosed in WO99/00123, and the like; 34) acyl estrogens such as oleoylestrone, compounds disclosed in del Mar-Grasa, M. et al., Obesity Reseach, 9: 202-9 (2001); 35) glucocorticoid antagonist; 36) 11-β hydroxysteroid dehydrognase 1-type inhibitors such as BVT 3498, BVT 2733, other compounds disclosed in WO01/90091, WO01/90090 and WO01/90092, and the like; 37) stearyl-CoA desaturase 1 inhibitors; 38) dipeptidyl peptidase IV inhibitors such as isoleucine thiazolidide, valine pyrrolidide, NVP-DPP728, AF237, P93/01, TSL225, TMC-2A/2B/2C, FE999011, P9310/K364, VIP0177, SDZ274-444, other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181, and the like; 39) lipase inhibitors such as Tetrahydro lipstatin (registered trademark to Orlistat/Xenical), Triton WR 1339, RHC 80267, lipstatin, teasaponin, diethylumbelliferyl phosphate, FL-386, WAY-121898, BAY-N-3176, valilactone, esteracin, ebelactone A, ebelectone B, RHC80267, other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453, and the like; 39) fatty acid transporter inhibitors; 40) dicarboxylate transporter inhibitors; 41) glucose transporter inhibitors; 42) phosphate transporter inhibitors; and the like can be named.

Those combination drugs are obtained by concurrent use of a compound of the present invention with one, two, or more of above drugs for combined use. Furthermore, said combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and antiobesity agent are useful for prevention, treatment or therapy of metabolic disorders with synergistic effect, when diabetes-treating agent(s) and/or hyperlipidemia-treating agent(s) are added thereto.

EXAMPLES

Hereinafter the present invention is explained more specifically referring to working Examples, it being understood that the invention is in no sense limited said Examples only. As silica gel for the columns, WAKOGEL™ C-200 or C-300 (Wako Pure Chemical Industries Ltd.) was used, and as filled silica gel columns, FLASH+™ Cartridge KP-Sil series or KP—NH series (Biotage Japan, Ltd.) were used. As the reversed phase columns for HPLC, YMC-Pack™ pro C-18 and the like (K. K. YMC) were used, and as chiral columns for HPLC, CHIRALPAK™ AD, CHIRALPAK™ AS, CHIRALPAK™ IA, CHIRALCEL™ OD, CHIRALCEL™ OJ and the like (Daicel Chemical Industries, Ltd.) were used. Mass spectra were measured with Quattro II (Micro Mass Co.).

Example 1

4-Benzyloxy-1-{4-[2-(dimethylamino)ethoxy]phenyl}-1H-pyridin-2-one (1) Preparation of 4-bezyloxypyridine 1-oxide To a DMF suspension (200 mL) of sodium hydride (60% oilyness, 7.50 g, 0.188 mmol), benzyl alcohol (20.3 mL) was added under cooling with ice, and stirred for an hour at room temperature. Then 4-nitropyridine 1-oxide (25.5 g, 182 mmols) was added little by little under stirring, followed by an hour's stirring at room temperature. The solvent was concentrated under reduced pressure and chloroform (1 L) was added to the resulting residue. The insoluble matter was filtered using Celite (100 g). The filtrate was concentrated and to which acetone was added to provide the title compound (24.8 g, 69%).

(2) Preparation of 4-benzyloxy-1H-pyridin-2-one

4-Benzyloxypyridine 1-oxide (24.8 g, 123 mmols) was refluxed in acetic anhydride (150 mL) for 1.5 hours. Cooling the system to room temperature, the system was concentrated under reduced pressure and the resulting residue was dissolved in a mixed solvent of ethyl acetate (150 mL) and methanol (10 mL), followed by stirring at 60° C. for 2 hours. The solid formed upon cooling the system to room temperature was recovered by filtration to provide crude title compound (8.84 g). Concentrating the filtrate, additional crude title compound (4.17 g) was obtained. The combined crude product was recrystallized from a mixed solvent of methanol and ethyl acetate to provide the title compound (12.1 g, 49%).

(3) Preparation of 4-benzyloxy-1-{4-[tert-butyl(dimethyl)silyloxy]phenyl}-1H-pyridin-2-one A mixture of 4-benzyloxy-1H-pyridin-2-one (200 mg, 0.994 mmol), 4-[tert-butyl(dimethyl)silyloxy]phenyboric acid (752 mg, 2.98 mmols), cupric acetate (270 mg, 1.49 mmols), pyridine (0.08 mL, 1.99 mmols) molecular sieve 4A (220 mg) and dichloromethane (4 mL) was stirred for 3 days at room temperature. Chloroform and water were added to the reaction liquid and the insoluble matter was filtered off. The organic layer was washed with saturated brine and dried over anhydrous magnesium sulfate. Concentrating the solvent under reduced pressure, the resulting residue was purified on silica gel column chromatography (C-300, methanol:chloroform=1:100) to provide the title compound (234 mg, 58%).

(4) Preparation of 4-benzyloxy-1-(4-hydroxyphenyl)-1H-pyridin-2-one

A THF solution (0.7 mL) of 1N tetrabutylammonium fluoride was added to a THF solution (2 mL) of 4-benzyloxy-1-{4-[tert-butyl(dimethyl)silyloxy]phenyl}-1H-pyridin-2-one (234 mg, 0.573 mmol) and stirred for 30 minutes at room temperature. Ethyl acetate was added to the reaction liquid, the organic layer was washed with water and saturated brine and dried over anhydrous magnesium sulfate. Concentrating the solvent under reduced pressure, the title compound (166 mg, 99%) was obtained.

(5) Preparation of 4-benzyloxy-1-{4-[2-(dimethylamino)ethoxy]phenyl}-1H-pyridin-2-one 4-Benzyloxy-1-(4-hydroxyphenyl)-1H-pyridin-2-one (150 mg, 0.511 mmol), 2-(dimethylamino)ethanol (0.057 mL, 0.562 mmol), triphenylphosphine (269 mg, 1.02 mmols) and diethyl azodicarboxylate (0.163 mL, 1.02 mmols) were stirred overnight in THF (4 mL). Concentrating the reaction liquid under reduced pressure, the resulting residue was purified on silica gel column chromatography (C-300, methanol:chloroform=1:20-1:10) to provide the title compound (124 mg, 60%).

$^1$HNMR(300 MHz,DMSO-d$_6$,δppm):2.49(6H,s), 2.62 (2H,t,J=5.8 Hz),4.07(2H,t,J=5.8 Hz),5.12(2H,s), 5.94(1H,d, J=2.6 Hz),6.05(1H,dd,J=2.6 Hz,7.6 Hz), 7.01(2H,d,J=8.9 Hz),7.23(2H,d,J=8.9 Hz),7.32-7.48(5H,m), 7.51(1H,d,J=7.6 Hz);

mass spectrum (ESI):365(M+H).

Examples 2-10

Example 1 was repeated except that 2-dimethylamino)ethanol used in Step (5) was replaced with each corresponding compound, to provide the compounds of Examples 2-10.

Example 2

4-Benxyloxy-1-{4-[2-(1-piperidinyl)ethoxy]phenyl}-1H-pyridin-2-one $^1$HNMR(300 MHz,DMSO-d$_6$,δppm):1.30-1.43(2H,m), 1.43-1.55(4H,m),2.4-2.5(4H,m),2.66(2H,t,J=5.9 Hz), 4.09 (2H,t,J=5.9 Hz),5.12(2H,s),5.94(1H,d,J=2.6 Hz), 6.05(1H, dd,J=2.6 Hz,7.7 Hz),7.00(2H,d,J=8.9 Hz), 7.23(2H,d,J=8.9 Hz),7.35-7.48(5H,m),7.50(1H,d,J=7.7 Hz);

mass spectrum (ESI):405(M+H).

Example 3

4-Benzyloxy-1-[{4-[2-(4-morpholinyl)ethoxy]phenyl}-1H-pyridin-2-one $^1$HNMR(300 MHz,DMSO-d$_6$,δppm):2.40-2.55(4H,m), 2.70(2H,t,J=5.6 Hz),3.53-3.60(4H,m),4.12(2H,t,J=5.6 Hz), 5.12(2H,s),5.94(1H,d,J=2.6 Hz),6.06(1H,dd,J=2.6 Hz,7.6 Hz), 7.01(2H,d,J=8.8 Hz),7.23(2H,d,J=8.8 Hz),7.32-7.48 (5H,m), 7.50(1H,d,J=7.6 Hz);

mass spectrum (ESI):407(M+H).

Example 4

4-Benzyloxy-1-{4-[3-(1-piperidinyl)propoxy]phenyl}-1H-pyridin-2-one $^1$HNMR(300 MHz,DMSO-d$_6$,δppm):1.33-1.43(2H,m), 1.44-1.54(4H,m),1.80-1.93(2H,m),2.20-2.50(6H,m), 4.02 (2H,t,J=6.3 Hz),5.12(2H,s),5.94(1H,d,J=2.6 Hz), 6.05(1H, dd,J=2.6 Hz,7.6 Hz),6.99(2H,d,J=8.9 Hz), 7.23(2H,d,J=8.9 Hz),7.32-7.48(5H,m),7.50(1H,d,J=7.6 Hz);

mass spectrum (ESI):419(M+H).

Example 5

4-Benzyloxy-1-(4-{2-[benzyl(methyl)amino]ethoxy}phenyl)-1H-pyridin-2-one $^1$HNMR(300 MHz,DMSO-d$_6$,δppm):2.23(3H,s), 2.75 (2H,t,J=5.9 Hz),3.57(2H,s),4.13(2H,t,J=5.9 Hz), 5.12(2H,s), 5.94(1H,d,J=2.8 Hz),6.06(1H,dd,J=2.8 Hz,7.6 Hz), 7.00(2H, d,J=8.9 Hz),7.23(2H,d,J=8.9 Hz),7.20-7.48(10H,m), 7.51 (1H,d,J=7.6 Hz);

mass spectrum (ESI):441(M+H).

Example 6

4-Benzyloxy-1-{4-[(1-methyl-2-piperidinyl)methoxy]phenyl}-1H-pyridin-2-one $^1$HNMR(300 MHz,DMSO-d$_6$,δppm):1.10-1.85(6H,m), 2.00-2.90(6H,m),3.90-4.15(2H,m),5.12(2H,s), 5.94(1H, J=2.7 Hz),6.06(1H,dd,J=2.6 Hz,7.6 Hz), 7.01(2H,d,J=8.7 Hz),7.24(2H,d,J=8.7 Hz),7.32-7.48(5H,m), 7.51(1H,d,J=7.6 Hz);

mass spectrum (ESI):405(M+H).

Example 7

4-Benzyloxy-1-{4-[1-methyl-2-pyrrolidinyl)methoxy]phenyl}1-H-pyridin-2-one $^1$HNMR(300 MHz,DMSO-d$_6$,δppm):1.50-1.75(3H,m), 1.90-2.05(1H,m),2.13-2.28(1H,m),2.37(3H,s),2.53-2.63 (1H,m), 2.92-3.00(1H,m),3.82-3.90(1H,m),3.97-4.05(1H, m),5.12(2H,s), 5.94(1H,d,J=2.9 Hz),6.06(1H,dd,J=2.9 Hz,7.6 Hz), 7.01(2H,d,J=8.9 Hz),7.23(2H,d,J=8.9 Hz),7.32-7.48(5H,m), 7.51(1H,d,J=7.6 Hz);

mass spectrum (ESI):391(M+H).

Example 8

4-Benzyloxy-1-{4-[(1-methyl-3-pyrrolidinyl)oxy]phenyl}-1H-pyridin-2-one $^1$HNMR(300 MHz,DMSO-d$_6$,δppm):1.70-1.85(1H,m), 2.25(3H,s),2.25-2.40(2H,m),2.53-2.81(3H,m),4.85-4.95 (1H,m),5.12(2H,s),5.94(1H,d,J=2.7 Hz),6.05(1H,dd,J=2.7 Hz,7.6 Hz), 6.94(2H,d,J=8.9 Hz),7.22(2H,d,J=8.9 Hz),7.32-7.48(5H,m), 7.51(1H,d,J=7.6 Hz);

mass spectrum (ESI):377(M+H).

Example 9

4-Benzyloxy-1-(4-{[(2S)-1-methyl-2-pyrrolidinyl]methoxy}phenyl)-1H-pyridin-2-one $^1$HNMR(300 MHz,DMSO-d$_6$,δppm):1.50-1.78(3H,m), 1.89-2.28(2H,m),2.36(3H,s),2.50-2.60(1H,m),2.91-3.00 (1H,m), 3.85(1H,dd,J=5.9 Hz,9.8 Hz),4.00(1H,dd,J=5.4 Hz,9.8 Hz), 5.12(2H,s),5.94(1H,d,J=2.6 Hz),6.05(1H,dd, J=2.6 Hz,7.6 Hz), 7.00(2H,d,J=8.8 Hz),7.23(2H,d,J=8.8 Hz), 7.32-7.48(5H,m), 7.51(1H,d,J=7.6 Hz);

mass spectrum (ESI):391(M+H).

Example 10

4-Benzyloxy-1-{4-[2-(diethylamino)ethoxy]phenyl}-1H-pyridin-2-one $^1$HNMR(300 MHz,DMSO-d$_6$,δppm):0.97(6H,t,J=7.11 Hz), 2.54(4H,q,J=7.1 Hz),2.78(2H,t,J=5.9 Hz),4.04(2H,t, J=5.9 Hz), 5.12(2H,s),5.94(1H,d,J=2.7 Hz),6.05(1H,dd, J=2.6 Hz,7.6 Hz), 7.00(2H,d,J=8.9 Hz),7.23(2H,d,J=8.9 Hz), 7.32-7.48(5H,m), 7.51(1H,d,J=7.6 Hz);

mass spectrum (ESI):393(M+H).

Example 11

4-Benzyloxy-1-{6-[2-(1-piperidinyl)ethoxy]pyridin-3-yl}-1H-pyridin-2-one (1) Preparation of 4-benzyloxy-1-(6-bromo-3-pyridinyl)-1H-pyridin-2-one Example 1 was repeated except that 4-[tert-butyl(dimethyl)-silyloxy]phenylboric acid which was used in Step (3) was replaced with (6-bromo-3-pyridinyl)boric acid, and 2-(dimethylamino)ethanol used in Step (5) was replaced with 2-(1-piperidine)ethanol, to provide the title compound.

(2) Preparation of 4-(benzyloxy-1-{6-[2-(1-piperidinyl)ethoxy]pyridin-3-yl}-1H-pyridin-2-one 4-Benzyloxy-1-(6-bromo-3-pyridinyl)-1H-pyridin-2-one (47 mg, 0.133 mmol), 2-(1-piperidine)ethanol (0.18 mL, 1.36 mmols) and potassium t-butoxide (150 mg, 1.34 mmols) were stirred in DMF (5 mL) for 2 hours at room temperature. Saturated aqueous sodium bicarbonate solution was added to the reaction liquid, extracted with chloroform and dried over anhydrous sodium sulfate. Concentrating the solvent underreduced pressure, the resulting residue was purified on silica gel column chromatography (C-200, methanol:chloroform=3:97-5:95-1:9-1:4) to provide the title compound (21 mg, 400%)

¹HNMR(300 MHz,CDCl₃,δppm):1.38-1.52(2H,m), 1.55-1.70(4H,m),2.42-2.64(4H,m),2.72-2.86(2H,m), 4.42-4.55(2H,m),5.05(2H,s),6.07(1H,d,J=7.0 Hz),6.09(1H,s), 6.85(1H,d,J=8.7 Hz),7.19(1H,d,J=7.0,8.6 Hz),7.32-7.50(5H,m), 7.63(1H,dd,J=2.6,8.7 Hz),8.09(1H,d,J=2.6 Hz);

mass spectrum (APcI):406.2(M+H).

Example 12

4-Benzyloxy-1-{4-[2-(1-pyrrolidinyl)ethoxy]phenyl}-1H-pyridin-2-one (1) Preparation of 4-benzyloxy-1-{4-[(2-tetrahydropyranyl)oxy]phenyl}-1H-pyridin-2-one A mixture of 4-benzyloxy-1H-pyridin-2-one (7.04 g, 35.0 mmols), 2-[(4-iodophenyl)oxy]tetrahydropyran (13.6 g, 44.8 mmols), cuprous iodide (2.1 g, 11.2 mmols), potassium carbonate (10.3 g, 73.5 mmols) and N,N-dimethylformamide (200 mL) was stirred overnight at 150° C. The reaction liquid was cooled to room temperature, into which water (1.2 L) was poured, and the formed insoluble matter was recovered by filtration. Chloroform (300 mL) was added to the insoluble matter, followed by another filtration. The filtered organic layer was washed with saturated brine and dried over anhydrous magnesium sulfate. Concentrating the solvent under reduced pressure, ethyl acetate was added to the resulting residue. The precipitate was recovered by filtration and dried to provide the title compound (7.6 g, 58%).

(2) Preparation of 4-benzyloxy-1-(4-hydroxyphenyl)-1H-pyridin-2-one

Pyridinium p-toluenesulfonate (65 mg) was added to an ethanol solution (16 mL) of 4-benzyloxy-1-{4-[(2-tetrahydropyranyl)oxy]phenyl}-1H-pyridin-2-one (982 mg, 2.60 mmols) and refluxed for an hour. The reaction liquid was cooled to room temperature and the precipitate was recovered by filtration and washed with water and ethyl acetate to provide the title compound (746 mg, 98%).

(3) Preparation of 4-benzyloxy-1-{4-[2-(1-pyrrolidinyl)ethoxy]phenyl}-1H-pyridin-2-one 4-Benzyloxy-1-(4-hydroxyphenyl)-1H-pyridin-2-one (200 mg, 0.682 mmol), 2-(1-pyrrolidine)ethanol (0.10 mL, 0.82 mmol), tri-n-butylphosphine (0.51 mL, 2.05 mmols) and 1,1'-(azodicarbonyl)dipiperidine (515 mg, 2.05 mmols) were stirred in THF (10 mL) at room temperature for an hour. Ethyl acetate was added to the reaction liquid, washed with saturated aqueous sodium bicarbonate solution and saturated brine, and dried over anhydrous potassium carbonate. Concentrating the solvent under reduced pressure, and the remaining residue was purified on silica gel column chromatography (C-300, methanol:chloroform=1:10) to provide the title compound (189 mg, 71%).

¹HNMR(300 MHz,DMSO-d₆,δppm):1.65-1.75(4H,m), 2.4-2.5(4H,m),2.79(2H,t,J=5.9 Hz),4.09(2H,t,J=5.9 Hz), 5.12(2H,s),5.94(1H,d,J=2.7 Hz),6.06(1H,dd,J=2.7 Hz,7.6 Hz), 7.00(2H,d,J=8.8 Hz),7.23(2H,d,J=8.8 Hz),7.32-7.48 (5H,m), 7.51(1H,d,J=7.6 Hz);

mass spectrum (ESI):391(M+H);

m.p.: 109-111° C.

Examples 13-15

Example 12 was repeated except that the 2-(1-pyrrolidine)ethanol which was used in Step (3) was replaced with corresponding compound in each run, to provide the compounds of Examples 13-15.

Example 13

4-Benzyloxy-1-{4-[2-(diisopropylamino)ethoxy]phenyl}-1H-pyridin-2-one

¹HNMR(300 MHz,DMSO-d₆,δppm):0.98(12H,d,J=6.5 Hz), 2.79(2H,t,J=6.9 Hz),3.01(2H,h,J=6.5 Hz),3.90(2H,t, J=5.9 Hz), 5.12(2H,s),5.94(1H,d,J=2.7 Hz),6.05(1H,dd, J=2.7 Hz,7.6 Hz), 6.98(2H,d,J=8.9 Hz),7.23(2H,d,J=8.9 Hz), 7.32-7.48(5H,m), 7.50(1H,d,J=7.6 Hz);

mass spectrum (ESI):421(M+H).

Example 14

4-Benzyloxy-1-{4-[1-(dimethylamino)-2-propoxy]phenyl}-1H-pyridin-2-one

¹HNMR(300 MHz,DMSO-d₆,δppm):1.24(3H,d,J=6.0 Hz), 2.19(6H,s),2.36(1H,dd,J=5.5 Hz,12.7 Hz),2.45-2.55 (1H,m), 4.61(1H,m),5.12(2H,s),5.95(1H,d,J=2.7 Hz), 6.05 (1H,dd,J=2.7 Hz,7.5 Hz),7.00(2H,d,J=8.9 Hz), 7.22(2H,d, J=8.9 Hz),7.32-7.48(5H,m),7.52(1H,d,J=7.5 Hz);

mass spectrum (ESI):379(M+H).

Example 15

4-Benzyloxy-1-{4-[1-(dimethylamino)-2-methyl-2-propoxy]phenyl}-1H-pyridin-2-one

Operations same to Example 12 were carried out except that the 2-(1-pyrrolidine)ethanol which was used in Step (3) was replaced with 2-dimethylamino-2-methyl-1-propanol, to provide the title compound ¹HNMR(300 MHz,DMSO-d₆,δppm):1.27(6H,s),2.29(6H, s), 2.47(2H,s),5.12(2H,s),5.96(1H,d,J=2.8 Hz), 6.06(1H,dd, J=2.8 Hz,7.6 Hz),7.04(2H,d,J=8.8 Hz), 7.23(2H,d,J=8.8 Hz), 7.32-7.48(5H,m),7.54(1H,d,J=7.6 Hz);

mass spectrum (ESI):393(M+H).

Example 16

4-Benzyloxy-1-(4-{[3S]-1-cyclopentyl-3-pyrrolidinyl]oxy}phenyl)-1H-pyridin-2-one (1) Preparation of 4-benzyloxy-1-{4-[(3S-3-pyrrolidinyloxy]phenyl}-1H-pyridin-2-one 4-Benzyloxy-1-(4-hydroxyphenyl)-1H-pyridin-2-one (300 mg, 1.02 mmols), (3R)-3-hydroxypyrrolidine-1-carboxylic acid tert-butyl ester (230 mg, 1.23 mmols), tri-n-butylphosphine (0.76 mL, 3.05 mmols) and 1,1'-(azocarbonyl)dipiperidine (770 mg, 3.05 mmols) were stirred in THF (12 mL) for an hour at room temperature. The reaction liquid was added with ethyl acetate, washed with saturated aqueous sodium bicarbonate solution and saturated brine, and dried over anhydrous potassium carbonate. Concentrating the solvent under reduced pressure, trifluoroacetic acid (1 mL) was added to the resulting residue and stirred at room temperature for an hour, followed by addition of chloroform (20 mL) and extraction with 2N hydrochloric acid (20 ml). To the aqueous layer 5N-aqueous sodium hydroxide solution was added to make the system basic, followed by extraction with chloroform, washing with saturated brine and drying over anhydrous potassium carbonate. The solvent was concentrated under reduced pressure, to provide the title compound (94 mg, 25%).

(2) Preparation of 4-benzyloxy-1-(4-{[(3S)-1-cyclopentyl-3-pyrrolidinyl]-oxy}phenyl)-1H-pyridin-2-one Cyclopentanone (0.017 mL, 0.186 mmol) and a 0.3 mol $Zn[B(CN)H_3]_2$ methanol solution (0.4 mL, 0.12 mmol, prepared from $ZnCl_2$ and $NaB(CN)H_3$) were added to a methanol solution (1 mL) of 4-benzyloxy-1-{4-[(3S)-3-pyrrolidinyloxy]phenyl}-1H-pyridin-2-one (45 mg, 0.124 mmol) and sired at room temperature for an hour. Ethyl acetate was added to the reaction liquid, which was then washed with saturated aqueous sodium bicarbonate solution and saturated brine, and dried over anhydrous potassium carbonate. The solvent was concentrated under reduced pressure and the resulting residue was purified on silica gel chromatography (C-300; methanol:chloroform=1:10) to provide the title compound (28.2 mg, 53%).

$^1$HNMR(300 MHz,DMSO-$d_6$,δppm):1.30-1.85(9H,m), 2.20-2.35(1H,m),2.35-2.50(2H,m),2.60-2.75(2H,m), 2.80-2.90(1H,m),4.83-4.93(1H,m),5.12(2H,s), 5.95(1H,d,J=2.7 Hz),6.05(1H,dd,J=2.7 Hz,7.6 Hz), 6.95(2H,d,J=8.9 Hz),7.22 (2H,d,J=8.9 Hz),7.32-7.48(5H,m), 7.52(1H,d,J=7.6 Hz);

mass spectrum (ESI):431(M+H).

Example 17

4-Benzyloxy-1-(4-{[(3S)-1-isopropyl-3-pyrrolidinyl] oxy}phenyl)-1H-pyridin-2-one The title compound was obtained through the operations same to Example 16, except that cyclopentanone used in the Step (2) was replaced with acetone.

$^1$HNMR(300 MHz,DMSO-$d_6$,δppm):1.02(6H,d,J=5.1 Hz), 1.70-1.85(1H,m),2.20-2.55(3H,m),2.60-2.80(2H,m), 2.83-2.95(1H,m),4.83-4.93(1H,m),5.12(2H,s), 5.95(1H,d, J=2.7 Hz),6.05(1H,dd,J=2.7 Hz,7.6 Hz), 6.95(2H,d,J=8.8 Hz),7.23(2H,d,J=8.8 Hz),7.32-7.48(5H,m), 7.52(1H,d,J=7.6 Hz);

mass spectrum (ESI):405(M+H).

Examples 18-19

Operations same to Examples 16 and 17 were carried out except that (3R)-3-hydroxypyrrolidine-1-carboxylic acid tert-butyl ester which was used in said Examples was replaced with (3S)-3-hydroxypyrrolidine-1-carboxylic acid tert-butyl ester, to provide the compounds of Examples 18 and 19.

Example 18

4-Benzyloxy-1-(4-{[(3R)-1-cyclopentyl-3-pyrrolidinyl]oxy}-phenyl)-1H-pyridin-2-one $^1$HNMR(300 MHz,DMSO-$d_6$,δppm):1.30-1.85(9H,m), 2.20-2.35(1H,m),2.35-2.45(2H,m),2.60-2.73(2H,m), 2.80-2.90(1H,m),4.83-4.93(1H,m),5.12(2H,s), 5.94(1H,d,J=2.7 Hz),6.05(1H,dd,J=2.7 Hz,7.6 Hz), 6.94(2H,d,J=8.9 Hz),7.22 (2H,d,J=8.9 Hz),7.32-7.48(5H,m), 7.52(1H,d,J=7.6 Hz);

mass spectrum (ESI):431(M+H).

Example 19

4-Benzyloxy-1-(4-{[(3R)-1-isopropyl-3-pyrrolidinyl] oxy}phenyl)-1H-pyridin-2-one $^1$HNMR(300 MHz,DMSO-$d_6$,δppm):1.02(6H,d,J=5.7 Hz), 1.70-1.85(1H,m),2.20-2.55(3H,m),2.60-2.80(2H,m), 2.83-2.95(1H,m),4.83-4.93(1H,m),5.12(2H,s), 5.95(1H,d, J=2.7 Hz),6.05(1H,dd,J=2.7 Hz,7.6 Hz), 6.95(2H,d,J=8.9 Hz),7.23(2H,d,J=8.9 Hz),7.32-7.48(5H,m), 7.52(1H,d,J=7.6 Hz);

mass spectrum (ESI):405(M+H).

Example 20

4-Benzyloxy-1-{5-[2-(1-piperidinyl)ethoxy]pyridin-2-yl}-1H-pyridin-2-one (1) Preparation of 2-bromo-5-(2-tetrahydropyranyloxy)pyridine A mixture of 2-bromo-5-hydroxypyridine (1.0 g, 5.75 mmols), 3,4-dihydro-2H-pyran (0.80 mL, 8.77 mmols) and p-toluenesulfonic acid (110 mg, 0.578 mmol) was stirred overnight in dichloromethane (20 mL) at room temperature. The reaction liquid was diluted with chloroform, washed with saturated brine and dried over anhydrous magnesium sulfate. Concentrating the solvent under reduced pressure, the resulting residue was purified on silica gel column chromatography (C-300; ethyl acetate:hexane=1:20-1:10) to provide the title compound (0.81 g, 55%).

(2) Preparation of 4-benzyloxy-1-{5-[2-(1-piperidinyl)ethoxy]pyridin-2-yl}-1H-pyridin-2-one Example 12 was repeated except that 2-(4-iodophenyloxy)-tetrahydropyran was replaced with the compound as obtained in Step (1) above, and 2-(1-pyrrolidine)ethanol was replaced with 2-(1-piperidine)-ethanol, to provide the title compound.

$^1$HNMR(300 MHz,CDCl$_3$,δppm):1.40-1.75(6H,m), 2.45-2.60(4H,m),2.75-2.85(2H,m),4.15-4.25(2H,m), 5.05(2H,s), 6.02(1H,d,J=2.6 Hz),6.09(1H,dd,J=2.6,7.7 Hz), 7.29-7.48 (6H,m),7.72(1H,d,J=7.7 Hz),7.79(1H,d,J=8.9 Hz), 8.19(1H, d,J=2.6 Hz);

mass spectrum (APcI):406.1(M+H).

Examples 21-23

Example 20 was repeated except that 2-bromo-5-hydroxypyridine which was used in Example 20 was replaced with corresponding bromo compound or iodo compound and 2-(1-piperidine)ethanol was replaced with corresponding compounds, to provide compounds of Examples 21-23.

Example 21

4-Benzyloxy-1-{3-methyl-4-[2-1-piperidinyl) ethoxy]phenyl}-1H-pyridin-2-one $^1$HNMR(300 MHz,CDCl$_3$,δppm):1.40-1.58(6H,m), 2.23 (3H,s) 2.48-2.62(4H,m),2.78-2.90(2H,m),4.09-4.11(2H,m), 5.03(2H,s),5.97-6.08(2H,m),6.82-6.90(1H,m),7.05-7.13 (2H,m), 7.17-7.22(1H,m),7.30-7.46(5H,m);

mass spectrum (ESI):419.2(M+H).

Example 22

4-Benzyloxy-1-{3-fluoro-4-[2-(1-piperidinyl) ethoxy]phenyl}-1H-pyridin-2-one $^1$HNMR(300 MHz,CDCl$_3$,δppm):1.35-1.75(6H,m), 2.42-2.66(4H,m),2.78-2.90(2H,m),4.18-4.27(2H,m), 5.04(2H,s), 5.94-6.08(2H,m),6.98-7.22(4H,m),7.31-7.45(5H,m);

mass spectrum (ESI):423.2(M+H).

Example 23

4-Benzyloxy-1-{3-fluoro-4-[2-(1-pyrrolidinyl) ethoxy]phenyl}-1H-pyridin-2-one $^1$HNMR(300 MHz,CDCl$_3$,δppm):1.75-1.95(4H,m), 2.61-2.75(4H,m),2.94-3.05(2H,m),4.08-4.30(2H,m), 5.04(2H,s), 5.99-6.09(2H,m),6.99-7.22(4H,m),7.32-7.48(5H,m);

mass spectrum (ESI):409.2(M+H).

Example 24

4-[1-(4-fluorophenyl)ethoxy]-1-{4-[2-(1-pyrrolidinyl)ethoxy]phenyl}-1H-pyridin-2-one Example 12 was repeated except that 4-[1-(4-fluorophenyl)ethoxy]-1H-pyridin-2-one as obtained by repeating Steps (1) and (2) of Example 1 in which benzyl alcohol was replaced with 1-(4-fluorophenyl)ethanol, was used in place of 4-benzyloxy-1H-pyridin-2-one, to provide the title compound.

$^1$HNMR(300 MHz,CDCl$_3$,δppm):1.63(3H,d,J=6.3 Hz), 1.72-1.95(4H,m),2.57-2.78(4H,m),2.91(2H,t,J=5.9 Hz), 4.12(2H,t,J=5.9 Hz),5.30(1H,q,J=6.3 Hz),5.82(1H,d,J=2.4 Hz), 5.99(1H,dd,J=2.4,7.5 Hz),6.96(2H,d,J=8.8 Hz), 7.05 (2H,t,J=8.5 Hz),720(2H,d,J=8.8 Hz),7.12-7.22(1H,m), 7.32 (2H,dd,J=5.4,8.5 Hz);

mass spectrum (APcI):423.1(M+H).

Example 25

4-[(6-Fluoro-3-pyridinyl)methoxy]-1-{4-[2-(1-piperidinyl)ethoxy]phenyl}-1H-pyridin-2-one (1) Preparation of 4-hydroxy-1-{4-[2-(1-piperidinyl) ethoxy]phenyl}-1H-pyridin-2-one Into a THF (10 mL) solution of 4-benzyloxy-1-{4-[2-(1-piperidinyl)ethoxy]phenyl}-1H-pyridin-2-one (Example 2, 130 mg, 0.32 mmol), 10% palladium-on-carbon (165 mg) was added and stirred at room temperature for 10 hours in hydrogen atmosphere. The reaction liquid was filtered, washed thoroughly with methanol, and the filtrate was concentrated under reduced pressure. THF was added to the resulting residue and the formed precipitate was recovered by filtration and dried to provide the title compound (75 mg, 74%).

(2) Preparation of 4-(6-fluoro-3-pyridinyl)methoxy-1-{4-[2-(1-piperidinyl)ethoxy]phenyl}-1H-pyridin-2-one Into a DMF solution (0.8 mL) of 4-hydroxy-1-{4-[2-(1-piperidinyl)ethoxy]phenyl}-1H-pyridin-2-one (20 mg, 0.065 mmol), NaH (60% oiliness, 3 mg, 0.078 mmol) was added and stirred at room temeture for 20 minutes, followed by addition of DMF solution (0.2 mL) of 2-fluoro-5-methanesulfonyloxymethylpyridine (20 mg, 0.097 mmol), stirring at the same temperature for 2.5 hours and further an overnight stirring at 80° C. Ethyl acetate was added to the reaction liquid, which was then washed with saturated aqueous sodium hydrogencarbonate solution and saturated brine and dried over anhydrous sodium sulfate. Concentrating the solvent under reduced pressure, the resulting residue was purified on silica gel column chromatography (C-300; methanol:chloroform=1:10) to provide the title compound (12.5 mg, 45%).

$^1$HNMR(400 MHz,CDCl$_3$,δppm):1.42-1.50(2H,m), 1.59-1.66(4H,m),2.49-2.56(4H,m),2.80(2H,t,J=5.9 Hz), 4.14(2H,t,J=5.9 Hz),5.03(2H,s),6.01(1H,dd,J=7.8,2.3 Hz), 6.05(1H,d,J=2.3 Hz),6.96-7.02(3H,m),7.25-7.22(3H,m), 7.87(1H,td,J=7.8,2.3 Hz),8.30(1H,s);

mass spectrum (ESI):424(M+H).

Example 26

4-(4-Fluorobenzyloxy)-1-{5-[2-(1-piperidinyl)-ethoxy]pyridin-2-yl}-1H-pyridin-2-one Example 25 was repeated except that 4-benzyloxy-1-{4-[2-(1-piperidinyl)ethoxy]phenyl}-1H-pyridin-2-one and 2-fluoro-5-methanesulfonyloxymethylpyridine were replaced with 4-benzyloxy-1-[5-(2-piperidin-1-ylethoxy)pyridin-2-yl]-1H-pyridin-2-one (Example 20) and 4-fluorobenzyl bromide, to provide the title compound.

$^1$HNMR(300 MHz,CDCl$_3$,δppm):1.38-1.70(6H,m), 2.45-2.60(4H,m),2.75-2.88(2H,m),4.12-4.25(2H,m), 5.01(2H,s), 6.01(1H,d,J=2.4 Hz),6.06(1H,dd,J=2.4,7.8 Hz), 7.10(2H,t,J=8.0 Hz),7.34(1H,dd,J=3.0,8.6 Hz), 7.40(2H,dd,J=5.5,8.8 Hz),7.73(1H,d,J=7.8 Hz), 7.78(1H,d,J=8.6 Hz),8.19(1H,d,J=3.0 Hz);

mass spectrum (ESI):424.2(M+H).

Example 27

4-[(6-Methyl-3-pyridinyl)methoxy-1-{4-[2-(1piperidinyl)ethoxy]phenyl}-1H-pyridin-2-one (1) Preparation of 4-hydroxy-1-{4-[(2-tetrahydropyranyl)oxy]phenyl}-1H-pyridin-2-one Into a THF (25 mL)-MeOH (25 mL) mixed solvent solution of 4-benzyloxy-1-{4-[(2-tetrahydropyranyl)oxy]phenyl}-1H-pyridin-2-one (Step (1) of Example 12, 2.05 g, 5.4 mmols), 10% palladium-on-carbon (600 mg) was added. The atmosphere was hydrogen-substituted, and the reaction system was stirred at room temperature for 3.5 hours. The reaction liquid was filtered, the solvent was concentrated under reduced pressure, methanol was added to the resulting residue and the precipitate was recovered by filtration. Drying the same, the title compound (1.25 g, 80%) was obtained.

(2) Preparation of 4-[(6-methyl-3-pyridinyl)methoxy]-1-{4-[(2-tetrahydropyranyl)oxy]phenyl}-1H-pyridin-2-one Step (5) of Example 1 was repeated except that 4-benzyloxy-1-(4-hydroxyphenyl)-1H-pyridin-2-one and 2-dimethylamino)ethanol were replaced with the compound as obtained in above Step (1) and 5-hydroxymethyl-2-methylpyridine, to provide the title compound.

(3) Preparation of 4-[(6-methyl-3-pyridinyl)methoxy]-(4-hydroxypheny)-1H-pyridin-2-one The title compound was obtained by repeating Step (2) of Example 12, except that 4-benzyloxy-1-{4-[(2-tetrahydropyranyl)oxy]phenyl}-1H-pyridin-2-one was replaced with the compound as obtained in above Step (2).

(4) Preparation of 4-[(6-methyl-3-pyridinyl)methoxy]-1-{4-[2-(1-piperidinyl)ethoxy]-phenyl}-1H-pyridin-2-one The title compound was obtained by repeating Step (5) of Example 1 except that 4-benzyloxy-1-(4-hydroxyphenyl)-1H-pyridin-2-one was replaced with the compound as obtained in above Step (3).

$^1$HNMR(400 MHz,CDCl$_3$,δppm):1.42-1.50(2H,m), 1.60-1.67(4H,m),2.52-2.58(4H,m),2.59(3H,s), 2.82(2H,t,J=5.9 Hz),4.16(2H,t,J=5.9 Hz),5.01(2H,s), 6.01(1H,dd,J=7.8,2.3 Hz),6.05(1H,d,J=2.3 Hz), 6.98(2H,d,J=9.4 Hz),7.19-7.25 (4H,m),7.64(1H,dd,J=8.2,2.0 Hz), 8.55(1H,d,J=2.0 Hz);

mass spectrum (ESI):420(M+H).

Example 28

4-(4-Fluorobenzyloxy)-1-{4-[2-(1-piperidinyl)ethoxy]phenyl}-1H-pyridin-2-one

(1) Preparation of 4-(4-fluorobenzyloxy)-1-{4-[(2-tetrahydropyranyl)-oxy]phenyl}-1H-pyridin-2-one The title compound was obtained by repeating Step (2) of Example 25 except that 4-hydroxy-1-{4-[2-(1-piperidinyl)ethoxy]phenyl}-1H-pyridin-2-one and 2-fluoro-5-methanesulfonyloxy-methylpyridine were replaced with 4-hydroxy-1-{4-[2-tetrahydropyranyl)oxy]phenyl}-1H-pyridin-2-one (Step (1) of Example 27) and 4-fluorobenzyl bromide.

(2) Preparation of 4-(4-fluorobenzyloxy)-1-(4-hydroxyphenyl)-1H-pyridin-2-one The title compound was obtained by repeating Step (2) of Example 12, except that the compound as obtained in above Step (1) was used instead of 4-benzyloxy-1-{4-[(2-tetrahydropyranyl)oxy]phenyl}-1H-pyridin-2-one.

(3) Preparation of 4-(4fluorobenzyloxy)-1-{4-[2-(1-piperidinyl)-ethoxy]phenyl}-1H-pyridin-2-one The title compound was obtained by repeating Step (5) of Example 1, except that the compound as obtained in above Step (2) was used in place of 4-benzyloxy-1-(4-hydroxyphenyl)-1H-pyridin-2-one and 2-(1-piperidine)ethanol was used in place of 2-(dimethylamino)ethanol.

$^1$HNMR(400 MHz,CDCl$_3$,δppm):1.42-1.50(2H,m), 1.59-1.67(4H,m),2.48-2.58(4H,m),2.78-2.83(2H,m), 4.12-4.17(2H,m),4.99(2H,s),6.01(1H,dd,J=7.8,2.3 Hz), 6.04(1H,d, J=2.3 Hz),6.98(2H,d,J=8.6 Hz),7.10(2H,t,J=8.6 Hz), 7.20-7.25(3H,m),7.40(2H,dd,J=8.6,5.5 Hz);

mass spectrum (ESI):423(M+H).

Examples 29-32

Example 28 was repeated except that 2-(1-piperidine)ethanol as used in Step (3) of Example 28 was changed to corresponding compound in each run, to provide the compounds of Examples 29-32.

Example 29

4-(4-Fluorobenzyloxy)-1-{4-[2-(1-pyrrolidinyl)ethoxy]phenyl}-1H-pyridin-2-one $^1$HNMR(400 MHz,CDCl$_3$,δppm):1.83-1.88(4H,m), 2.66-2.76(4H,m),2.95-3.01(2H,m),4.16-4.21(2H,m), 4.99(2H,s),6.01(1H,dd,J=7.8,2.3 Hz),6.04(1H,d,J=2.3 Hz), 6.99(2H,d, J=8.4 Hz),7.10(2H,t,J=8.4 Hz),7.20-7.28(3H,m), 7.40(2H,dd,J=8.4,5.7 Hz);

mass spectrum (ESI):409(M+H);

m.p.: 124-126° C.

Example 30

1-{4-[2-(Diethylamino)ethoxy]phenyl}-4-(4-fluorobenzyloxy)-1H-pyridin-2-one $^1$HNMR(400 MHz,CDCl$_3$,δppm):1.11-1.19(6H,m), 2.66-2.83(4H,m),2.93-3.05(2H,m),4.09-4.25(2H,m), 4.99(2H,s), 6.02(1H,dd,J=7.8,2.3 Hz),6.04(1H,d,J=2.3 Hz), 6.98(2H,d, J=8.6 Hz),7.10(2H,t,J=8.6 Hz),7.20-7.28(3H,m), 7.40(2H,dd,J=8.6,5.7 Hz);

mass spectrum (ESI):411(M+H).

Example 31

4-(4-Fluorobenzyloxy-1-{4-[2-(4-morpholinyl)ethoxy]phenyl}-1H-pyridin-2-one $^1$HNMR(400 MHz,CDCl$_3$,δppm):2.57-2.61(4H,m), 2.82 (2H,t,J=5.5 Hz),3.73-3.76(4H,m),4.14(2H,t,J=5.5 Hz), 4.99 (2H,s),6.01(1H,dd,J=7.4,2.7 Hz),6.04(1H,d,J=2.7 Hz), 6.98 (2H,d,J=9.0 Hz),7.10(2H,t,J=8.8 Hz),7.21(1H,d,J=7.4 Hz), 7.26(2H,d,J=9.0 Hz),7.40(2H,dd,J=8.8,5.3 Hz);

mass spectrum (ESI):425(M+H).

Example 32

4-(4-Fluorobenzyloxy)-1-{4-[2-(trans-2,5-dimethyl-1-pyrrolidinyl)ethoxy]-phenyl}-1H-pyridin-2-one $^1$HNMR(300 MHz,CDCl$_3$,δppm):0.92-1.18(6H,m), 1.32-1.52(2H,m),1.95-2.15(2H,m),2.86-3.23(4H,m), 4.03-4.20 (2H,m),4.99(2H,s),6.00(1H,dd,J=2.7 Hz,7.6 Hz), 6.03(1H,d, J=2.7 Hz),6.98(2H,d,J=8.9 Hz),7.10(2H,t,J=8.8 Hz), 7.18-7.31(3H,m),7.39(2H,dd,J=5.3 Hz,8.8 Hz);

mass spectrum (ESI):437(M+H).

Example 33

4-[(5-Fluoro-2-pyridinyl)methoxy]-1-{4-[2-1-pyrrolidinyl)ethoxy]phenyl}-1H-pyridin-2-one Step (1) of Example 27 was repeated except that 4-benzyloxy-1-{4-[2-(1-pyrrolidinyl)ethoxy]phenyl}-1H-pyridin-2- one (Example 12) was used in place of 4-benzyloxy-1-[4-(2-tetrahydropyranyloxy)phenyl]-1H-pyridin-2-one. So obtained 4-hydroxy-1-{4-[2-(1-pyrrolidinyl)ethoxy]phenyl}-1H-pyridin-2-one and 2-hydroxymethyl-5-fluoropyridine were used in place of 4-benzyloxy-1-(4-hydroxyphenyl)-1H-pyridin-2-one and 2-(1-pyrrolidine)ethanol, respectively, in the reaction of Step (3) of Example 12 to provide the title compound.

$^1$HNMR(400 MHz,CDCl$_3$,δppm):1.81-1.85(4H,m), 2.64-2.69(4H,m),2.94(2H,t,J=5.9 Hz),4.15(2H,t,J=5.9 Hz), 5.15 (2H,s),6.03(1H,d,J=2.7 Hz),6.07(1H,dd,J=7.4,2.7 Hz), 6.99 (2H,d,J=9.0 Hz),7.27-7.22(3H,m),7.49-7.45(2H,m), 8.48 (1H,d,J=2.0 Hz);

mass spectrum (ESI):410(M+H).

Examples 34-43

Example 33 was repeated except that 2-hydroxymethyl-5-fluoropyridine was changed to corresponding compound in each run, to provide the compounds of Examples 34-43.

Example 34

4-[(5-Methyl-2-pyridinyl)methoxy]-1-{4-[2-(1-pyrrolidinyl)ethoxy]phenyl}-1H-pyridin-2-one $^1$HNMR(400 MHz,CDCl$_3$,δppm):1.82-1.87(4H,m),2.36 (3H,s), 2.65-2.72(4H,m),2.96(2H,t,J=5.7 Hz),4.17(2H,t, J=5.7 Hz), 5.13(2H,s),6.03(1H,d,J=2.7 Hz),6.07(1H,dd, J=7.4,2.7 Hz), 6.99(2H,d,J=9.0 Hz),7.21(1H,d,J=7.4 Hz), 7.25(2H,d,J=9.0 Hz), 7.34(1H,d,J=8.2 Hz),7.55(1H,dd, J=8.2,2.3 Hz), 8.45(1H,d,J=2.3 Hz);

mass spectrum (ESI):406(M+H).

Example 35

4-[(6-Fluoro-2-pyridinyl)methoxy]-1-{4-[2-(1-pyrrolidinyl)ethoxy]phenyl}-1H-pyridin-2-one $^1$HNMR(400 MHz,CDCl$_3$,δppm):1.84-1.89(4H,m), 2.72-2.78(4H,m),3.01(2H,t,J=5.5 Hz),4.19(2H,t,J=5.5 Hz), 5.10 (2H,s),6.00(1H,d,J=2.3 Hz),6.08(1H,dd,J=7.8,2.3 Hz), 6.91 (1H,dd,J=7.8,2.3 Hz),6.99(2H,d,J=9.4 Hz),7.23-7.27(3H, m), 7.36(1H,d,J=7.8 Hz),7.85(1H,q,J=7.8 Hz);

mass spectrum (ESI):410(M+H).

Example 36

1-{4-(1-Pyrrolidinyl)ethoxy]phenyl}-4-[(5-trifluoromethyl-2-pyridinyl)-methoxy]-1H-pyridin-2-one $^1$HNMR(400 MHz,CDCl$_3$,δppm):1.82-1.87(4H,m), 2.65-2.72(4H,m),2.96(2H,t,J=5.5 Hz),4.17(2H,t,J=5.5 Hz), 5.24 (2H,s),6.01(1H,d,J=2.7 Hz),6.10(1H,dd,J=7.8,2.7 Hz), 6.99 (2H,d,J=8.6 Hz),7.24-7.27(3H,m),7.62(1H,d,J=8.6 Hz), 7.99 (1H,d,J=8.6 Hz),8.89(1H,s);

mass spectrum (ESI):460(M+H).

Example 37

4-[(5-Difluoromethoxy-2-pyridinyl)methoxy]-1-{4-[2-(1-pyrrolidinyl)-ethoxy]phenyl}-1H-pyridin-2-one

(1) Preparation of 2-bromo-5-difluoromethoxypyridine

Potassium carbonate (2.4 g, 17.3 mmols) and sodium chlorodifluoroacetate (4.2 g, 27.5 mmols) were added to a DMF (20 mL) solution of 2-bromo-5-hydroxypyridine (2.4 g, 13.8 mmols) and stirred overnight at 80° C. The reaction liquid was cooled to room temperature, added ether, washed with water and dried over anhydrous magnesium sulfate. Concentrating the solvent under reduced pressure, the resulting residue was purified on silica gel column chromatography (C-300; hexane:ethyl acetate=100:1-100:2) to provide the title compound (1.32 g, 43%).

(2) Preparation of 2-ethoxycarbonyl-5-difluoromethoxypyridine

A DMF (15 mL)-ethanol (15 mL) mixed solvent solution of 2-bromo-5-difluoromethoxypyridine (1.32 g, 5.89 mmols), palladium acetate (132 mg, 0.59 mmol), 1,1'-bis (diphenylphosphino)ferrocene (654 mg, 1.18 mmols) and triethylamine (1.6 mL, 11.8 mmols) was stirred overnight at 50° C. in carbon monoxide atmosphere. The reaction liquid was cooled to room temperature and the solvent was concentrated under reduced pressure. Ethyl acetate was added to the resulting residue, followed by washing with water and drying over anhydrous magnesium sulfate. Concentrating the solvent under reduced pressure, the residue was purified on silica gel column chromatography (C-300, hexane:ethyl acetate=4:1-3:2) to provide the title compound (1.03 g, 80%).

(3) Preparation of 5-difluoromethoxy-2-hydroxymethylpyridine

A toluene solution (13.8 mL, 13.8 mmols) of 1N diisobutylaluminium hydride was added to a THF solution (40 mL) of 2-ethoxycarbonyl-5-difluoromethoxypyridine (1.0 g, 4.6 mols) and stirred at 0° C. for 40 minutes. Successively sodium borohydride (174 mg, 4.6 mmols) and methanol (2 mL) were added and stirred at 0° C. for 30 minutes. Sodium sulfate decahydrate was added to the reaction liquid and stirred overnight at room temperature. Filtering the insoluble matter with Celite, the solvent was concentrated under reduced pressure. The residue was purified on silica gel column chromatography (C-300, hexane:ethyl acetate=3:2-2:3) to provide the title compound (738 mg, 87%).

(4) Preparation of 4-[(5-difluoromethoxy-2-pyridinyl)methoxy]-1-{4-[2-(1-pyrrolidinyl)ethoxy]phenyl}-1H-pyridin-2-one Treating the compound as obtained in above Step (3) in the manner similar to Example 33, the title compound was obtained.

$^1$HNMR(400 MHz,CDCl$_3$,δppm):1.90-1.97(4H,m), 2.77-3.19(6H,m),4.25-4.30(2H,m),5.17(2H,s), 6.03(1H,d,J=3.1 Hz),6.08(1H,dd,J=7.8,3.1 Hz), 6.57(1H,t,J=72.4 Hz),6.99 (2H,d,J=8.6 Hz),7.22-7.28(3H,m), 7.57-7.48(2H,m),8.49 (1H,d,J=3.1 Hz);

mass spectrum (ESI):458(M+H).

Example 38

4-Cyclopentylmethoxy)-1-{4-[2-(1-pyrrolidinyl) ethoxy]phenyl}-1H-pyridin-2-one $^1$HNMR(400 MHz,CDCl$_3$,δppm):1.28-1.38(2H,m), 1.54-1.70(4H,m),1.79-1.88(6H,m),2.32-2.40 (H,m), 2.68-2.76 (4H,m),2.98(2H,t,J=5.1 Hz),3.82(2H,d,J=7.0 Hz), 4.18(2H, t,J=5.1 Hz),5.94(1H,d,J=2.4 Hz), 5.96(1H,dd,J=7.0,2.4 Hz), 6.99(2H,d,J=8.6 Hz), 7.18(1H,d,J=7.0 Hz),7.25(2H,d,J=8.6 Hz);

mass spectrum (ESI):383(M+H).

Example 39

4-(Cyclohexylmethoxy)-1-{4-[2-(1-pyrrolidinyl)ethoxy]phenyl}-1H-pyridin-2-one $^1$HNMR(400 MHz,CDCl$_3$,δppm):0.98-1.10(2H,m), 1.17-1.36(4H,m),1.50-1.90(9H,m),2.67-2.80(4H,m), 2.96-3.04 (2H,m),3.75(2H,d,J=5.5 Hz),4.17-4.23(2H,m), 5.93(1H,d, J=2.4 Hz),5.96(1H,dd,J=7.8,2.4 Hz), 6.99(2H,d,J=8.6 Hz), 7.18(1H,d,J=7.8 Hz),7.25(2H,d,J=8.6 Hz);
mass spectrum (ESI):397(M+H).

Example 40

4-[(5-Chloro-2-pyridinyl)methoxy]-1-{4-[2-(1-pyrrolidinyl)ethoxy]phenyl}-1H-pyridin-2-one $^1$HNMR(400 MHz,CDCl$_3$,δppm):1.82-1.86(4H,m), 2.65-2.71(4H,m),2.96(2H,t,J=5.9 Hz),4.16(2H,t,J=5.9 Hz), 5.15 (2H,s),6.02(1H,d,J=2.7 Hz),6.07(1H,dd,J=7.8,2.7 Hz), 6.99 (2H,d,J=9.0 Hz),7.22-7.27(3H,m),7.43(1H,d,J=8.6 Hz), 7.73 (1H,dd,J=8.6,2.3 Hz),8.58(1H,d,J=2.3 Hz);
mass spectrum (ESI):426(M+H);
m.p.: 168-170° C.

Example 41

4-[4-(Trifluoromethyl)benzyloxy]-1-{4-[2-(1-pyrrolidinyl)ethoxy]phenyl}-1H-pyridin-2-one $^1$HNMR(400 MHz,CDCl$_3$,δppm):1.83-1.88(4H,m), 2.68-2.75(4H,m),2.98(2H,t,J=5.5 Hz),4.18(2H,t,J=5.5 Hz), 5.10 (2H,s),6.02(1H,d,J=2.4 Hz),6.05(1H,dd,J=7.8,2.4 Hz), 6.99 (2H,d,J=9.4 Hz),7.22-7.27(3H,m),7.54(2H,d,J=7.8 Hz), 7.67 (2H,d,J=7.8 Hz);
mass spectrum (ESI):459(M+H).

Example 42

4-(2-Fluorobenzyloxy)-1-{4-[2-(1-pyrrolidinyl)ethoxy]phenyl}-1H-pyridin-2-one $^1$HNMR(400 MHz,CDCl$_3$,δppm):1.93-1.99(4H,m), 2.88-3.04(4H,m),3.14-3.20(2H,m),4.28-4.33(2H,m), 5.10(2H,s), 6.04(1H,dd,J=7.8,2.4 Hz),6.08(1H,d,J=2.4 Hz), 6.95-7.49 (9H,m);
mass spectrum (ESI):409(M+H).

Example 43

4-(3-Fluorobenzyloxy)-1-{4-[2-(1-pyrrolidinyl)ethoxy]phenyl}-1H-pyridin-2-one $^1$HNMR(400 MHz,CDCl$_3$,δppm):1.90-1.94(4H,m), 2.82-2.90(4H,m),3.08(2H,t,J=5.3 Hz),4.26(2H,t,J=5.3 Hz), 5.04 (2H,s),6.01(1H,d,J=2.7 Hz),6.05(1H,dd,J=7.7,2.7 Hz), 6.97-7.41(9H,m);
mass spectrum (ESI):409(M+H).

Example 44

5-(4-Fluorobenzyloxy)-2-{4-[2-(1pyrrolidinyl)ethoxy]phenyl}-2H-pyridazin-3-one (1) Preparation of 4,5-dibromo-2-4-methoxyphenyl)-2H-pyridazin-3-one Mucobromic acid (3.0 g, 11.6 mmols), 4-methoxyphenylhydrazine hydrochloride (2.6 g, 44.2 mmols) and sodium carbonate (0.95 g, 26.8 mmols) were stirred in water (48 mL) at room temperature for an hour. Formed precipitate was recovered by filtration, dried and stirred in acetic acid (20 mL) at 120° C. for 30 minutes. While the solution remained hot, water (100 mL) was added thereto and the solution was cooled to room temperature under stirring. The resulting precipitate was recovered by filtration, washed with water (50 mL) and methanol (50 mL) and dried to provide the title compound (2.73 g, 65.2%).

(2) Preparation of 4,5-dibromo-2-(4-hydroxyphenyl)-2H-pyridazin-3-one

A 1N dichloromethane solution (5.5 mL) of boron tribromide was added to a dichloromethane solution (30 mL) of 4,5-dibromo-2-(4-methoxyphenyl)-2H-pyridazin-3-one (1.1 g, 3.06 mmols), and stirred overnight at room temperature. Water (30 mL) was added and stirred for 30 minutes. The resulting precipitate was recovered by filtration, washed with water and chloroform and dried to provide the title compound (1.03 g, 97%).

(3) Preparation of 4,5-dibromo-2-{4-[(tetrahydropyranyl)oxy]phenyl}-2H-pyridazin-3-one A catalytic amount of pyridinium p-toluenesulfonate and 3,4-dihydro-2H-pyrane (0.8 mL, 8.89 mmols) were added to a dichloromethane (30 mL) solution of 4,5-dibromo-2-(4-hydroxyphenyl)-2H-pyridazin-3-one (1.03 g, 2.98 mmols), and stirred at room temperature for 2 hours, washed with saturated aqueous sodium bicarbonate solution and saturated brine, and dried over anhydrous potassium carbonate. Concentrating the solvent under reduced pressure, the resulting residue was crystallized from mixed solvent of ethyl acetate and hexane to provide the title compound (1.1 g, 86%).

(4) Preparation of 4-bromo-5-(4-fluorobenzyloxy)-2-{4-[2-tetrahydropyranyl)oxy]phenyl}-2H-pyridazin-3-one Sodium hydride (31 mg, 0.75 mmol, 60% oiliness) was added to N,N-dimethylformamide solution (2 mL) of 4-fluorobenzyl alcohol (0.091 mL, 0.84 mmol), and stirred at room temperature for an hour. This reaction liquid was gradually added to N,N-dimethylformamide solution (2 mL) of 4,5-dibromo-2-{4-[2-tetrahydropyranyl]oxy}phenyl}-2H-pyridazin-3-one (300 mg, 0.70 mmol) and stirred at room temperature for an hour. Ethyl acetate was added to the reaction liquid, followed by washing with water and saturated brine and drying over anhydrous magnesium sulfate. Concentrating the solvent under reduced pressure, the resulting residue was purified on silica gel column chromatography (C300; ethyl acetate:hexane=1:2) to provide the title compound (136 mg, 41%).

(5) Preparation of 5-(4-fluorobenzyloxy)-2-{4-[(2-tetrahydropyranyl)oxy]-phenyl}-2H-pyridazin-3-one To a tetrahydrofuran solution (1 mL) of 4-bromo-5-(4-fluorobenzyloxy)-2-{4-[(2-tetrahydropyranyl)oxy]phenyl}-2H-pyridazin-3-one (136 mg, 0.29 mmol), 2.66 N n-butyl lithium hexane-solution (0.13 mL, 0.35 mmol) was added at −78° C. and stirred for 30 minutes. Methanol was added to the reaction liquid, warmed up to room temperature and ethyl acetate was added. Thus obtained organic layer was washed with 5% aqueous citric acid solution and saturated brine, and dried over anhydrous magnesium sulfate. Concentrating the solvent under reduced pressure, the resulting residue was purified on silica gel column chromatography (C-300; ethyl acetate:hexane=1:1) to provide the title compound (74.2 mg, 65.3%).

(6) Preparation of 5-(4-fluorobenzyloxy)-2-{4-[2-(1-pyrrolidinyl)ethoxy]-phenyl}-2H-pyridazin-3-one The reactions of Steps (2) and (3) of Example 12 were conducted using the compound as obtained in above Step (5) in place of 4-benzyloxy-1-{4-[2-tetrahydropyranyl)oxy]phenyl}-1H-pyridin-2-one, to provide the title compound.

$^1$HNMR(300 MHz,DMSO-$d_6$,δppm):1.65-1.80(4H,m), 2.50-2.75(4H,m),2.80-3.00(2H,m),4.13(2H,t,J=5.6 Hz), 5.16(2H,s),6.49(1H,d,J=2.8 Hz),7.02(2H,d,J=8.9 Hz), 7.26 (2H,t,J=8.7 Hz),7.38(2H,d,J=8.9 Hz), 7.38(2H,dd,J=5.6 Hz,8.7 Hz),7.92(1H,d,J=2.8 Hz);

mass spectrum (ESI):410(M+H).

Example 45

4-[(E)-2-(4-Fluorophenyl)vinyl]-1-{4-[2-(1-pyrrolidinyl)ethoxy]phenyl}-1H-pyridin-2-one (1) Preparation of 4-iodo-2-4-methoxybenzyloxy)pyridine Sodium hydride (60% oiliness, 4.93 g, 0.188 mmol) was added to DMF (250 mL) solution of 4-methoxybenzyl alcohol (17.04 g) under cooling with ice, and stirred for 30 minutes, followed by addition of 2-fluoro-4-iodopyridine (25.0 g) and 2 hours' stirring at room temperature. Water was added to the reaction liquid, followed by extraction with ether. The organic layer was washed with saturated brine and dried over anhydrous magnesium sulfate. The solvent was concentrated under reduced pressure, diisopropyl ether was added to the residue, and the formed solid was recovered by filtration to provide the title compound (26.15 g, 68%).

(2) Preparation of 4-[(E)-2-(4-fluorophenyl)vinyl]-2-(4-methoxybenzyloxy)-pyridine 4-Fluorostyrene (3.0 mL), dichlorobis(triphenylphosphine)palladium (870 mg) and potassium carbonate (5.2 g) were added to DMF (70 mL) solution of 4-iodo-2-(4-methoxybenzyloxy)pyridine (4.25 g) and stirred at 100° C. for 19 hours. Saturated brine was added to the reaction liquid, followed by extraction with ethyl acetate and drying over anhydrous magnesium sulfate. Concentrating the solvent under reduced pressure, the resulting residue was purified on silica gel column chromatography (C-200; ethyl acetate:hexane=1: 19-1:9-1:4) to provide the title compound (2.55 g, 61%).

(3) Preparation of 4-[(E)-2-2-(4-fluorophenyl)vinyl]-1H-pyridin-2-one

Trifluoroacetic acid (15 mL) was added to a chloroform (15 mL) solution of 4-(E)-2-(4-fluorophenyl)vinyl]-2-(4-methoxybenzyloxy)pyridine (2.5 g) and stirred at room temperature for an hour. The reaction liquid was concentrated under reduced pressure, diethyl ether was added to the resulting residue and the formed solid was recovered by filtration to provide the title compound (1.63 g, 100%).

(4) Preparation of 4-[(E)-2-(4-fluorophenyl)vinyl]-1-{4-[2-(1-pyrrolidinyl)-ethoxy]phenyl}-1H-pyridin-2-one Operations similar to Steps (1), (2) and (3) of Example 12 were conducted except that 4-[(E)-2-(4-fluorophenyl)vinyl]-1H-pyridin-2-one was used in place of 4-benzyloxy-1H-pyridin-2-one in Example 12, to provide the title compound.

$^1$HNMR(300 MHz,CDCl$_3$,δppm):1.88-2.08(4H,m), 2.85-3.07(4H,m),3.07-3.28(2H,m),4.28-4.42(2H,m), 6.46(1H,dd, J=1.9,7.2 Hz),6.62(1H,d,J=1.9 Hz), 6.83(1H,d,J=16.4 Hz), 7.02(2H,d,J=8.9 Hz),7.09(2H,d,J=8.9 Hz), 7.16(1H,d,J=16.4 Hz),7.30(1H,d,J=7.2 Hz),7.32(2H,d,J=8.9 Hz), 7.79(2H,dd, J=5.4,8.7 Hz);

mass spectrum (ESI):405.1(M+H).

Example 46

4-[(E)-2-2-phenylvinyl]-1-{4-[2-(1-pyrrolidinyl)ethoxy]phenyl}-1H-pyridin-2-one

Example 45 was repeated except that styrene was used in place of 4-fluorostyrene in Step (2) of Example 45, to provide the title compound.

$^1$HNMR(300 MHz,CDCl$_3$,δppm):1.72-1.92(4H,m), 2.53-2.75(4H,m),2.93(2H,t,J=6.0 Hz),4.15(2H,t,J=6.0 Hz), 6.48 (1H,dd,J=1.8,7.5 Hz),6.64(1H,d,J=1.8 Hz), 6.92(1H,d, J=16.3 Hz),7.01(2H,d,J=8.9 Hz),7.20(1H,d,J=16.3 Hz), 7.25-7.45(6H,m),7.51-7.59(2H,m);

mass spectrum (APcI):387.1(M+H).

Example 47

4-[(E)-2-(5-chloro-2-pyridinyl)vinyl]-1-{4-[2-(1-pyrrolidinyl)ethoxy]phenyl}-1H-pyridin-2-one (1) Preparation of 5-chloro-2-vinylpyridine A mixture of 2,5-dichloropyridine (10.0 g), potassium vinyltrifluoroborate (10.86 g), dichloromethane complex (2.5 g) of dichloro-1,1'-bis(diphenylphosphino)-ferrocene palladium (II), triethylamine (14.13 mL) and ethanol (150 mL) was stirred overnight under reflux. After cooling the system to room temperature, ethyl acetate was added, followed by washing with saturated aqueous sodium hydrogencarbonate solution and saturated brine and drying over anhydrous sodium sulfate. Concentrating the solvent under reduced pressure, the resulting residue was distilled under reduced pressure (63° C., 8 mmHg) to provide the title compound (6.50 g, 69%).

(2) Preparation of 4-[(E)-2-(5-chloro-2-pyridinyl)vinyl]-1-{4-[2-(1-pyrrolidinyl)ethoxy]-phenyl}-1H-pyridin-2-one Example 45 was repeated except that 5-chloro-2-vinylpyridine was used in place of 4-fluorostyrene, to provide the title compound.

$^1$HNMR(400 MHz,CDCl$_3$,δppm):1.80-1.85(4H,m), 2.60-2.67(4H,m),2.92(2H,t,J=5.9 Hz),4.15(2H,t,J=5.9 Hz), 6.48 (1H,dd,J=2.0,7.1 Hz),6.72(1H,d,J=2.0 Hz), 7.02(2H,d,J=8.7 Hz),7.18(1H,d,J=16 Hz),7.31(2H,d,J=8.7 Hz), 7.33(1H,d, J=7.1 Hz),7.38(1H,d,J=8.4 Hz),7.42(1H,d,J=16 Hz), 7.69 (1H,dd,J=2.6,8.4 Hz),8.59(1H,d,J=2.6 Hz);

mass spectrum (ESI):422(M+H).

Example 48

4-[(E)-2-(5-fluoro-2-pyridinyl)vinyl]-1-{4-[2-[1-pyrrolidinyl]ethoxy]phenyl}-1H-pyridin-2-one Example 47 was repeated except that 5-chloro-2-fluoropyridine was used in place of 2,5-dichloropyridine in Step (1) of Example 47, to provide the title compound.

$^1$HNMR(300 MHz,CDCl$_3$,δppm):1.72-1.92(4H,m), 2.58-2.75(4H,m),2.93(2H,t,J=6.0 Hz),4.16(2H,t,J=6.0 Hz), 6.48 (1H,dd,J=1.9,7.2 Hz),6.71(1H,d,J=1.9 Hz), 7.01(2H,d,J=9.0 Hz),7.20(1H,d,J=15.8 Hz),7.25-7.38(3H,m), 7.36(1H,d,J=15.8 Hz),743(2H,d,J=9.0 Hz),8.50(1H,d,J=3.2 Hz);

mass spectrum (ESI):406.3(M+H).

Examples 49-50

Example 45 was repeated except that 2-(1-pyrrolidine)ethanol in Step (4) of Example 45 was replaced with each corresponding compound, to provide the compounds of Examples 49-50.

Example 49

4-[(E)-2-(4-fluorophenyl)vinyl]-1-{4-[2-(2-oxo-1-pyrrolidinyl)ethoxy]phenyl}-1H-pyridin-2-one $^1$HNMR(300 MHz,CDCl$_3$,δppm):2.04(2H, tt,J=7.1,8.1 Hz), 2.40(2H,t,J=8.1 Hz),3.59(2H,t,J=7.1 Hz),3.71(2H,t,J=5.1 Hz), 4.15(2H,t,J=5.1 Hz),6.46(1H,dd,J=1.9,7.2 Hz), 6.62(1H,d,J=1.9 Hz),6.83(1H,d,J=16.2 Hz),6.98(2H,d,J=8.9 Hz), 7.09(2H,t,J=8.7 Hz),7.15(1H,d,J=16.2 Hz),7.30(1H,d,J=7.2 Hz), 7.31(2H,d,J=8.9 Hz),7.52(2H,dd,J=5.4,8.7 Hz);

mass spectrum (ESI):419.2(M+H).

Example 50

4-[(E)-2-(4-fluorophenyl)vinyl]-1-(4-{2-[(3R)-3-fluoro-1-pyrrolidinyl]ethoxy}-phenyl)-1H-pyridin-2-one $^1$HNMR(300 MHz,CDCl$_3$,δppm):1.99-2.25(2H,m), 2.57-2.64(1H,m),2.83-3.06(5H,m),4.16(2H,t,J=5.7 Hz), 5.11-5.29(1H,m),6.46(1H,dd,J=7.4,2.0 Hz),6.63(1H,d,J=2.0 Hz), 6.83(1H,d,J=16.0 Hz),7.00(2H,d,J=8.6 Hz),7.09(2H,t,J=8.6 Hz), 7.15(1H,d,J=16.0 Hz),729-7.32(3H,m), 7.52(2H,dd,J=8.6,5.5 Hz);

mass spectrum (ESI):423(M+H).

Example 51

4-[(E)-2-(4-methoxyphenyl)vinyl]-1-{4-[2-(1-pyrrolidinyl]ethoxy}phenyl)-1H-pyridin-2-one (1) Preparation of 4-((E)-2-{4-[(2-methyl-2-propyl)oxy]phenyl}vinyl)-2-(4-methoxybenzyloxy)pyridine Step (2) of Example 45 was repeated except that 4-fluorostyrene was replaced with 4-[(2-methyl-2-propyl)oxy]styrene, to provide the title compound.

(2) Preparation of 4-((E-2-{4-[(2-methyl-2-propyl)oxy]phenyl}vinyl)-1H-pyridin-2-one Formic acid (1.0 mL, 26.50 mmols) and palladium hydroxide (167 mg) were added to a methanol (20 mL) solution of 4-((E)-2-{4-[(2-methyl-2-propyl)oxy]phenyl}vinyl)-2-(4-methoxybenzyloxy)pyridine (1.03 g, 2.64 mmols), and stirred at 80° C. for 2 hours. The reaction liquid was filtered through Celite and concentrated under reduced pressure to provide a yellow solid. Washing the solid with diethyl ether (20 mL), the title compound was obtained as a white solid (523 mg, 73%).

(3) Preparation of 4-((E)-2-{4-[(2-methyl-2-propyl)oxy]phenyl}vinyl)-1-[4-(2-tetrahydropyranyloxy)phenyl]-1H-pyridin-2-one Step (1) of Example 12 was repeated except that 4-benzyloxy-1H-pyridin-2-one was replaced with 4-((E)-2-{4-[(2-methyl-2-propyl)oxy]phenyl}-vinyl)-1H-pyridin-2-one, to provide the title compound.

(4) Preparation of 4-((E)-2-{4-[(2-methyl-2-propyl)oxy]phenyl}vinyl)-1-(4-hydroxyphenyl)-1H-pyridin-2-one Acetic acid (2 mL) and water (0.5 mL) were added to a THF (3 mL) solution of 4-((E-2-{4-[(2-methyl-2-propyl)oxy]phenyl}vinyl)-1-[4-(2-tetrahydropyranyloxy)phenyl]-1H-pyridin-2-one (200 mg, 0.45 mmol) and stirred at 70° C. for 2 hours. Concentrating the reaction liquid under reduced pressure, a yellow solid was obtained The solid was washed with water (30 mL) to provide the title compound (164 mg, 98%) as a white solid.

(5) Preparation of 4-((E)-2-{4-[(2-methyl-2-propyl)oxy]phenyl}vinyl)-1-{4-[2-(1-pyrrolidinyl)ethoxy]pheny}-1H-pyridin-2-one Step (3) of Example 12 was repeated except that 4-benzyloxy-1-(4-hydroxyphenyl)-1H-pyridin-2-one was replaced with 4-((E)-2-{4-[(2-methyl-2-propyl)oxy]phenyl}vinyl)-1-(4-hydroxyphenyl)-1H-pyridin-2-one, to provide the title compound.

(6) Preparation of 4-[(E)-2-(4-hydroxyphenyl)vinyl]-1-{4-[2-(1-pyrrolidinyl)-ethoxy]phenyl}-1H-pyridin-2-one Trifluoroacetic acid (2 mL) was added to 4-((E)-2-{4-[(2-methyl-2-propyl)oxy]phenyl}vinyl)-1-{4-[2-(1-pyrrolidinyl)ethoxy]phenyl}-1H-pyridin-2-one (120 mg, 0.26 mmol) and stirred at room temperature for 30 minutes. After concentrating the reaction liquid under reduced pressure, chloroform was added to the reaction liquid which then was washed with aqueous sodium hydrogencarbonate solution and dried over anhydrous sodium sulfate. Concentrating the solvent under reduced pressure, the title compound (97 mg, 92%) was obtained as a white solid.

(7) Preparation of 4-[(E)-2-(4-methoxyphenyl)vinyl]-1-{4-[2-(1-pyrrolidinyl]-ethoxy}phenyl)-1H-pyridin-2-one Potassium carbonate (11 mg, 0.08 mmol) and methyl p-toluenesulfonate (6 mg, 0.03 mmol) were added to DMF (2 mL) solution of 4-[(E)-2-4-hydroxyphenyl)vinyl]-1-{4-[2-(1-pyrrolidinyl)ethoxy]phenyl}-1H-pyridin-2-one (11 mg, 0.03 mmol), and stirred for a day and night at 80° C. Ethyl acetate was added to the reaction liquid, followed by washing with water and saturated brine and drying over anhydrous sodium sulfate. Concentrating the reaction liquid under reduced pressure, the residue was purified on silica gel column chromatography (C-300; methanol:chloroform=1:20-1:10) to provide the title compound (6 mg, 53%) as a white solid.

¹HNMR(400 MHz,CDCl₃,δppm):1.80-1.86(4H,m), 2.61-2.70(4H,m),2.95(2H,t,J=6.0 Hz),3.83(3H,s), 4.16(2H,t, J=6.0 Hz),6.45(1H,dd,J=1.6 Hz,7.6 Hz),6.60(1H,s), 6.79 (1H,d,J=16.0 Hz),6.94(2H,d,J=8.8 Hz),7.00(2H,d,J=8.8 Hz), 7.15(1H,d,J=16.0 Hz),7.25-7.35(3H,m),7.48(2H,d,J=8.8 Hz);

mass spectrum (ESI):417(M+H).

Example 52

4-{(E)-2-[4-(fluoromethoxy)phenyl]vinyl}-1-{4-[2-(1-pyrrolidinyl)ethoxy]-phenyl}-1H-pyridin-2-one Step (3) of Example 51 was repeated except that methyl p-toluenesulfonate was replaced with fluoromethyl p-toluenesulfonate, to provide the title compound.

¹HNMR(400 MHz,CDCl₃,δppm):1.80-1.86(4H,m), 2.61-2.70(4H,m),2.95(2H,t,J=6.0 Hz),4.15(2H,t,J=6.0 Hz), 5.75 (2H,d,J=54.4 Hz),6.46(1H,dd,J=1.6 Hz,7.2 Hz),6.62(1H,s), 6.83(1H,d,J=16.8 Hz),7.00(2H,d,J=8.8 Hz),7.10(2H,d,J=8.8 Hz), 7.15(1H,d,J=16.8 Hz),7.25-7.35(3H,m),7.52(2H,d, J=8.8 Hz);

mass spectrum (ESI): 435(M+H).

Examples 53-54

Step (1) of Example 27 was repeated except that 4-benzyloxy-1-[4-[2-tetrahydropyranyloxy)phenyl]-1H-pyridin-2-one was replaced with the compound of Example 46 or 48 to provide the compounds of Examples 53 and 54, respectively.

Example 53

4-(2-Phenylethyl)-1-{4-[2-(1-pyrrolidinyl)ethoxy]phenyl}-1H-pyridin-2-one

¹HNMR(300 MHz,CDCl₃,δppm):1.79-1.95(4H,m), 2.65-2.86(6H,m),2.90-2.98(2H,m),3.00(2H,t,J=5.8 Hz), 4.20(2H, t,J=5.8 Hz),6.07(1H,dd,J=1.9,7.1 Hz), 6.48(1H,d,J=1.9 Hz), 7.00(2H,d,J=9.0 Hz),7.18-7.32(8H,m);

mass spectrum (ESI):389.3(M+H).

Example 54

4-[2-(5-Fluoro-2-pyridinyl)ethyl]-1-{4-[2-(1-pyrrolidinyl)ethoxy]phenyl}-1H-pyridin-2-one ¹HNMR(300 MHz,CDCl₃,δppm):1.72-1.88(4H,m), 2.55-2.70(4H,m),2.84-2.95(2H,m),2.92(2H,t,J=5.9 Hz), 3.05-3.15(2H,m),4.14(2H,t,J=5.9 Hz),6.09(1H,dd,J=1.9,7.1 Hz), 6.45(1H,d,J=1.9 Hz),6.99(2H,d,J=8.9 Hz),7.10-7.38(5H,m), 8.38-8.43(1H,m);

mass spectrum (APcI):408.1(M+H).

Example 55

4-[2-(4-Fluorophenyl)ethyl]-1-{4-[2-(1-pyrrolidinyl)ethoxy]phenyl}-1H-pyridin-2-one (1) Preparation of 4-[2-(4-fluorophenyl)ethyl]-2-(4-methoxybenzyloxy)-pyridine 9-Borabicyclo[3.3.1]nonane (540 mg) was added to THF solution (5 mL) of 4-fluorostyrene (240 mL) and stirred at room temperature for 2 hours. To the reaction liquid, the compound synthesized in Step (1) of Example 45(340 mg), tetrakis(triphenylphosphine)palladium (60 mg), DMF (5 mL) and 2M aqueous sodium carbonate solution (1 mL) were added and stirred at 100° C. for 19 hours. Saturated brine was added to the reaction liquid, followed by extraction with ethyl acetate and drying over anhydrous magnesium sulfate. Concentrating the solvent under reduced pressure, the residue was purified on silica gel column chromatography (C-200; ethyl acetate:hexane=1:9-1:4) to provide the title compound (336 mg, 100%).

(2) Preparation of 4-[2-(4-fluorophenyl)ethyl]-1-{4-[2-(1-pyrrolidinyl)ethoxy]phenyl}-1H-pyridin-2-one The title compound was synthesized by the method similar to Steps (3) and (4) of Example 45.

¹HNMR(300 MHz,CDCl₃,δppm):1.65-2.00(4H,m), 2.62-2.72(4H,m),2.68-2.83(2H,m),2.85-2.95(2H,m), 2.95(2H,t, J=5.8 Hz),4.16(2H,t,J=5.8 Hz),6.04(1H,d,J=7.0 Hz), 6.45 (1H,s),6.98(2H,d,J=8.4 Hz),7.00(2H,d,J=8.4 Hz), 7.15(2H, dd,J=5.4,8.4 Hz),7.22(1H,d,J=7.0 Hz), 7.27(2H,d,J=8.4 Hz);

mass spectrum (ESI):407.1(M+H).

Example 56

4-[(4-Fluorophenoxy)methyl]-1-{4-[2-(1-pyrrolidinyl)ethoxy]phenyl}-1H-pyridin-2-one (1) Preparation of (2-chloro-4-pyridinyl)methanol Borane-dimethyl sulfide complex (14.30 mL, 14.30 mmols) was added to tetrahydrofuran solution of 2-chloroisonicotinic acid (17.56 g, 11.5 mmols) under cooling with ice, and stirred at room temperature for 2.5 days, followed by further an hour's stirring at 50° C. Cooling the reaction liquid to room temperature, ethyl acetate was added, followed by washing with saturated aqueous ammonium chloride solution and saturated brine and drying over anhydrous sodium sulfate. Concentrating the solvent under reduced pressure, the tide compound (15.0 g, 93%) was obtained.

(2) Preparation of 2-chloro-4-[(4-fluorophenoxy)methyl]pyridine

Triethylamine (1.2 mL, 8.4 mmols) was added to a mixture of (2-chloro-4-pyridinyl)methanol (1.0 g, 7.0 mmols), methanesulfonyl chloride (0.6 mL, 7.7 mmols) and ethyl acetate (20 mL) under cooling with ice, and stirred at room temperature for 2 hours. Filtering the reaction liquid, the filtrate was concentrated. To the resulting residue, 4-fluorophenol (0.94 g, 8.4 mmols), potassium carbonate (1.93 g, 14.0 mmols) and N,N-dimethylformamide (20 mL) were added and s at 80° C. for 20 hours. Cooling the reaction liquid to room temperature, ethyl acetate was added thereto, followed by washing with saturated aqueous sodium hydrogencarbonate solution and saturated brine and drying over anhydrous sodium sulfate. Concentrating the solvent under reduced pressure, the residue was purified on silica gel column chromatography (KP-Sil, FLASH 40+M, chloroform) to provide the title compound (845 mg, 51%).

(3) Preparation of 2-(benzyloxy)-4-[(4-fluorophenoxy)methyl]pyridine

A mixture of 2-chloro-4-[(4-fluorophenoxy)methyl]pyridine (845 mg, 3.55 mmols), benzyl alcohol (0.48 mL, 4.62 mmols), sodium hydride (60% oiliness, 170 mg, 4.26 mmols) and tetrahydrofuran (20 mL) was refluxed for 16 hours. Cooling the reaction liquid to room temperature, ethyl acetate was added thereto, followed by washing with saturated aqueous sodium hydrogencarbonate solution and saturated brine and drying over anhydrous sodium sulfate. Concentrating the solvent under reduced pressure, the residue was purified on silica gel column chromatography (KP-Sil, FLASH 40+M, hexane:ethyl acetate=10:0-17:3) to provide the title compound (1.09 g, 99%).

(4) Preparation of 4-fluorophenoxy)methyl]-1H-pyridin-2-one

Ten (10)% hydrogen chloride-methanol solution (20 mL) was added to 2-(benzyloxy)-4-[(4-fluorophenoxy)methyl]pyridine (1.09 g, 3.52 mmols) and stirred at 75° C. for 24 hours. The solvent was concentrated under reduced pressure and ethyl acetate and diethyl ether were added to the remaining residue. Filtering the system, the title compound (769 mg, 100%) was obtained.

(5) Preparation of 4-[(4-fluorophenoxy)methyl]-1-{4-[2-(1-piperidinyl)-ethoxy]phenyl}-1H-pyridin-2-one Steps (3), (4) and (5) of Example 1 were repeated except that 4-benzyloxy-1H-pyridin-2-one used in Step (3) was replaced with 4-(4-fluorophenoxy)methyl]-1H-pyridin-2-one and 2-dimethylaminoethanol in Step (5) was replaced with 2-(1-pyrrolidine)ethanol, respectively, to provide the title compound.
$^1$HNMR(300 MHz,CDCl$_3$,δppm):1.82-1.87(4H,m), 2.63-2.73(4H,m),2.96(2H,t,J=6.0 Hz),4.17(2H,t,J=6.0 Hz), 4.91 (2H,d,J=1.2 Hz),6.27(1H,dd,J=7.1,1.5 Hz), 6.71(1H,d,J=1.5 Hz),6.88-6.91(2H,m),6.98-7.02(4H,m), 7.26-7.29(2H,m), 7.33(1H,d,J=7.1 Hz);
mass spectrum (ESI):409(M+H).

Examples 57-60

Example 56 was repeated except that 4-fluorophenol used in the Step (2) and 2-(1-pyrrolidine)ethanol used in the Step (5) were replaced with each corresponding compounds, respectively, to provide the title compounds.

Example 57

4-[(4-Chlorophenoxy)methyl]-1-{4-[2-(1-pyrrolidinyl)ethoxy]phenyl}-1H-pyridin-2-one $^1$HNMR(300 MHz,CDCl$_3$,δppm):1.79-1.86(4H,m), 2.60-2.66(4H,m),2.93(2H,t,J=6.0 Hz),4.15(2H,t,J=6.0 Hz), 4.92 (2H,s),6.26(1H,dd,J=7.0,1.6 Hz),6.70(1H,d,J=1.6 Hz), 6.89 (2H,dt,J=9.0,2.4 Hz),7.01(2H,dt,J=9.0,2.4 Hz), 7.24-7.30 (4H,m),7.33(1H,d,J=7.0 Hz);
mass spectrum (APCI):425(M+H).

Example 58

4-(Phenoxymethyl)-1-{4-[2-(1-pyrrolidinyl)ethoxy]phenyl}-1H-pyridin-2-one $^1$HNMR(300 MHz,CDCl$_3$,δppm):1.79-1.86(4H,m), 2.60-2.70(4H,m),2.94(2H,t,J=6.0 Hz),4.15(2H,t,J=6.0 Hz), 4.95 (2H,s),6.30(1H,dd,J=7.2,1.8 Hz), 6.73(1H,d,J=1.8 Hz), 6.95-7.02(5H,m),7.25-7.35(5H,m);
mass spectrum (APCI):391(M+H).

Example 59

1-{4-[2-(1-Pyrrolidinyl)ethoxy]phenyl}-4-{[4-(trifluoromethyl)phenoxy]-methyl}-1H-pyridin-2-one $^1$HNMR(300 MHz,CDCl$_3$,δppm):1.80-1.84(4H,m), 2.60-2.67(4H,m),2.92(2H,t,J=5.9 Hz),4.14(2H,t,J=5.9 Hz), 4.99 (2H,s),6.27(1H,dd,J=7.1,1.7 Hz),6.70-6.73(1H,m), 7.00-7.04(4H,m),7.25-7.30(2H,m),7.35(1H,d,J=7.1 Hz), 7.58 (2H,d,J=9.0 Hz);
mass spectrum (ESI):459(M+H).

Example 60

1-{4-[2-(Diethylamino)ethoxy]phenyl}-4-[(3-fluorophenoxy)methyl]-1H-pyridin-2-one $^1$HNMR(300 MHz,CDCl$_3$,δppm):1.08(6H,t,J=7.1 Hz), 2.65(4H,q,J=7.1 Hz),2.90(2H,t,J=6.2 Hz),4.08(2H,t,J=6.2 Hz), 4.93(2H,s),6.27(1H,dd,J=7.2,2.0 Hz),6.66-6.73(4H,m), 6.96-7.02(2H,m),7.24-7.29(3H,m),7.34(1H,d,J=7.2 Hz);
mass spectrum (ESI):411(M+H).

Example 61

4-(2-Pyridinylmethoxy)-1-{4-[2-(diethylamino)ethoxy]phenyl}-1H-pyridin-2-one

Steps (1) and (2) of Example 28 were repeated except that 4-fluorobenzyl bromide used in Example 28 was replaced with 2-methanesulfonyloxymethylpyridine, and successively Example 12 was repeated except that so obtained compound was used in place of 4-benzyloxy-1-(4-hydroxyphenyl)-1H-pyridin-2-one in Step (3) and 2-(1-pyrrolidine)ethanol was replaced with 2-(diethylamino)ethanol, to provide the title compound.
$^1$HNMR(300 MHz,CDCl$_3$,δppm):1.08(6H,t,J=7.1 Hz), 2.66(4H,q,J=7.1 Hz),2.90(2H,t,J=6.2 Hz),4.08(2H,t,J=6.2 Hz), 5.18(2H,s),6.04(1H,d,J=2.7 Hz),6.08(1H,dd,J=2.7,7.5 Hz), 6.97(2H,d,J=8.9 Hz),7.20-7.32(4H,m),7.46(1H,d,J=7.7 Hz), 7.74(1H,t,J=7.7 Hz),8.63(1H,d,J=5.5 Hz);
mass spectrum (APcI):394.2(M+H).

Examples 62-76

Example 33 was repeated except that 2-hydroxymethyl-5-fluoropyridine was changed to corresponding compound in each run, to provide the compounds of Examples 62-76.

Example 62

4-[(3,4-Dimethylbenzyl)oxy]-1-{4-[2-(1-pyrrolidinyl)ethoxy)phenyl}-1H-pyridin-2-one $^1$HNMR(300 MHz,CDCl$_3$,δppm):1.79-1.84(4H,m),2.28 (3H,s), 2.29(3H,s),2.61-2.65(4H,m),2.92(2H,t,J=5.9 Hz), 4.13(2H,t,J=5.9 Hz),4.96(2H,s),6.01(1H,dd,J=7.6,2.7 Hz), 6.06(1H,d,J=2.7 Hz),6.99(2H,d,J=9.0 Hz),7.13-7.21(4H,m), 7.25(2H,d,J=9.0 Hz);
mass spectrum (ESI):419(M+H).

Example 63

4-[(3,5-Difluorobenzyl)oxy]-1-{4-[2-(1-pyrrolidinyl)ethoxy]phenyl}-1H-pyridin-2-one $^1$HNMR(300 MHz,CDCl$_3$,δppm):1.77-1.85(4H,m), 2.61-2.66(4H,m),2.93(2H,t,J=5.9 Hz),4.14(2H,t,J=5.9 Hz), 5.02(2H,s),5.98(1H,d,J=2.7 Hz),6.05(1H,dd,J=7.4,2.7 Hz), 6.76-6.83(1H,m),6.92-6.96(2H,m),7.00(2H,d,J=9.0 Hz), 7.26-7.23(3H,m);
mass spectrum (ESI):427(M+H).

Example 64

4-[(3,5-Dimethylbenzyl)oxy]-1-{4-[2-(1-pyrrolidinyl)ethoxy]phenyl}-1H-pyridin-2-one $^1$HNMR(300 MHz,CDCl$_3$,δppm):1.80-1.84(4H,m),2.34 (6H,s), 2.62-2.66(4H,m),2.92(2H,t,J=5.9 Hz),4.14(2H,t, J=5.9 Hz), 4.95(2H,s),6.03(1H,dd,J=7.4,2.5 Hz),6.05(1H,d, J=2.5 Hz), 6.97-7.04(5H,m),7.20(1H,d,J=7.4 Hz),7.25(2H,d, J=8.6 Hz);
mass spectrum (ESI):419(M+H).

Example 65

4-(2,3-Dihydro-1H-inden-5-ylmethoxy)-1-{4-[2-(1-pyrrolidinyl)ethoxy]-phenyl}-1H-pyridin-2-one $^1$HNMR(300 MHz,CDCl$_3$,δppm):1.80-1.85(4H,m), 2.06-2.13(2H,m),2.60-2.66(4H,m),2.89-2.96(6H,m), 4.14(2H,t, J=5.9 Hz),4.99(2H,s),6.01(1H,dd,J=7.6,2.5 Hz), 6.06(1H,d, J=2.5 Hz),6.99(2H,d,J=8.6 Hz),7.29-7.16(6H,m);
mass spectrum (ESI):431(M+H).

Example 66

4-(1,3-Benzodioxol-5-ylmethoxy)-1-{4-[2-(1-pyrrolidinyl)ethoxy]phenyl}-1H-pyridin-2-one $^1$HNMR(300 MHz,CDCl$_3$,δppm):1.80-1.85(4H,m), 2.63-2.68(4H,m),2.94(2H,t,J=5.9 Hz),4.15(2H,t,J=5.9 Hz), 4.92(2H,s),5.99(2H,s),5.99(1H,d,J=2.7 Hz), 6.02(1H,dd,J=7.4, 2.7 Hz),6.81-6.91(3H,m),6.99(2H,d,J=9.0 Hz), 7.20(1H,d, J=7.4 Hz),7.25(2H,d,J=9.0 Hz);
mass spectrum (ESI):435(M+H).

Example 67

1-{4-[2-(1-Pyrrolidinyl)ethoxy]phenyl}-4-(2-thienylmethoxy)-1H-pyridin-2-one $^1$HNMR(300 MHz,CDCl$_3$,δppm):1.80-1.84(4H,m), 2.62-2.66(4H,m),2.92(2H,t,J=5.9 Hz),4.14(2H,t,J=5.9 Hz), 5.19(2H,s),6.01(1H,dd,J=7.8,2.7 Hz),6.08(1H,d,J=2.7 Hz), 6.99(2H,d,J=8.9 Hz),7.04(1H,dd,J=5.1,3.5 Hz), 7.16(1H,dd, J=3.5,1.0 Hz),7.21(1H,d,J=7.8 Hz), 7.25(2H,d,J=8.9 Hz), 7.38(1H,dd,J=5.1,1.0 Hz);
mass spectrum (ESI):397(M+H).

Example 68

1-{4-[2-(1-Pyrrolidinyl)ethoxy]phenyl}-4-(3-thienylmethoxy)-1H-pyridin-2-one $^1$HNMR(300 MHz,CDCl$_3$,δppm):1.81-1.85(4H,m), 2.64-2.69(4H,m),2.94(2H,t,J=5.9 Hz),4.16(2H,t,J=5.9 Hz), 5.05 (2H,s),6.01(1H,dd,J=7.8,2.7 Hz),6.05(1H,d,J=2.7 Hz), 6.99 (2H,d,J=8.6 Hz),7.15(1H,dd,J=4.7,1.6 Hz), 7.21(1H,d,J=7.8 Hz),7.25(2H,d,J=8.6 Hz),7.36-7.39(2H,m);
mass spectrum (ESI):397(M+H).

Example 69

4-[(3,4-Dichlorobenzyl)oxy]-1-{4-[2-(1-pyrrolidinyl)ethoxy]phenyl}-1H-pyridin-2-one $^1$HNMR(300 MHz,CDCl$_3$,δppm):1.80-1.84(4H,m), 2.62-2.66(4H,m),2.93(2H,t,J=5.9 Hz),4.14(2H,t,J=5.9 Hz), 4.98(2H,s),5.99(1H,d,J=2.7 Hz),6.03(1H,dd,J=7.6,2.7 Hz), 6.99(2H,d,J=8.6 Hz),7.27-7.22(4H,m),7.48(1H,d,J=8.2 Hz), 7.52(1H,d,J=2.0 Hz);
mass spectrum (ESI):459(M+H).

Example 70

4-(2-Naphthylmethoxy)-1-{4-[2-(1-pyrrolidinyl)ethoxy]phenyl}-1H-pyridin-2-one $^1$HNMR(400 MHz,DMSO-d$_6$,δppm):1.66-1.69(4H,m), 2.47-2.53(4H,m),2.78(2H,t,J=6.1 Hz),4.09(2H,t,J=5.9 Hz), 5.30(2H,S),6.01(1H,d,J=2.6 Hz),6.10(1H,dd,J=2.6 Hz,7.6 Hz), 7.00(2H,d,J=8.9 Hz),7.23(2H,d,J=8.9 Hz),7.51-7.58 (4H,m), 7.91-8.01(4H,m);
mass spectrum (ESI):441(M+H).

Example 71

4-(2-Methoxybenzyloxy)-1-{4-[2-(1-pyrrolidinyl)ethoxy]phenyl}-1H-pyridin-2-one $^1$HNMR(400 MHz,DMSO-d$_6$,δppm):1.66-1.69(4H,m), 2.45-2.55(4H,m),2.79(2H,t,J=5.9 Hz),3.82(3H,s), 4.10(2H,t, J=5.9 Hz),5.05(2H,s),5.92(1H,d,J=2.6 Hz), 6.03(1H,dd, J=2.6,7.8 Hz),6.95-7.09(4H,m),7.24(2H,m), 7.34-7.40(2H, m),7.49(1H,d,J=7.8 Hz);
mass spectrum (ESI):421(M+H).

Example 72

4-(3-Methoxybenzyloxy)-1-{4-[2-(1-pyrrolidinyl)ethoxy]phenyl}-1H-pyridin-2-one $^1$HNMR(400 MHz,DMSO-d$_6$,δppm):1.65-1.67(4H,m), 2.45-2.55(4H,m),2.78(2H,t,J=5.9 Hz),3.76(3H,s), 4.09(2H,t, J=5.9 Hz),5.09(2H,s),5.92(1H,d,J=2.8 Hz), 6.06(1H,dd, J=2.8,7.8 Hz),6.92(1H,dd,J=2.7,8.0 Hz), 6.98-7.03(4H,m), 7.23(2H,d,J=6.8 Hz),7.32(1H,t,J=10.2 Hz), 7.51(1H,d,J=7.8 Hz);
mass spectrum (ESI):421(M+H).

Example 73

4-(4-Methoxybenzyloxy)-1-{4-[2-(1-pyrrolidinyl)ethoxy]phenyl}-1H-pyridin-2-one $^1$HNMR(400 MHz,DMSO-d$_6$,δppm):1.64-1.70(4H,m), 2.44-2.54(4H,m),2.78(2H,t,J=5.9 Hz),3.76(3H,s), 4.09(2H,t, J=5.9 Hz),5.03(2H,s),5.94(1H,d,J=2.8 Hz), 6.02(1H,dd, J=2.8,7.8 Hz),6.96(2H,d,J=8.8 Hz), 7.00(2H,d,J=8.8 Hz), 7.23(2H,d,J=8.8 Hz),7.38(2H,d,J=8.8 Hz),7.38(1H,d,J=7.8 Hz);
mass spectrum (ESI):421(M+H).

Example 74

4-(2-Chlorobenzyloxy)-1-{4-[2-(1-pyrrolidinyl) ethoxy]phenyl}-1H-pyridin-2-one

¹HNMR(400 MHz,DMSO-d₆,δppm):1.66-1.69(4H,m), 2.45-2.55(4H,m),2.79(2H,t,J=5.9 Hz),4.10(2H,t,J=5.9 Hz), 5.17(2H,s),5.98(1H,d,J=2.6 Hz),6.06(1H,dd,J=2.6,7.6 Hz), 7.01(2H,d,J=9.0 Hz),7.25(2H,d,J=9.0 Hz),7.39-7.45(2H,m), 7.49-7.52(2H,m),7.60-7.62(1H,m);
mass spectrum (ESI):425(M+H).

Example 75

4-(3-Chlorobenzyloxy)-1-{4-[2-(1-pyrrolidinyl) ethoxy]phenyl}-1H-pyridin-2-one

¹HNMR(400 MHz,DMSO-d₆,δppm):1.62-1.73(4H,m), 2.45-2.55(4H,m),2.78(2H,t,J=6.0 Hz),4.09(2H,t,J=6.0 Hz), 5.14(2H,s),5.94(1H,d,J=2.9 Hz),6.08(1H,dd,J=2.9,7.8 Hz), 7.00(2H,d,J=9.0 Hz),7.23(2H,d,J=9.0 Hz),7.39-7.48(3H,m), 7.50-7.56(2H,m);
mass spectrum (ESI):425(M+H).

Example 76

4-(4-Chlorobenzyloxy)-1-{4-[2-(1-pyrrolidinyl) ethoxy]phenyl}-1H-pyridin-2-one

¹HNMR(400 MHz,DMSO-d₆,δppm):1.64-1.70(4H,m), 2.44-2.54(4H,m),2.78(2H,t,J=5.9 Hz),4.09(2H,t,J=5.9 Hz), 5.12(2H,s),5.93(1H,d,J=2.8 Hz),6.05(1H,dd,J=2.8,7.6 Hz), 7.00(2H,d,J=8.8 Hz),7.23(2H,d,J=8.8 Hz),7.51(4H,s), 7.51 (1H,d,J=7.6 Hz);
mass spectrum (ESI):425(M+H).

Example 77

4-(4-Fluoro-3-hydroxybenzyloxy)-1-{4-[2-(1pyrrolidinyl)ethoxy]phenyl}-1H-pyridin-2-one trifluoroacetate (1) Preparation of 4-fluoro-3-(methoxymethoxy)benzyl alcohol Triethylamine (1.07 mL) and methoxymethyl chloride (2.24 mL) were added to tetrahydrofuran (10 mL) solution of 4-fluoro-3-hydroxybenzoic acid (1.0 g), and stirred at 0° C. for 2 hours. Ethyl acetate was added to the reaction liquid which then was washed with water and saturated brine, dried over anhydrous magnesium sulfate, the solvent therein was concentrated under reduced pressure and the residue was dissolved in tetrahydrofuran (20 mL). Lithiumaluminium hydride (360 mg) was added, stirred at 0° C. for an hour, ethyl acetate was added and the insoluble matter was removed, followed by washing with saturated brine and drying over anhydrous magnesium sulfate. Concentrating the solvent under reduced pressure, the title compound (1.14 g, 94%) was obtained.

(2) Preparation of 4-[4-fluoro-3-methoxymethoxy) benzyloxy]-1-{4-[2-(1-pyrrolidinyl)ethoxy]phenyl}-1H-pyridin-2-one Example 33 was repeated except that 2-hydroxymethyl-5-fluoropyridine was replaced with 4-fluoro-3-methoxymethoxy)benzyl alcohol, to provide the title compound.

(3) Preparation of 4-(4-fluoro-3-hydroxybenzyloxy)-1-{4-[2-(1-pyrrolidinyl)-ethoxy]phenyl}-1H-pyridin-2-one trifluoroacetate 10% Hydrogen chloride-methanol (1 mL) was added to methanol (1 mL) solution of 4-[4-fluoro-3-(methoxymethoxy)benzyloxy]-1-{4-[2-(1-pyrrolidinyl)ethoxy] phenyl}-1H-pyridin-2-one and stirred at room temperature for 3 hours, and at 60° C. for another hour. The reaction liquid was concentrated and purified on HPLC (YMC, pro C-18, 0.1% TFA acetonitrile-water 5% →90%). The effluent was concentrated. The operation cycle of dissolving the residue in ethanol and concentrating the solution was repeated three times, and thereafter ethyl acetate was added to the residue and the formed crystalline product was recovered by filtration, to provide the title compound (121 mg, 63%).

¹HNMR(400 MHz,DMSO-d₆,δppm):1.90(2H,brs), 1.98 (2H,brs),2.49-2.52(2H,m),3.13(2H,brs),3.59(2H,brs), 4.32 (2H,brs),5.02(2H,s),5.92(1H,d,J=2.8 Hz), 6.06(1H,dd,J=7.6, 2.8 Hz),6.85-6.88(1H,m), 7.01(1H,dd,J=8.5,2.2 Hz),7.08 (2H,d,J=8.8 Hz), 7.15(1H,dd, j=11.5,8.5 Hz),7.30(2H,d, J=8.8 Hz), 7.50(1H,d,J=7.6 Hz),9.74(1H,brs),9.97(1H,s);
mass spectrum (ESI):425(M+H).

Example 78

4-(4-Fluorobenzyloxy)-1-{3-methoxy-4-[2-(1-pyrrolidinyl)ethoxy]phenyl}-1H-pyridin-2-one (1) Preparation of 2-(4-bromo-2-methoxyphenoxy)tetrahydro-2H-pyran 3,4-Dihydro-2H-pyran (2.0 mL) and pyridinium p-toluenesulfonate (370 mg) were added to chloroform solution (30 mL) of 4-bromo-2-methoxyphenol (3.0 g) and stirred at room temperature for 12 hours. Saturated brine was added to the reaction liquid, followed by extraction with chloroform. The organic layer was washed with water and dried over anhydrous magnesium sulfate. Concentrating the solvent under reduced pressure, the residue was purified on silica gel column chromatography (C-200; ethyl acetate:hexane=1:19) to provide the title compound (3.64 g, 86%).

(2) Preparation of 4-(4-fluorobenzyloxy)-1-{3-methoxy-4-[2-(1-pyrrolidinyl)-ethoxy]phenyl}-1H-pyridin-2-one Steps (1), (2) and (3) of Example 12 were repeated except that 4-benzyloxy-1H-pyridin-2-one and 2-(4-iodophenyloxy)tetrahydropyran which were used in the Step (1) were replaced with 4-(4-fluorobenzyloxy)-1H-pyridin-2-one and 2-(4-bromo-2-methoxyphenoxy)-tetrahydro-2H-pyran, respectively, to provide the compound.

¹HNMR(300 MHz,CDCl₃,δppm):1.75-1.88(4H,m), 2.55-2.78(4H,m),2.99(2H,t,J=6.3 Hz),3.86(3H,s), 4.21(2H,t, J=6.3 Hz),5.00(2H,s),5.98-6.05(2H,m), 6.84(1H,dd,J=2.3, 8.4 Hz),6.88(1H,d,J=2.3 Hz), 6.96(1H,d,J=8.4 Hz),7.10(2H, t,J=8.8 Hz),7.21-7.29(1H,m), 7.40(2H,dd,J=5.3,8.8 Hz);
mass spectrum (APcI):439.1(M+H).

Example 79

4-Benzyloxy-1-{2-[2-piperidinyl)ethoxy[-5-pyrimidinyl}-1H-pyridin-2-one (1) Preparation of 5-bromo-2-(2,2-diethoxyethoxy)pyrimidine 2,2-Diethoxyethanol (1.6 g) and cesium carbonate (5.8 g) were added to DMF solution (10 mL) of 5-bromo-2-chloropyrimidine (1.15 g), and stirred at room temperature for 12 hours. After addition of water, the reaction liquid was extracted with ethyl acetate and dried over anhydrous magnesium sulfate. Concentrating the solvent under reduced pressure, the residue was purified on silica gel column chromatography (C-200; ethyl acetate:hexane=1:9-1:4) to provide the title compound (1.63 g, 94%).

(2) Preparation of 4-benzyloxy-1-[2-(2,2-diethoxyethoxy)-5-pyrimidinyl}-1H-pyridin-2-one Step (1) of Example 12 was repeated except that 2-(4-iodophenoxy)-tetrahydropyran was replaced with 5-bromo-2-(2,2-diethoxyethoxy)-pyrimidine, to provide the title compound.

(3) Preparation of 4-benzyloxy-1-{2-[2-(1-piperidinyl)ethoxy]-5-pyrimidinyl}-1H-pyridin-2-one Water (0.5 mL) and trifluoroacetic acid (1 mL) were added to chloroform solution (5 mL) of the compound (90 mg) as synthesized in Step (2) of Example 79, and stirred at room temperature for an hour. Concentrating the solvent under reduced pressure, the residue was subjected to azeotropy with toluene. Thereafter piperidine (0.060 mL) and 3M Zn [B(CN)H$_3$]$_2$-methanol solution (5 mL, prepared form zinc chloride and sodium cyanotrihydroborate) were added and stirred at room temperature for 17 hours. Saturated aqueous sodium hydrogencarbonate solution was added to the reaction liquid which then was extracted with chloroform and dried over anhydrous magnesium sulfate. Concentrating the solvent under reduced pressure, the residue was purified on silica gel column chromatography (C-200; methanol:chloroform=1:19-1:10-1:4) and reprecipitated from diethyl ether-hexane to provide the title compound (16 mg, 190%).

$^1$HNMR(300 MHz,CDCl$_3$,δppm):1.41-1.51(2H,m), 1.57-1.70(4H,m),2.52-2.68(4H,m),2.97(2H,t,J=6.1 Hz), 4.58(2H,t,J=6.1 Hz),5.06(2H,s),6.05(1H,d,J=2.6 Hz), 6.13(1H,dd,J=2.6,7.6 Hz),7.18(1H,d,J=7.6 Hz),] 7.28-7.48(5H,m),8.56 (2H,s);

mass spectrum (ESI):407.3(M+H).

Example 80

4-(4-Fluorobenzyloxy)-1-{4-[2-(1-pyrrolidinyl)ethoxy]phenyl}-1H-pyrimidin-2-one (1) Preparation of 2-chloro-4-(4-fluorobenzyloxy)pyrimidine n-Butyl lithium (2.6 M n-hexane solution, 10.1 mL) was added to tetrahydrofuran solution (12 mL) of 4-fluorobenzyl alcohol (3.08 mL) at −78° C., and stirred at the same temperature for 30 minutes. This reaction liquid was gradually added to tetrahydrofuran suspension (24 mL) of 2,4-dichloropyrimidine (4.0 g) and stirred at room temperature for 2 hours. After addition of water, the reaction liquid was extracted with ethyl acetate. The organic layer was washed with saturated brine and dried over anhydrous magnesium sulfate. Concentrating the solvent under reduced pressure, the residue was crystallized from mixed solvent of chloroform and hexane to provide the title compound (4.36 g, 68%).

(2) Preparation of 4-(4-fluorobenzyloxy)-1H-pyrimidin-2-one n-Butyl lithium (2.6 M n-hexane solution, 7.2 mL) was added to tetrahydrofuran solution (10 mL) of 2-popenyl alcohol (1.8 mL) at −78° C., and stirred at the same temperature for 30 minutes. This reaction liquid was gradually added to tetrahydrofuran solution (20 mL) of 2-chloro-4-(4-fluorobenzyloxy)pyrimidine (4.36 g) and stirred at 60° C. for 4 hours, followed by 24 hours' reflux. Cooling the reaction liquid to room temperature, ethyl acetate was added thereto, followed by washing with water and saturated brine and drying over anhydrous magnesium sulfate. Concentrating the solvent under reduced pressure, the residue was dissolved in tetrahydrofiaan (20 mL). To the solution piperidine (2 mL) and tetrakis(triphenylphosphine)palladium (780 mg) were added and stirred at room temperature for 4 hours. The reaction liquid was added to water (100 mL)-ethyl acetate (50 mL) mixture, and the insoluble matter was recovered by filtration to provide the title compound (0.96 g, 24%).

(3) Preparation of 4-(4-fluorobenzyloxy)-1-(4-hydroxyphenyl)-1H-pyrimidin-2-one

Steps (3) and (4) of Example 1 were repeated except that 4-benzyloxy-1H-pyridin-2-one which was used in Step (3) of Example 1 was replaced with 4-(4-fluorobenzyloxy)-1H-pyrimidin-2-one, to provide the title compound.

(4) Preparation of 4-(4-fluorobenzyloxy)-1-{4-[2-(1-pyrrolidinyl)-ethoxy]phenyl}-1H-pyrimidin-2-one Step (3) of Example 12 was repeated except that 4-benzyloxy-1-(4-hydroxyphenyl)-1H-pyridin-2-one was replaced with 4-(4-fluorobenzyloxy)-1-(4-hydroxyphenyl)-1H-pyrimidin-2-one, to provide the title compound.

$^1$HNMR(400 MHz,DMSO-d$_6$,δppm):1.67-1.70(4H,m), 2.51-2.54(4H,m),2.80(2H,t,J=5.9 Hz),4.11(2H,t,J=5.9 Hz), 5.35(2H,s),6.11(1H,d,J=7.3 Hz),7.03(2H,d,J=9.3 Hz), 7.24 (2H,t,J=9.0 Hz),7.31(2H,d,J=9.3 Hz), 7.53(2H,dd,J=8.5,5.6 Hz),7.99(1H,d,J=7.3 Hz);

mass spectrum (ESI):410(M+H).

Example 81

4-(4-Fluorobenzyloxy)-1-{4-[2-diethylamino)ethoxy]phenyl}-1H-pyrimidin-2-one Example 80 was repeated except that 2-(1-pyrrolidine)ethanol as used in Step (4) was replaced with 2-(diethylamino)ethanol, to provide the title compound.

$^1$HNMR(300 MHz,DMSO-d$_6$,δppm):0.97(6H,t,J=7.1 Hz), 2.54(4H,d,J=7.1 Hz),2.77(2H,t,J=6.1 Hz),4.05(2H,t,J=6.1 Hz), 5.35(2H,s),6.10(1H,d,J=7.2 Hz),7.01(2H,d,J=8.9 Hz), 7.23(2H,t,J=8.9 Hz),7.30(2H,d,J=8.9 Hz), 7.51(2H,dd,J=8.7,5.5 Hz),7.98(1H,d,J=7.2 Hz);

mass spectrum (ESI):412(M+H).

Example 82

4-Benzyloxy-1-{4-[2-(1-pyrrolidinyl)ethoxy]phenyl}-1H-pyrimidin-2-one

Example 80 was repeated except that 4-fluorobenzyl alcohol as used in Step (1) was replaced with benzyl alcohol, to provide the title compound.

$^1$HNMR(300 MHz,CDCl$_3$,δppm):1.81-1.85(4H,m), 2.63-2.68(4H,m),2.93(2H,t,J=5.9 Hz),4.15(2H,t,J=5.9 Hz), 5.47 (2H,s),6.00(1H,d,J=7.0 Hz),7.00(2H,d,J=9.0 Hz), 7.28(2H, d,J=9.0 Hz),7.47-7.34(5H,m),7.51(1H,d,J=7.0 Hz);
mass spectrum (ESI):392.3(M+H).

Example 83

6-(4-Fluorobenzyloxy)-3-{4-[2-(1-pyrrolidinyl)ethoxy]phenyl}-3H-pyrimidin-4-one Example 80 was repeated except that 2,4-dichloropyrimidine as used in Step (1) was replaced with 4,6-dichloropyrimidine, to provide the title compound.

$^1$HNMR(300 MHz,DMSO-d$_6$,δppm):1.63-1.70(4H,m), 2.48-2.54(4H,m),2.79(2H,t,J=5.8 Hz),4.11(2H,t,J=5.8 Hz), 5.26(2H,s),5.77(1H,s),7.05(2H,d,J=8.9 Hz),7.23(2H,t,J=8.9 Hz), 7.33(2H,d,J=8.9 Hz),7.50(2H,dd,J=8.6,5.6 Hz),8.37 (1H,s);
mass spectrum (ESI):410(M+H).

Examples 84-87

Step (3) of Example 12 was repeated except that 2-(1-pyrrolidine)ethanol was replaced with corresponding compound in each run, to provide the compounds of Examples 84-87.

Example 84

4-Benzyloxy-1-(4-{2-[(2R)-2-methyl-1-pyrrolidinyl]ethoxy}phenyl)-1H-pyridin-2-one $^1$HNMR(300 MHz,CDCl$_3$,δppm):1.16(3H,d,J=6.1 Hz), 1.38-3.35(9H,m),4.08-4.22(2H,m),5.03(2H,s),5.99-6.07 (2H,m), 6.98(2H,d,J=8.9 Hz),7.18-7.30(3H,m),7.32-7.48 (5H,m);
mass spectrum (ESI):405.3(M+H).

Example 85

4-Benzyloxy-1-(4-{2-[(2S)-2-methyl-1-pyrrolidinyl]ethoxy}phenyl)-1H-pyridin-2-one $^1$HNMR(300 MHz,CDCl$_3$,δppm):1.16(3H,d,J=5.7 Hz), 1.38-2.04(4H,m),221-2.68(3H,m),3.12-3.35(2H,m), 4.05-4.24(2H,m),5.03(2H,s),5.99-6.08(2H,m), 6.98(2H,d,J=9.0 Hz),7.18-7.30(3H,m),7.32-7.47(5H,m);
mass spectrum (ESI):405.3(M+H).

Example 86

1-{4-[2-(7-Azabicyclo[2.2.1]hept-7-yl)ethoxy]phenyl}-4-benzyloxy-1H-pyridin-2-one $^1$HNMR(400 MHz,CD$_3$OD,δppm):1.44-1.52(4H,m), 1.87-1.95(4H,m),2.94-3.00(2H,m),3.56-3.61(2H,m), 4.25 (2H,t,J=5.5 Hz),5.20(2H,s),6.11(1H,d,J=2.4 Hz), 6.29(1H, dd,J=7.6,2.6 Hz),7.08-7.14(2H,m),7.28-7.36(2H,m), 7.37-7.55(6H,m);
mass spectrum (ESI):417(M+H).

Example 87

4-Benzyloxy-1-{4-[(2S,7aR)-hexahydro-1H-pyrrolidin-2-yloxy]phenyl}-1H-pyridin-2-one $^1$ HNMR(300 MHz,CDCl$_3$,δppm):0.85-0.98(1H,m), 1.70-2.15(3H,m),2.32-2.44(1H,m),2.82-2.94(1H,m), 2.99-3.20 (2H,m),3.32-3.45(2H,m),3.57-3.69(1H,m), 4.84-4.93(1H, m),5.04(2H,s),6.00-6.08(2H,m), 6.92(2H,d,J=8.9 Hz),7.19-7.25(3H,m),7.34-7.44(5H,m);
mass spectrum (ESI):403(M+H).

Example 88

4-(4-Fluorobenzyloxy)-1-[4-(2-aminoethoxy)phenyl]-1H-pyridin-2-one (1) Preparation of 4-(4-fluorobenzyloxy)-1-[4-(2-azidoethoxy)phenyl]-1H-pyridin-2-one Step (3) of Example 12 was repeated except that 4-benzyloxy-1-(4-hydroxyphenyl)-1H-pyridin-2-one and 2-(1-pyrrolidine)ethanol were replaced with 4-(4-(fluorobenzyloxy)-1-(4hydroxyphenyl)-1H-pyridin-2-one (Step (2) of Example 28) and 2-azidoethanol, respectively, to provide the title compound.

(2) Preparation of 4-(4-fluorobenzyloxy)-1-[4-(2-aminoethoxy)phenyl]-1H-pyridin-2-one Triphenylphosphine (50 mg) was added to THF (5 mL)-water (1 mL) solution of 4-(4-fluorobenzyloxy)-1-[4-(2-azidoethoxy)phenyl]-1H-pyridin-2-one (50 mg), and stirred at 80° C. for 2 hours. Allowing the reaction liquid to cool off, 1N hydrochloric acid was added, followed by washing with diethyl ether. The aqueous layer was rendered basic by addition of 1N aqueous sodium hydroxide, extracted with chloroform and dried over anhydrous magnesium sulfate. Concentrating the solvent under reduced pressure, the residue was reprecipitated from diethyl ether-hexane to provide the title compound (9.8 mg, 21%).

$^1$HNMR(300 MHz,CDCl$_3$,δppm):3.10(2H,t,J=5.2 Hz), 4.02(2H,t,J=5.2 Hz),4.99(2H,s),6.01(1H,dd,J=2.7,7.6 Hz), 6.04(1H,d,J=2.7 Hz),6.99(2H,d,J=8.9 Hz),7.10(2H,t,J=8.7 Hz), 7.21(1H,d,J=7.6 Hz),7.26(2H,d,J=8.9 Hz), 7.40(2H,dd, J=5.4,8.7 Hz);
mass spectrum (ESI):355.2(M+H).

Example 89

4-(4-Fluorobenzyloxy)-1-(4-{2-[(2S)-2-fluoromethyl-1-pyrrolidinyl]ethoxy}-phenyl)-1H-pyridin-2-one (1) Preparation of tert-butyl (2S)-2-(fluoromethyl)pyrrolidine-1-carboxylate Diethylaminosulfur trifluoride (3.3 g, 20.5 mmols) was added to dichloromethane (30 mL) solution of tert-butyl (2S)-2-(hydroxymethyl)pyrrolidine-1-carboxylate (3.2 g, 15.9 mmols) under cooling with ice, and stirred at the same temperature for 6 hours. The reaction liquid was poured into saturated aqueous sodium hydrogencarbonate solution and extracted with ethyl acetate. Then the organic layer was washed with water and saturated brine and dried over anhydrous sodium sulfate. Concentrating the reaction liquid under reduced pressure, the residue was purified on silica gel column chromatography (C-300; ethyl acetate:hexane=1:20) to provide the title compound (390 mg, 12%).

(2) Preparation of (2S)-2-(fluoromethyl)pyrrolidine hydrochloride 4N hydrogen chloride-ethyl acetate solution (2 mL) was added to tertbutyl (2S)-2-(fluoromethyl)pyrrolidine-1-carboxylate (390 mg), and stirred at room temperature for an hour. Concentrating the reaction liquid under reduced pressure, the title compound (242 mg, 89%) was obtained as a white solid.

(3) Preparation of 2-[(2S)-2-fluoromethyl-1-pyrrolidinyl]ethanol

To chloroform (10 mL) solution of (2S)-2-fluoromethyl) pyrrolidine hydrochloride (242 mg, 1.73 mmols), triethylamine (0.6 mL, 4.33 mmols) and ethyl chloroglyoxylate (0.2 mL, 1.73 mmols) were successively added under cooling with ice, and stirred at the same temperature for 3 hours. After addition of ethyl acetate, the reaction liquid was washed with water and saturated brine and dried over anhydrous sodium sulfate. Concentrating the reaction liquid under reduced pressure, tetrahydrofuran (10 mL) was added to the residue, and to which lithium aluminum hydride (200 mg, 5.27 mmols) was added under cooling with ice, followed by an hour's stirring at room temperature. Sodium sulfate decahydrate (1.0 g) was added to the reaction liquid, diluted with ethyl acetate, and stirred for 3 hours. After drying the system by adding anhydrous sodium sulfate, the reaction liquid was concentrated under reduced pressure to provide the title compound (217 mg, 85%).

(4) Preparation of 4-(4-fluorobenzyloxy)-1-(4-{2-[(2S)-2-fluoromethyl-1-pyrrolidinyl]ethoxy}phenyl)-1H-pyridin-2-one Step (3) of Example 12 was repeated except that 4-benzyloxy-1-(4-hydroxyphenyl)-1H-pyridin-2-one and 2-(1-pyrrolidine)ethanol were replaced with 4-(4-fluorobenzyloxy)-1-(4-hydroxyphenyl)-1H-pyridin-2-one (Step (2) of Example 28) and 2-[(S)-2-fluoromethyl-1-pyrrolidinyl]ethanol, respectively, to provide the title compound.

$^1$HNMR(400 MHz,CDCl$_3$,δppm):1.52-1.72(2H,m), 1.80-1.94(2H,m),2.40-2.50(1H,m),2.54-2.65(2H,m), 2.82-2.95 (3H,m),4.13(2H,t,J=6.0 Hz),4.56-4.78(1H,m), 5.00(2H,s), 6.00-6.05(2H,m),6.97(2H,d,J=8.8 Hz), 7.05-7.13(2H,m), 7.20-7.30(3H,m),7.37-7.7.44(2H,m);

mass spectrum (ESI):441(M+H).

Examples 90-96

Step (3) of Example 12 was repeated except that 4-benzyloxy-1-(4-hydroxyphenyl)-1H-pyridin-2-one and 2-(1-pyrrolidine)ethanol were replaced with 4-(4-fluorobenzyloxy)-1-(4-hydroxyphenyl)-1H-pyridin-2-one (Step (2) of Example 28) and corresponding alcohol compound in each run, to provide the compounds of Example 90-96. Those corresponding alcohol compounds can be obtained using the corresponding compounds in the operations similar to those of Example 89 or methods known from literature or using marketed products.

Example 90

1-{4-[2-(7-Azabicyclo[2.2.1]hept-7-yl)ethoxy]phenyl}-4-(4-fluorobenzyloxy)-1H-pyridin-2-one $^1$HNMR(400 MHz,CD$_3$OD,δppm):1.40-1.48(4H,m), 1.82-1.91(4H,m),2.91(2H,t,J=5.5 Hz),3.49-3.55(2H,m), 4.22(2H,t,J=5.5 Hz),5.15(2H,s),6.10(1H,d,J=2.7 Hz), 6.26 (1H,dd,J=7.8,2.7 Hz),7.11-7.08(2H,m),7.19-7.14(2H,m), 7.30(2H,td,J=6.1,3.6 Hz),7.51(3H,dt,J=9.5,2.5 Hz);

mass spectrum (ESI):435(M+H).

Example 91

1-{4-[2-(8-Azabicylo[3.2.1]oct-8yl)ethoxy]phenyl}-4-(4-fluorobenzyloxy)-1H-pyridin-2-one $^1$HNMR(400 MHz,CD$_3$OD,δppm):1.20-1.97(8H,m), 2.04-2.18(2H,m),2.85-3.06(2H,m),3.43-3.60(2H,m), 4.23 (2H,t,J=5.7 Hz),5.12(2H,s),6.07(1H,d,J=2.7 Hz), 6.24(1H, dd,J=7.6,2.7 Hz),7.04-7.18(4H,m),7.24-7.31(2H,m), 7.44-7.52(3H,m);

mass spectrum (ESI):449(M+H).

Example 92

4-(4-Fluorobenzyloxy)-1-{4-[(2R,7aR)-hexahydro-1H-pyrrolidin-2-yloxy]phenyl}-1H-pyridin-2-one $^1$HNMR(300 MHz,CDCl$_3$,δppm):1.44-1.60(1H,m), 1.64-1.80(1H,m),1.82-1.1.94(2H,m),1.96-2.09(1H,m), 2.24-2.33 (1H,m),2.55-2.63(1H,m),2.86-2.93(1H,m), 3.07-3.18(1H, m),3.32-3.39(1H,m),3.71-3.83(1H,m), 4.94-5.05(3H,m), 5.97-6.08(2H,m),6.92-7.01(2H,m), 7.04-7.15(2H,m),7.17-7.25(3H,m),7.34-7.43(2H,m);

mass spectrum (ESI):421(M+H).

Example 93

1-{4-[2-(3,3-difluoro-1-pyrrolidinyl)ethoxy]phenyl}-4-(4-fluorobenzyloxy-1H-pyridin-2-one $^1$HNMR(300 MHz,CDCl$_3$,δppm):2.23-2.35(2H,m), 2.88 (2H,t,J=7.0 Hz),2.93(2H,t,J=5.5 Hz),3.05(2H,t,J=13.3 Hz), 4.12(2H,t,J=5.5 Hz),4.99(2H,s),6.02(1H,dd,J=7.4,2.7 Hz), 6.04(1H,d,J=2.7 Hz),6.98(2H,d,J=9.0 Hz),7.10(2H,t,J=8.6 Hz), 7.21(1H,d,J=7.4 Hz),7.26(2H,d,J=9.0 Hz), 7.40(2H,dd, J=8.6,5.5 Hz);

mass spectrum (ESI):445(M+H).

Example 94

4-(4-Fluorobenzyloxy)-1-(4-{2-[(3S)-3-fluoro-1-pyrrolidinyl]ethoxy}phenyl)-1H-pyridin-2-one $^1$HNMR(300 MHz,CDCl$_3$,δppm):1.97-3.05(8H,m), 4.14 (2H,t,J=5.7 Hz),4.99(2H,s),5.10-5.28(1H,m), 6.01(1H,dd, J=74,2.7 Hz),6.04(1H,d,J=2.7 Hz), 6.98(2H,d,J=9.0 Hz), 7.10(2H,t,J=8.6 Hz),7.21(1H,d,J=7.4 Hz), 0.26(2H,d,J=9.0 Hz),7.40(2H,dd,J=8.6,5.3 Hz);

mass spectrum (ESI):427(M+H).

Example 95

4-(4-Fluorobenzyloxy)-1-{4-[2-(2-oxo-1-pyrrolidinyl)ethoxy]phenyl}-1H-pyridin-2-one $^1$HNMR(300 MHz,CDCl$_3$,δppm):2.00-2.08(2H,m), 2.40 (2H,t,J=8.0 Hz),3.58(2H,t,J=7.0 Hz),3.70(2H,t,J=5.1 Hz), 4.14(2H,t,J=5.1 Hz),4.99(2H,s),6.00-6.04(2H,m), 6.96(2H, d,J=9.0 Hz),7.10(2H,t,J=8.6 Hz),7.21(1H,d,J=7.4 Hz), 7.26 (2H,d,J=9.0 Hz),7.40(2H,dd,J=8.6,5.5 Hz);
mass spectrum (ESI):423(M+H);
m.p.: 148-149° C.

Example 96

4-(4-Fluorobenzyloxy)-1-(4-{2-[(3R)-3-methoxy-1-pyrrolidinyl]ethoxy}phenyl)-1H-pyridin-2-one $^1$HNMR(300 MHz,CDCl$_3$,δppm):1.79-1.89(1H,m), 2.04-2.14(1H,m),2.56-2.95(6H,m),3.30(3H,s),3.91-3.97(1H,m), 4.14(2H,t,J=5.9 Hz),4.99(2H,s),5.99-6.05(2H,m), 6.98(2H, d,J=8.6 Hz),7.10(2H,t,J=8.6 Hz),7.21(1H,d,J=7.5 Hz), 7.25 (2H,d,J=8.6 Hz),7.39(2H,dd,J=8.6,5.5 Hz);
mass spectrum (ESI):439(M+H).

Examples 97-99

Steps (1) and (2) of Example 28 were repeated except that 4-fluorobenzyl bromide used in the Step (1) was replaced with corresponding halide or sulfonate. Successively Step (3) of Example 12 was repeated using the compounds as obtained in the above runs in place of 4-benzyloxy-1-(4-hydroxyphenyl)-1H-pyridin-2-one and changing 2-(1-pyrrolidine)ethanol to each corresponding compound, to provide the compounds of Examples 97-99.

Example 97

4-(4-Chlorobenzyloxy)-1-(4-{2-[(3R)-3-fluoro-1-pyrrolidinyl]ethoxy}phenyl)-1H-pyridin-2-one $^1$HNMR(400 MHz,CDCl$_3$,δppm):2.00-2.24(2H,m), 2.56-2.64(1H,m),2.80-3.05(5H,m),4.15(2H,t,J=6.0 Hz), 5.00(2H, s),5.10-5.30(1H,m),6.00-6.6.05(2H,m), 6.98(2H,d,J=8.8 Hz),7.20-7.30(3H,m),7.34-7.40(4H,m);
mass spectrum (ESI):443(M+H).

Example 98

4-[(5-fluoro-2-pyridinyl)methoxy]-1-{4-[2-diethylamino)ethoxy]phenyl}-1H-pyridin-2-one $^1$HNMR(300 MHz,DMSO-d$_6$,δppm):0.97(6H,t,J=7.1 Hz), 2.54(4H,q,J=7.1 Hz),2.77(2H,t,J=6.1 Hz),4.04(2H,t, J=6.1 Hz), 5.18(2H,s),5.95(1H,d,J=2.8 Hz),6.09(1H,dd, J=7.6,2.8 Hz), 7.00(2H,d,J=8.9 Hz),7.23(2H,d,J=8.9 Hz), 7.53(1H,d,J=7.6 Hz), 7.63(1H,dd,J=8.8,4.6 Hz),7.81(1H,dt, J=8.8,2.9 Hz), 8.60(1H,d,J=2.9 Hz);
mass spectrum (ESI):412(M+H).

Example 99

4-[(5-fluoro-2-pyridinyl)methoxy]-1-(4-{2-[(2R,5R)-2,5-dimethyl-1-pyrrolidinyl]ethoxy}phenyl)-1H-pyridin-2-one $^1$HNMR(300 MHz,CDCl$_3$,δppm):0.94-1.26(6H,m), 1.23-1.60(2H,m),1.96-2.18(2H,m),2.83-3.30(4H,m), 4.02-4.22 (2H,m),5.15(2H,s),6.01-6.10(2H,m), 6.98(2H,d,J=8.9 Hz), 7.20-7.30(3H,m),7.41-7.53(2H,m), 8.48(1H,d,J=2.1 Hz);
mass spectrum (ESI):438.4(M+H).

Example 100

4-[(5-Chloro-2-pyridinyl)methoxy]-1-{4-[2-dimethylamino)ethoxy]phenyl}-1H-pyridin-2-one (1) Preparation of (5-chloro-2-pyridinyl)methyl methanesulfonate Triethylamine (12 mL) and methanesulfonyl chloride (5.7 mL) were added to tetrahydrofuran (150 mL) solution of 5-chloro-2-hydroxymethylpyridine (12.77 g) under cooling with ice, and stirred for 30 minutes under cooling with ice. After addition of water (150 mL), the reaction liquid was extracted with ethyl acetate (150 mL+150 mL), and the organic layer was washed with saturated brine and dried over anhydrous magnesium sulfate. Concentrating the solvent under reduced pressure, the residue was crystallized from ethyl acetate-diisopropyl ether mixed solvent to provide the title compound (14.65 g, 99%).

(2) Preparation of 4-[(5-chloro-2-pyridinyl)methoxy]-1-[4-2-tetrahydropyranyloxy)phenyl]-1H-pyridin-2-one A mixture of (5-chloropyridin-2-yl)methyl methanesulfonate (14.43 g), 4-hydroxy-1-[4-(2-tetrahydropyranyloxy)phenyl]-1H-pyridin-2-one (15.58 g, Step (1) of Example 27), potassium carbonate (15 g) and N,N-dimethylformamide (500 mL) was stirred at 80° C. for 45 minutes. The reaction liquid was poured into water (1.0 L) and the formed insoluble matter was recovered by filtration. The insoluble matter was dissolved in chloroform and water. The organic layer was washed with saturated brine and dried over anhydrous magnesium sulfate. Concentrating the solvent under reduced pressure, the residue was dissolved in chloroform (50 mL) under reflux. Then ethyl acetate (250 mL) was added and the system was gradually cooled under stirring. The precipitate was recovered by filtration and dried to provide the title compound (18.5 g, 83%).

(3) Preparation of 4-[(5-chloro-2-pyridinyl)methoxy]-1-(4-hydroxyphenyl)-1H-pyridin-2-one Step (2) of Example 12 was repeated except that 4-benzyloxy-1-[4-(2-tetrahydropyranyloxy)phenyl]-1H-pyridin-2-one was replaced with the compound as obtained in Step (2) of Example 100, to provide the title compound.

(4) Preparation of 4-[(5-chloro-2-pyridinyl)methoxy)-1-{4-[2-(dimethylamino)ethoxy]phenyl}-1H-pyridin-2-one Step (3) of Example 12 was repeated except that 4-benzyloxy-1-(4-hydroxyphenyl)-1H-pyridin-2-one and 2-(1-pyrrolidine)ethanol were replaced with the compound as obtained in Step (3) of Example 100 and 2-(diethylamino) ethanol, respectively, to provide the title compound.

¹HNMR(400 MHz,DMSO-d₆,δppm):2.22(6H,s), 2.63 (2H,t,J=5.9 Hz),4.08(2H,t,J=5.9 Hz),5.21(2H,s), 5.94(1H,d, J=2.7 Hz),6.11(1H,dd,J=7.8,2.7 Hz), 7.02(2H,d,J=9.3 Hz), 7.24(2H,d,J=9.3 Hz),7.55(1H,d,J=7.8 Hz), 7.59(1H,d,J=8.3 Hz),8.02(1H,dd,J=8.3,2.4 Hz), 8.67(1H,d,J=2.4 Hz);

mass spectrum (ESI):400(M+H).

Examples 101-107

Example 100 was repeated except that 2-(dimethylamino) ethanol which was used in Step (3) was replaced with corresponding alcohol compound in each run, to provide the compounds of Examples 101-107. Those corresponding alcohol compounds can be obtained using the corresponding compounds in the operations similar to those of Example 89 or methods known from literature or using marketed products.

Example 101

4-[(5-Chloro-2-pyridinyl)methoxy]-1-{4-[2-diethylamino)ethoxy]phenyl}-1H-pyridin-2-one ¹HNMR(400 MHz,DMSO-d₆,δppm):0.98(6H,t,J=7.1 Hz), 2.55(4H,q,J=7.1 Hz),2.78(2H,t,J=6.1 Hz),4.05(2H,t,J=6.1 Hz), 5.21(2H,s),5.94(1H,d,J=2.7 Hz),6.11(1H,dd, J=7.8,2.7 Hz), 7.01(2H,d,J=8.8 Hz),7.24(2H,d,J=8.8 Hz), 7.54(1H,d,J=7.8 Hz), 7.60(1H,d,J=8.3 Hz),8.02(1H,dd, J=8.3,2.4 Hz), 8.67(1H,d,J=2.4 Hz);

mass spectrum (ESI):428(M+H);

m.p.: 112-115° C.

Example 102

4-[(5-Chloro-2-pyridinyl)methoxy]-1-{4-[3-(2-pyrrolidinyl)propoxy]-phenyl}-1H-pyridin-2-one ¹HNMR(300 MHz,CDCl₃,δppm):1.99-2.10(4H,m), 2.39 (2H,t,J=8.2 Hz),3.40-3.52(4H,m),4.01(2H,t,J=6.2 Hz), 5.15 (2H,s),6.01(1H,d,J=2.7 Hz),6.07(1H,dd,J=7.4,2.7 Hz), 6.96 (2H,d,J=8.9 Hz),7.23(1H,d,J=7.4 Hz),7.24(2H,d,J=8.9 Hz), 7.43(1H,d,J=8.3 Hz),7.73(1H,dd,J=8.3,2.4 Hz), 8.58(1H,d, J=2.4 Hz);

mass spectrum (ESI):454(M+H).

Example 103

4-[(5-Chloro-2-pyridinyl)methoxy]-1-(4-{2-[(2R,5R)-2,5-dimethyl-1-pyrrolidinyl]ethoxy}phenyl)-1H-pyridin-2-one ¹HNMR(300 MHz,CDCl₃,δppm):0.92-1.18(6H,m), 1.32-1.55(2H,m),1.92-2.15(2H,m),2.86-3.25(4H,m), 4.02-4.22 (2H,m),5.14(2H,s),6.01(1H,d,J=2.7 Hz), 6.07(1H,dd,J=2.7, 7.6 Hz),6.98(2H,d,J=8.9 Hz), 7.19-7.30(3H,m),7.43(1H,d, J=8.4 Hz),7.73(1H,dd,J=2.5,8.4 Hz), 8.58(1H,d,J=2.5 Hz);

mass spectrum (APcI):454.1(M+H).

Example 104

4-[(5-Chloro-2-pyridinyl)methoxy]-1-(4-{2-[(2R)-2-methyl-1-pyrrolidinyl]-ethoxy}phenyl)-1H-pyridin-2-one ¹HNMR(300 MHz,CDCl₃,δppm):1.14(3H,d,J=6.1 Hz), 1.38-1.52(1H,m),1.65-2.00(3H,m),2.22-2.35(1H,m), 2.35-2.50(1H,m),2.50-2.62(1H,m),3.15-3.30(2H,m), 4.05-4.19 (2H,m),5.15(2H,s),6.02(1H,d,J=2.7 Hz), 6.07(1H,dd,J=2.7, 7.5 Hz),6.98(2H,d,J=8.9 Hz), 7.20-7.32(3H,m),7.43(1H,d, J=8.4 Hz),7.73(1H,dd,J=2.4,8.4 Hz), 8.58(1H,d,J=2.4 Hz);

mass spectrum (ESI):440.2(M+H).

Example 105

4-[(5-Chloro-2-pyridinyl)methoxy]-1-(4-{2-[(3R)-3-fluoro-1-pyrrolidinyl]-ethoxy}phenyl)-1H-pyridin-2-one ¹HNMR(300 MHz,CDCl₃,δppm):2.00-2.26(2H,m), 2.58-3.08(6H,m),4.15(2H,t,J=5.7 Hz),5.10-5.29(1H,m), 5.15(2H, s),6.02(1H,d,J=2.7 Hz),6.07(1H,dd,J=7.6,2.7 Hz), 6.98(2H, d,J=8.6 Hz),7.22-7.28(3H,m),7.43(1H,d,J=8.2 Hz), 7.73(1H, d,J=8.2,2.3 Hz),8.58(1H,d,J=2.3 Hz);

mass spectrum (ESI):444(M+H).

Example 106

4-[(5-Chloro-2-pyridinyl)methoxy]-1-(4-{2-[(3R)-3-methoxy-1-pyrrolidinyl]-ethoxy}phenyl)-1H-pyridin-2-one ¹HNMR(300 MHz,CDCl₃,δppm):1.80-1.89(1H,m), 2.05-2.14(1H,m),2.56-2.95(6H,m),3.30(3H,s),3.92-3.97(1H,m), 4.14(2H,t,J=5.9 Hz),5.15(2H,s),6.02(1H,d,J=2.5 Hz), 6.07 (1H,dd,J=7.6,2.5 Hz),6.98(2H,d,J=8.6 Hz),7.22-7.27(3H, m), 7.43(1H,d,J=8.2 Hz),7.73(1H,dd,J=8.2,2.3 Hz), 8.58 (1H,d,J=2.3 Hz);

mass spectrum (ESI):456.2(M+H).

Example 107

4-[(5-Chloro-2-pyridinyl)methoxy]-1-{4-[2-(diisopropylamino)]ethoxy]phenyl}-1H-pyridin-2-one ¹HNMR(300 MHz,CDCl₃,δppm):1.04(12H,d,J=6.3 Hz), 2.83(2H,t,J=7.4 Hz),3.01-3.08(2H,m),3.91(2H,t,J=7.4 Hz), 5.14(2H,s),6.01(1H,d,J=2.7 Hz),6.06(1H,dd,J=7.6,2.7 Hz), 6.96(2H,d,J=8.6 Hz),7.22-7.26(3H,m),7.43(1H,d,J=8.4 Hz), 7.73(1H,dd,J=8.4,2.5 Hz),8.58(1H,d,J=2.5 Hz);

mass spectrum (ESI):456(M+H).

Example 108

4-[(5-Chloro-2-pyridinyl)methoxy]-1-(4-{2-[(3R)-3-hydroxy-1-pyrrolidinyl]-ethoxy}phenyl)-1H-pyridin-2-one (1) Preparation of 2-((3R)-3-{[tert-butyl(dimethyl) silyl]oxy}-1-pyrrolidinyl)-ethanol Step (3) of Example 89 was repeated except that (S)-2-(fluoromethyl)pyrrolidine hydrochloride was replaced with (3R)-3-{[tert-butyl(dimethyl)silyl]oxy}pyrrolidine, to provide the title compound.

(2) Preparation of 1-{4-[2-((3R)-3-{[tert-butyl(dimethyl)silyl]oxy}-1-pyrrolidinyl)ethoxy]phenyl}-4-[(5-chloro-2-pyridinyl)methoxy]-1H-pyridin-2-one Example 100 was repeated except that 2-(dimethylamino) ethanol used in Step (3) was replaced with 2-((3R)-3-{[tert-butyl(dimethyl)silyl]oxy}-1-pyrrolidinyl)ethanol, to provide the title compound.

(3) Preparation of 4-[(5-chloro-2-pyridinyl)methoxy]-1-(4-{2-[(3R)-3-hydroxy-1-pyrrolidinyl]ethoxy}phenyl)-1H-pyridin-2-one Tetra-n-butylamnunium fluoroide (1.0M THF solution, 0.924 mL, 0.92 mmol) was added to THF (2 mL) solution of 1-{4-[2-((3R)-3-{[tert-butyl(dimethyl)silyl]oxy}-1-pyrrolidinyl)ethoxy]phenyl}-4-[(5-chloro-2-pyridinyl)methoxy]-1H-pyridin-2-one (257.0 mg, 0.46 mmol), and stirred at room temperature for 3 hours. Chloroform was added to the reaction liquid, which then was washed with saturated brine and dried over anhydrous magnesium sulfate. Concentrating the solvent under reduced pressure, the residue was purified on high performance liquid chromatography (YMC-Pack™ pro C-18, 0.1% THF solution: 0.1% TFA acetonitrile solution=10→95%), and the resulting crude title compound was recrystallized fronm ethyl acetate-heptane mixed solvent to provide the title compound (103.1 mg, 50%).

$^1$HNMR(300 MHz,CDCl$_3$,δppm):1.74-1.82(1H,m), 2.17-2.27(1H,m),2.41-2.48(1H,m),2.65-2.69(1H,m), 2.80-2.84 (1H,m),2.93(2H,t,J=5.7 Hz),2.98-3.05(1H,m), 4.14(2H,t, J=5.7 Hz),4.35-4.40(1H,m),5.15(2H,s), 6.02(1H,d,J=2.7 Hz),6.07(1H,dd,J=7.8,2.7 Hz), 6.98(2H,d,J=9.0 Hz),7.22-7.27(3H,m),7.43(1H,d,J=8.2 Hz), 7.73(1H,dd,J=8.2,2.3 Hz), 8.58(1H,d,J=2.3 Hz);

mass spectrum (ESI):442(M+H).

Example 109

4-[(5-Chloro-2-pyridinyl)methoxy]-1-(4-{2-[(3S)-3-hydroxy-1-pyrrolidinyl]-ethoxy{phenyl)-1H-pyridin-2-one

(1) Preparation of 1-[4-(2-bromoethoxy)phenyl]-4-[(5-chloro-2-pyridinyl)-methoxy]-1H-pyridin-2-one A mixture of 4-[(5-chloro-2-pyridinyl)methoxy]-1-(4-hydroxyphenyl)-1H-pyridin-2-one (1.0 g, 3.1 mmols), cesium carbonate (5.0 g, 15 mmols), dibromoethane (5 mL) and DMF (10 mL) was stirred at 80° C. for 14.5 hours. Chloroform was added to the reaction liquid, followed by filtration. Concentrating the solvent under reduced pressure, the residue was purified on silica gel column chromatography (KP-Sil FLASH 25+ M, chloroform:methanol=1:0→100:2) to provide the title compound (1.2 g, 89%).

(2) Preparation of 1-{4-[2-((3S)-3-{[tert-butyl(dimethyl)silyl]oxy}-1-pyrrolidinyl)ethoxy]phenyl}-4-[(5-chloro-2-pyridinyl)methoxy]-1H-pyridin-2-one A mixture of 1-[4(2-bromoethoxy)phenyl]-4-[(5-chloro-2-pyridinyl)methoxy]-1H-pyridin-2-one (300.7 mg, 0.69 mmol), (3S)-3-{[tert-butyl(dimethyl)silyl]oxy}pyrrolidine (417 mg, 2.1 mmols), ethyl (diisopropyl)amine (0.132 mL, 0.76 mmol) and DMF (3.5 mL) was stirred at 60° C. for 14 hours. Adding water, the reaction liquid was filtered. Thus obtained crude title compound was purified on silica gel column chromatography (KP-Sil FLASH 25+M, chloroform: methanol=1:0→10:1) to provide the title compound (276.6 mg, 72%).

(3) Preparation of 4-[(5-chloro-2-pyridinyl)methoxy]-1-(4-{2-[(3S)-3-hydroxy-1-pyrrolidinyl]ethoxy}phenyl)-1H-pyridin-2-one 5N aqueous hydrochloric acid (2.4 mL, 12 mmols) was added to THF (2.4 mL) solution of 1-(4-{2-[(3S)-3-{[tert-butyl(dimethyl)silyl]oxy}-1-pyrrolidinyl]ethoxy]phenyl}-4-[(5-chloro-2-pyridinyl)methoxy]-1H-pyridin-2-one (264.7 mg, 0.48 mmol), and stirred at room temperature for 2 hours. The reaction liquid was neutralized with 1N aqueous sodium hydroxide, extend with chloroform, washed with saturated brine and dried over anhydrous magnesium sulfate. Concentrating the solvent under reduced pressure, the residue was recrystallized from mixed solvent of ethyl acetate and heptane, to provide the title compound (199.8 mg, 95%).

$^1$HNMR(300 MHz,CDCl$_3$,δppm):1.72-1.81(1H,m), 2.17-2.25(1H,m),2.40-2.47(1H,m),2.65-2.69(1H,m), 2.78-2.81 (1H,m),2.92(2H,t,J=5.9 Hz),2.96-3.03(1H,m), 4.13(2H,t, J=5.9 Hz),4.34-4.39(1H,m),5.15(2H,s), 6.02(1H,d,J=2.7 Hz),6.07(1H,dd,J=7.8,2.7 Hz), 6.98(2H,d,J=9.0 Hz),7.22-7.26(3H,m),7.43(1H,d,J=8.4 Hz), 7.73(1H,dd,J=8.4,2.5 Hz), 8.58(1H,d,J=2.5 Hz);

mass spectrum (ESI):442(M+H).

Example 110

4-[(5-Chloro-2-pyridinyl)methoxy]-1-(4-{2-[(3R)-3-(2-fluoroethoxy)-1-pyrrolidinyl]ethoxy}phenyl)-1H-pyridin-2-one

(1) Preparation of tert-butyl (3R)-3-(2-fluoroethoxy)pyrrolidine-1-carboxylate Sodium hydride (55% oiliness, 140 mg, 3.2 mmols) was added to DMF (5 mL) solution of tert-butyl (3R)-3-hydroxypyrrolidine-1-carboxylate (501.2 mg, 2.7 mmols) and stirred at room temperature for 30 minutes, followed by addition of 2-fluoroethyl p-toluenesulfonate (1.17 g, 5.4 mmols) and further 24 hours' stirring at the same temperature. Ethyl acetate was added to the reaction liquid which then was washed with saturated aqueous sodium hydrogencarbonate solution, water and saturated brine, and dried over anhydrous magnesium sulfate. Concentrating the solvent under reduced pressure, the residue was purified on silica gel column chromatography (KP-Sil Sil FLASH 25+M, ethyl acetate:hexane=1:10→2:8) to provide the title compound (253 mg, 41%).

(2) Preparation of 2-[(3R)-3-(2-fluoroethoxy)-1-pyrrolidinyl]ethanol

Steps (2) and (3) of Example 89 were repeated except that tert-butyl (2S)-2-(fluoromethyl)pyrrolidine-1-carboxylate used in the Step (2) was replaced with tert-butyl (3R)-3-(2-fluoroethoxy)pyrrolidine-1-carboxylate, to provide the title compound.

(3) Preparation of 4-[(5-chloro-2-pyridinyl)methoxy]-1-(4-{2-[(3R)-3-(2-fluoroethoxy)-1-pyrrolidinyl]ethoxy}phenyl-1H-pyridin-2-one Step (4) of Example 100 was repeated except that 2-dimethylamino)ethanol used in said Step was replaced with 2-[(3R)-3-2-fluoroethoxy)-1-pyrrolidinyl]ethanol, to provide the title compound.

$^1$HNMR(300 MHz,CDCl$_3$,δppm):1.83-1.92(1H,m), 2.08-2.19(1H,m),2.57-2.98(6H,m),3.59-3.72(2H,m), 4.10-4.16 (3H,m),4.55(2H,dt,J=47.6,4.3 Hz),5.15(2H,s), 6.02(1H,d, J=2.7 Hz),6.07(1H,dd,J=7.8,2.7 Hz), 6.98(2H,d,J=9.0 Hz), 7.22-7.28(3H,m),7.43(1H,d,J=8.2 Hz), 7.73(1H,dd,J=8.2, 2.5 Hz),8.58(1H,d,J=2.5 Hz);

mass spectrum (ESI):488(M+H).

Example 111

4-[(5-Chloro-2-pyridinyl)methoxy]-1-{4-[2-(ethylamino)ethoxy]phenyl}-1H-pyridin-2-one (1) Preparation of tert-butyl(2-{4-[4-[(5-chloro-2-pyridinyl)methoxy]-2-oxopyridin-1(2H)-yl]phenoxy}ethyl)ethylamine-1-carboxylate Example 100 was repeated except that 2-(dimethylamino)ethanol used in Step (3) was replaced with tert-butyl ethyl (2-hydroxyethyl)amine-1-carboxylate, to provide the title compound.

(2) Preparation of 4-[(5-chloro-2-pyridinyl)methoxy]-1-{4-[2-ethylamino)-ethoxy]phenyl}-1H-pyridin-2-one Trifluoroacetic acid (0.969 mL, 13 mmols) was added to chloroform (3 mL) solution of tert-butyl (2-{4-[4-[(5-chloro-2-pyridinyl)methoxy]-2-oxopyridin-1(2H)yl]phenoxy}ethyl)ethylamine-1-carboxylate (421.8 mg, 2.1 mmols), and stirred at room temperature for 4 hour. The reaction liquid was neutralizd with 1N aqueous sodium hydroxide, extracted with chloroform and dried over anhydrous magnesium sulfate. Concentrating the solvent under reduced pressure, the residue was recrystallized from mixed solvent of ethyl acetate and heptane to provide the title compound (157.5 mg, 19%).

$^1$HNMR(300 MHz,CDCl$_3$,δppm):1.16(3H,t,J=7.2 Hz), 2.74(2H,q,J=7.2 Hz),3.03(2H,t,J=5.3 Hz),3.51(1H,brs), 4.11 (2H,t,J=5.3 Hz),5.15(2H,s),6.02(1H,d,J=2.7 Hz), 6.07(1H, dd,J=7.8,2.7 Hz),6.98(2H,d,J=9.0 Hz),7.22-7.27(3H,m), 7.43(1H,d,J=8.2 Hz),7.73(1H,dd,J=8.2,2.3 Hz), 8.58(1H,d,J=2.3 Hz);

mass spectrum (ESI):400(M+H).

Example 112

4-[(5-Chloro-2-pyridinyl)methoxy]-1-(4-{2-[ethyl(propyl)amino]ethoxy}-phenyl)-1H-pyridin-2-one A mixture of 4-[(5-chloro-2-pyridinyl)methoxy]-1-{4-[2-(ethylamino]-ethoxy]phenyl}-1H-pyridin-2-one (20.7 mg, 0.052 mmol), propionaldehyde (ten drops) and 0.3 M Zn[B(CN)H$_3$]$_2$ methanol solution (1 mL, prepared from zinc chloride and sodium cyanotrihydroborate) was stirred at room temperature for ten minutes. To the reaction liquid, 1N aqueous sodium hydroxide was added, followed by extraction with chloroform and drying over anhydrous magnesium sulfate. Concentrating the solvent under reduced pressure, the residue was purified on preparative thin layer chromatography (Kieselgel TM 60 F 254, chloroform:methanol=9:1) to provide the title compound (14.5 mg, 63%).

$^1$HNMR(300 MHz,CDCl$_3$,δppm):0.90(3H,t,J=7.4 Hz), 1.08(3H,t,J=7.0 Hz),1.4-1.56(2H,m),2.51(2H,t,J=7.4 Hz), 2.65(2H,q,J=7.0 Hz),2.90(2H,t,J=6.2 Hz),4.07(2H,t,J=6.2 Hz), 5.15(2H,s),6.02(1H,d,J=2.7 Hz),6.07(1H,dd,J=7.4,2.7 Hz), 6.97(2H,d,J=9.0 Hz),7.22-7.26(3H,m),7.43(1H,d,J=8.4 Hz), 7.73(1H,dd,J=8.4,2.3 Hz),8.58(1H,d,J=2.3 Hz);

mass spectrum (ESI):442(M+H).

Examples 113 and 114

Example 112 was repeated except that propionaldehyde was replaced with corresponding compound in each run to provide the compounds of Examples 113 and 114.

Example 113

4-[(5-Chloro-2-pyridinyl)methoxy]-1-(4-{2-[ethyl(isopropyl)amino]-ethoxy}phenyl)-1H-pyridin-2-one $^1$HNMR(300 MHz,CDCl$_3$,δppm):1.06(6H,d,J=6.6 Hz), 1.10(3H,t,J=7.0 Hz),2.58-2.66(2H,m),2.81-2.88(2H,m), 3.01-3.08(1H,m),3.99-4.06(2H,m),5.15(2H,s), 6.02(1H,d, J=2.7 Hz),6.07(1H,dd,J=7.8,2.7 Hz), 6.97(2H,d,J=9.0 Hz), 7.23-7.26(3H,m),7.43(1H,d,J=8.6 Hz), 7.73(1H,dd,J=8.6, 2.5 Hz),8.58(1H,d,J=2.5 Hz);

mass spectrum (ESI):442(M+H).

Example 114

4-[(5-Chloro-2-pyridinyl)methoxy]-1-(4-{2-[ethyl(methyl)amino]ethoxy}-phenyl)-1H-pyridin-2-one $^1$HNMR(300 MHz,CDCl$_3$,δppm):1.11(3H,t,J=7.2 Hz), 2.36(3H,s),2.56(2H,q,J=7.2 Hz),2.83(2H,t,J=5.9 Hz), 4.11 (2H,t,J=5.9 Hz),5.15(2H,s),6.02(1H,d,J=2.7 Hz), 6.07(1H, dd,J=7.4,2.7 Hz),6.98(2H,d,J=9.0 Hz), 7.23-7.26(3H,m),743 (1H,d,J=8.3 Hz),7.73(1H,dd,J=8.3,2.3 Hz), 8.58(1H,d,J=2.3 Hz);

mass spectrum (ESI):414(M+H).

Example 115

4-[(5-Chloro-2-pyridinyl)methoxy]-1-(4-{2-[isopropyl(methyl)amino]ethoxy}-phenyl)-1H-pyridin-2-one A mixture of 1-[4-(2-bromoethoxy)phenyl]-4-[(5-chloro-2-pyridinyl)methoxy]-1H-pyridin-2-one (1.1 g, 2.6 mmols, Step (1) of Example 109), isopropyl(methyl)amine (0.811 mL, 7.8 mmols) and DMF (2.6 mL) was stirred at 60° C. for 2 days. Water was added to the reaction liquid and filtered. So obtained crude title compound was purified on silica gel column chromatography (KP-Sil FLASH 25+M, chloroform:methanol=1:0→5:1) to provide the title compound (1.1 g, 99%).

$^1$HNMR(300 MHz,CDCl$_3$,δppm):1.06(6H,d,J=6.7 Hz), 2.35(3H,s),2.83(2H,t,J=6.1 Hz),2.87-2.98(1H,m), 4.09(2H,t, J=6.1 Hz),5.14(2H,s),6.01(1H,d,J=2.7 Hz), 6.07(1H,dd, J=7.8,2.7 Hz),6.97(2H,d,J=9.0 Hz),7.22-7.26(3H,m), 7.43 (1H,d,J=8.2 Hz),7.73(1H,dd,J=8.2,2.5 Hz),8.58(1H,d,J=2.5 Hz);

mass spectrum (ESI):428(M+H);

m.p.: 137-138° C.

Example 116

4-[(5-Chloro-2-pyridinyl)methoxy]-1-(4-{2-[methyl(propyl)amino]ethoxy}-phenyl)-1H-pyridin-2-one Example 115 was repeated except that isopropyl(methyl)amine was replaced with propyl(methyl)amine, to provide the title compound.

$^1$HNMR(300 MHz,CDCl$_3$,δppm):0.91(3H,t,J=7.2 Hz), 1.49-1.60(2H,m),2.35(3H,s),2.43(2H,t,J=7.2 Hz), 2.82(2H,t, J=5.9 Hz),4.10(2H,t,J=5.9 Hz),5.15(2H,s), 6.01(1H,d,J=2.7 Hz),6.07(1H,dd,J=7.4,2.7 Hz), 6.98(2H,d,J=9.0 Hz),7.22-7.26(3H,m),7.43(1H,d,J=8.4 Hz),7.73(1H,dd,J=8.4,2.5 Hz), 8.58(1H,d,J=2.5 Hz);

mass spectrum (ESI):428(M+H);

m.p.: 119-123° C.

Examples 117-118

Step (1) of Example 109 was repeated except that 4-[(5-chloro-2-pyridinyl)methoxy]-1-(4-hydroxyphenyl)-1H-pyridin-2-one was replaced with 4(4-fluorobenzyl)-1-(4-hydroxyphenyl)-1H-pyridin-2-one. Whereby obtained compound was used in Example 115, in place of 1-[4-(2-bromoethoxy)phenyl]-4-[(5-chloro-2-pyridinyl)methoxy]-1H-pyridin-2-one, and also isopropyl(methyl)amine was replaced with a corresponding compound in each run. Repeating Example 115 excepting the above two changes, the compounds of Examples 117 and 118 were obtained.

Example 117

4-(4-Fluorobenzyloxy)-1-(4-{2-[methyl(propyl)amino]ethoxy}phenyl)-1H-pyridin-2-one $^1$HNMR(300 MHz,CDCl$_3$,δppm):0.92(3H,t,J=7.2 Hz), 1.49-1.59(2H,m),2.36(3H,s),2.44(2H,t,J=7.8 Hz), 2.83(2H,t, J=5.9 Hz),4.11(2H,t,J=5.9 Hz),4.99(2H,s), 6.01(1H,dd, J=7.4,2.7 Hz),6.04(1H,d,J=2.7 Hz), 6.98(2H,d,J=9.0 Hz), 7.10(2H,t,J=8.6 Hz),7.22(1H,d,J=7.4 Hz), 7.25(2H,d,J=9.0 Hz),7.40(2H,dd,J=8.6,5.5 Hz);

mass spectrum (ESI):411(M+H).

Example 118

4-(4-Fluorobenzyloxy)-1-(4-{2-[isopropyl(methyl)amino]ethoxy}phenyl)-1H-pyridin-2-one $^1$HNMR(300 MHz,CDCl$_3$,δppm):1.07(6H,d,J=6.6 Hz), 2.36(3H,s),2.85(2H,t,J=6.1 Hz),2.90-2.98(1H,m), 4.10(2H,t, J=6.1 Hz),4.99(2H,s),6.01(1H,dd,J=7.5,2.6 Hz), 6.04(1H,d, J=2.6 Hz),6.98(2H,d,J=9.0 Hz),7.10(2H,t,J=8.6 Hz), 7.21 (1H,d,J=7.5 Hz),7.25(2H,d,J=9.0 Hz), 7.40(2H,dd,J=8.6,5.5 Hz);

mass spectrum (ESI):411(M+H).

Example 119

4-[(5-chloro-2-pyridinyl)methoxy]-1-{4-[(2R)-2-(diethylamino)propoxy]-phenyl}-1H-pyridin-2-one and 4-[(5-chloro-2-pyridinyl)methoxy]-1-{4-[(2S)-2-(diethylamino)propoxy]phenyl}-1H-pyridin-2-one (1) Preparation of 4-[(5-chloro-2-pyridinyl)methoxy]-1-[4-(2-oxopropoxy)-phenyl]-1H-pyridin-2-one A mixture of 4-[(5-chloro-2-pyridinyl)methoxy]-1-(4-hydroxyphenyl-1H-pyridin-2-one (111.2 mg, 0.34 mmol), 1-chloroacetone (0.032 mL, 0.41 mmol), potassium carbonate (93 mg, 0.68 mmol) and DMF (1 mL) was stirred at 60° C. for 15 hours. Adding water to the reaction liquid and filtering the same, the title compound (121.0 mg, 93%) was obtained.

(2) Preparation of 4-[(5-chloro-2-pyridinyl)methoxy]-1-{4-([(2R)-2-(diethylamino)propyl]-ethoxy}phenyl)-1H-pyridin-2-one and 4-[(5-chloro-2-pyridinyl)methoxy]-1-(4-{[(2S)-2-(diethylamino)propyl]-ethoxy}phenyl)-1H-pyridin-2-one 0.3M Zn[B(CN)H$_3$]$_2$ methanol solution (2.61 mL, prepared from zinc chloride and sodium cyanotrihydroborate) was added to methanol (0.5 mL) solution of 4-[5-chloro-2-pyridinyl)methoxy]-1-[4-(2-oxopropoxy)phenyl]-1H-pyridin-2-one (98.3 mg, 0.26 mmol) and diethylamine (0.079 mL, 0.77 mmol). Raising the temperature from room temperature to 60° C., the mixture was stirred for 17 hours. Celite was added to the reaction liquid and which was filtered, and so obtained solution was extracted with chloroform, washed with 1N aqueous sodium hydroxide and saturated brine, and dried over anhydrous magnesium sulfate. Concentrating the solvent under reduced pressure, the residue was purified on silica gel column chromatography (KP-Sil FLASH 12+M, chloroform:methanol=1:0→5:1) to provide a racemic modification (121 mg). Further purifying the product on HPLC (CHIRALPAK™ AD, hexane:isopropanol:diethylamine=50:50:0.05) to provide the title compounds (55.9 mg, 50%; 52.2 mg, 46%).

$^1$HNMR(300 MHz,CDCl$_3$,δppm):1.07(6H,t,J=7.2 Hz), 1.14(3H,d,J=6.8 Hz),2.55-2.66(4H,m),3.22-3.30(1H,m), 3.82(1H,dd,J=9.3,7.3 Hz),4.07(1H,dd,J=9.3,5.1 Hz),5.15 (2H,s), 6.02(1H,d,J=2.7 Hz),6.07(1H,dd,J=7.6,2.7 Hz), 6.97 (2H,d,J=8.8 Hz),7.23-7.26(3H,m),7.43(1H,d,J=8.5 Hz), 7.73 (1H,dd,J=8.5,2.4 Hz),8.58(1H,d,J=2.4 Hz);

mass spectrum (ESI):442(M+H).

Example 120

4-[(5-Chloro-2-pyridinyl)methoxy]-1-(4-{[(3R)-1-(tert-butoxycarbonyl)-3-pyrrolidinyl]oxy}phenyl)-1H-pyridin-2-one (1) Preparation of tert-butyl (3S-3-methanesulfonyloxy)pyrrolidine-1-carboxylate Triethylamine (9.67 mL) and methanesulfonyl chloride (5.12 mL) were added to tetrahydrofuran solution (100 mL) of tert-butyl (3S)-3-hydroxypyrrolidine-1-carboxylate (11.8 g) under cooling with ice, followed by an hour's stirring under the same condition. Adding water, the reaction liquid was extracted with ethyl acetate twice. The organic layer was washed with 10% citric acid solution, saturated sodium hydrogencarbonate solution and saturated brine, dried over anhydrous magnesium sulfate and concentrated to provide the title compound (16.8 g).

(2) Preparation of 4-[(5-chloro-2-pyridinyl)methoxy]-1-(4-{[(3R)-1-(tert-butoxycarbonyl)-3-pyrrolidinyl]oxy}phenyl)-1H-pyridin-2-one 4-[(5-chloro-2-pyridinyl)methoxy]-1-(4-hydroxyphenyl)-1H-pyridin-2-one (3.14 g, Step (3) of Example 100), tert-butyl (3S)-3-methanesulfonyloxy)pyrrolidine-1-carboxylate (3.11 g) and potassium carbonate (2.0 g) were stirred in N,N-dimethylformamide (60 mL) overnight at 80° C. The reaction liquid was cooled to room temperature, added with ethyl acetate, washed with water, saturated aqueous sodium bicarbonate solution and saturated brine, and dried over anhydrous magnesium sulfate. Concentrating the solvent under reduced pressure, the residue was purified on silica gel column chromatography (C-300; methanol:chloroform=1:100-1:50) to provide the title compound (3.99 g, 84%).

$^1$HNMR(400 MHz,CDCl$_3$,δppm):1.39(9H,s),1.98-2.25 (2H,m), 3.30-3.50(3H,m),3.50-3.65(1H,m),5.00-5.08(1H, m),5.20(2H,s), 5.93(1H,d,J=2.7 Hz),6.10(1H,dd,J=2.7 Hz,7.6 Hz), 7.02(2H,d,J=8.9 Hz),7.26(2H,d,J=8.9 Hz),7.55 (1H,d,J=7.6 Hz), 7.58(1H,d,J=8.5 Hz),8.01(1H,dd,J=2.5 Hz,8.5 Hz), 8.65(1H,d,J=2.5 Hz);

mass spectrum (ESI):498(M+H).

Example 121

4-[(5-Chloro-2-pyridinyl)methoxy]-1-(4-{[(3R)-3-pyrrolidinyl]oxy}phenyl)-1H-pyridin-2-one Trifluoroacetic acid (20 mL) was added to chloroform solution (20 mL) of 4-[(5-chloro-2-pyridinyl)methoxy]-1-(4-{[(3R)-1-(tert-butoxycarbonyl)-3-pyrrolidinyl]oxy}phenyl)-1H-pyridin-2-one (3.14 g, Example 121), and stirred at room temperature for an hour. After concentrating the reaction liquid, 1N sodium hydroxide solution was added thereto, followed by extraction with chloroform two times. The organic layer was washed with saturated brine, dried over anhydrous potassium carbonate, and the solvent was concentrated under reduced pressure to provide the title compound (2.65 g, 83%).

$^1$HNMR(300 MHz,DMSO-d$_6$,δppm):1.69-1.80(1H,m), 1.76-2.09(1H,m),2.75-2.97(3H,m),3.06(1H,dd,J=12.2 Hz,5.4 Hz), 4.83-4.90(1H,m),5.20(2H,s),5.93(1H,d,J=2.8 Hz), 6.09(1H,dd,J=2.8 Hz,7.6 Hz),6.96(2H,d,J=8.9 Hz), 7.23 (2H,d,J=8.9 Hz),7.54(1H,d,J=7.6 Hz),7.58(1H,d,J=8.3 Hz), 8.00(1H,dd,J=2.5 Hz,8.3 Hz),8.65(1H,d,J=2.5 Hz);

mass spectrum (ESI):398(M+H).

Example 122

4-[(5-Chloro-2-pyridinyl)methoxy]-1-(4-{[(3R)-1-isopropyl-3-pyrrolidinyl]-oxy}phenyl)-1H-pyridin-2-one Acetone (5.4 mL) and 0.3 M Zn[B(CN)H$_3$]$_2$ methanol solution (126 mL, prepared from zinc chloride and sodium cyanotrihydroborate) were added to methanol solution (200 mL) of 4-[(5-chloro-2-pyridinyl)methoxy]-1-4-{[(3R)-3-pyrrolidinyl]oxy}phenyl)-1H-pyridin-2-one (15.0 g, Example 122), and stirred at room temperature for 2 hours. After concentrating the reaction liquid, saturated aqueous sodium hydrogencarbonate solution was added thereto, followed by extraction with chloroform two times. The organic layer was washed with saturated brine and dried over anhydrous magnesium sulfate. Concentrating the solvent under reduced pressure, the residue was purified on silica gel column chromatography (C-300; methanol:chloroform=1:100-1:10-1:4). The purified product was dissolved in hot ethyl acetate, to which heptane was slowly added, followed by gradual cooling to room temperature. Recovering the formed crystalline product by filtration, the title compound was obtained (15.25 g).

$^1$HNMR(400 MHz,DMSO-$_6$,δppm):1.02(3H,d,J=6.3 Hz), 1.03(3H,d,J=6.3 Hz),1.73-1.80(1H,m),2.24-2.28(1H,m), 2.31-2.38(1H,m),241-2.53(1H,m),2.68(1H,dd,J=10.2,2.4 Hz), 2.73-2.75(1H,m),2.89(1H,dd,J=10.2,6.3 Hz),4.86-4.90 (1H,m), 5.21(2H,s),5.94(1H,d,J=2.7 Hz),6.10(1H,dd,J=7.8, 2.7 Hz), 6.96(2H,d,J=8.8 Hz),7.24(2H,d,J=8.8 Hz),7.55(1H, d,J=7.8 Hz), 7.60(1H,d,J=8.6 Hz),8.02(1H,dd,J=8.6,2.7 Hz), 8.67(1H,d,J=2.7 Hz);

mass spectrum (ESI):440(M+H);
m.p.: 154-155° C.

Example 123

4-[(5-Chloro-2-pyridinyl)methoxy]-1-(4-{[(3R)-1-ethyl-3-pyrrolidinyl]-oxy}phenyl)-1H-pyridin-2-one Ethyl methanesulfonate (0.45 mL) was added to acetonitrile solution of 4-[(5-chloro-2-pyridinyl)methoxy]-1-(4-{[(3R)-3-pyrrolidinyl]oxy}phenyl)-1H-pyridin-2-one (1.65 g, Example 122), and stirred at 80° C. for 2 hours. Additional ethyl methanesulfonate (0.45 mL) was added and stirred at 80° C. for further 2 hours, followed by cooling to room temperature. Chloroform was added to the reaction liquid which then was washed with saturated aqueous sodium hydrogencarbonate solution and saturated brine, and dried over anhydrous potassium carbonate. Concentrating the solvent under reduced pressure, the residue was purified on silica gel column chromatography (C-300; methanol:chloroform=1:100-1:10-1:4). The residue was crystallized from mixed solvent of ethyl acetate and heptane to provide the title compound (660 mg).

$^1$HNMR(300 MHz,DMSO-d$_6$,δppm):1.02(3H,d,J=7.2 Hz), 1.73-1.88(1H,m),2.21-2.38(2H,m),2.31-2.38(1H,m), 2.45(1H,q,J=7.2 Hz),2.61-2.74(2H,m), 2.80(1H,dd,J=10.3 Hz,6.1 Hz),4.84-4.93(1H,m),5.20(2H,s), 5.93(1H,d,J=2.7 Hz),6.09(1H,dd,J=7.6,2.7 Hz), 6.95(2H,d,J=8.9 Hz),7.23 (2H,d,J=8.9 Hz),7.54(1H,d,J=7.6 Hz), 7.58(1H,d,J=8.3 Hz), 8.01(1H,dd,J=8.3,2.5 Hz), 8.66(1H,d,J=2.5 Hz);

mass spectrum (ESI):426(M+H);
m.p.: 145-146° C.

Example 124

4-[(5-Chloro-2-pyridinyl)methoxy]-1-(4-{[(3R)-1-methyl-3-pyrrolidinyl]-oxy}phenyl)-1H-pyridin-2-one Example 124 was repeated except that ethyl methanesulfonate was replaced with methyl iodide, to provide the title compound.

$^1$HNMR(300 MHz,DMSO-d$_6$,δppm):1.71-1.85(1H,m), 2.25(3H,s),2.24-2.42(2H,m),2.57-2.73(2H,m), 2.77(1H,dd, J=10.5 Hz,6.1 Hz),4.85-4.93(1H,m),5.20(2H,s), 5.93(1H,d, J=2.8 Hz),6.09(1H,dd,J=7.6,2.9 Hz), 6.94(2H,d,J=8.9 Hz), 7.23(2H,d,J=8.9 Hz),7.53(1H,d,J=7.6 Hz), 7.58(1H,d,J=8.3 Hz),8.01(1H,dd,J=8.3,2.5 Hz), 8.65(1H,d,J=2.5 Hz);

mass spectrum (ESI):412(M+H).

Example 125

4-[(5-Chloro-2-pyridinyl)methoxy]-1-(4-{[(3R)-1-(2-fluoroethyl)-3-pyrrolidin]oxy}phenyl)-1H-pyridin-2-one (1) Preparation of (3S)-1-benzyl-3-acetoxypyrrolidine Triethylamine (1.3 mL, 9.30 mmols) and acetyl chloride (0.6 mL, 8.46) were added to THF (20 mL) solution of (3S)-1-benzyl-3-hydroxypyrrolidine (1.5 g, 8.46 mmols) by the order stated, under cooling with ice, and stirred at the same temperature for an hour. Ethyl acetate was added to the reaction liquid which then was washed with water and saturated brine, and dried over anhydrous sodium sulfate. Concentrating the reaction liquid under reduced pressure, the residue was purified on silica gel column chromatography (KP—NH, ethyl acetate:hexane=1:20) to provide the title compound (1.68 g, 90%).

(2) Preparation of (3S)-1-(2-fluoroethyl)-3-acetoxypyrrolidine

Palladium hydroxide (170 mg) was added to methanol (30 mL) solution of (3S)-1-benzyl-3-acetoxypyrrolidine (1.68 g, 7.62 mmols), and after substituting the atmosphere with hydrogen gas, the reaction system was stirred for a day and night Celite-filtering the reaction liquid, the filtrate was concentrated under reduced pressure. So obtained crude product was dissolved in acetonitrile (20 mL) and to the solution potassium carbonate (1.58 g, 11.43 mmols) and 2-fluoromethyl trifluoromethanesulfonate (1.42 g, 7.24 mmols) were added, followed by an hour's stirring at room temperature. The reaction liquid was filtered, concentrated under reduced pressure, and the residue was purified on silica gel column chromatography (P-Sil, ethyl acetate:hexane:triethylamine=1:1:0.01) to provide the title compound (507 mg, 38%).

(3) Preparation of (3S)-1-(2-fluoroethyl)-3-hydroxypyrrolidine 4N aqueous sodium hydroxide solution (2 mL) was added to methanol (10 mL) solution of (3S)-1-(2-fluoroethyl)-3-acetoxypyrrolidine (507 mg, 2.89 mmols), and stirred at room temperature for an hour. The reaction liquid was concentrated under reduced pressure, extracted with chloroform and dried over anhydrous sodium sulfate. Concentrating the reaction liquid under reduced pressure, the title compound (135 mg, 35%) was obtained.

(4) Preparation of 4-[(5-chloro-2-pyridinyl)methoxy]-1-(4-{[(3R)-1-(2-fluoroethoxy)-3-pyrrolidinyl]oxy}phenyl)-1H-pyridin-2-one Example 121 was repeated except that tert-butyl (3S)-3-hydroxypyrrolidine-1-carboxylate was replaced with (3S)-1-(2-fluoroethyl)-3-hydroxypyrrolidine, to provide the title compound.

$^1$HNMR(400 MHz,CDCl$_3$,δppm):1.98-2.06(1H,m), 2.30-2.38(1H,m),2.61-2.68(1H,m),2.78-2.93(4H,m), 3.00-3.07 (1H,m),4.60(2H,dt,J=4.8 Hz,47.6 Hz),4.80-4.88(1H,m), 5.15(2H,s),6.01(1H,d,J=2.4 Hz),6.07(1H,dd,J=2.8 Hz,7.6 Hz), 6.91(2H,d,J=8.8 Hz),7.20-7.28(3H,m),7.43(1H,d,J=8.8 Hz), 7.73(1H,dd,J=2.4 Hz,8.4 Hz),8.58(1H,d,J=2.0 Hz);

mass spectrum (ESI):444(M+H).

Example 126

4-[5-Chloro-2-pyridinyl)methoxy]-1-(4-{[(3R)-1-(methanesulfonyl)-3-pyrrolidinyl]oxy}phenyl)-1H-pyridin-2-one Triethylamine (0.0116 mL) and methanesulfonyl chloride (0.0064 mL) were added to N,N-dimethylformamide solution (1 mL) of 4-[5-chloro-2-pyridinyl)methoxy]-1-(4-{[(3R)-3-pyrrolidinyl]oxy}phenyl)-1H-pyridin-2-one (30 mg, Example 122) under cooling with ice, and stirred for an hour under the same condition. Adding water, the reaction liquid was extracted with ethyl acetate. The organic layer was washed with 10% citric acid solution, saturated sodium hydrogencarbonate solution and saturated brine, dried over anhydrous magnesium sulfate, concentrated, and the residue was crystallized from mixed solvent of ethyl acetate and hexane to provide the title compound (28 mg).

$^1$HNMR(300 MHz,DMSO-d$_6$,δppm):2.05-2.15(1H,m), 2.17-2.31(1H,m),2.91(3H,s),3.34-3.44(3H,m), 3.60(1H,dd, J=11.8 Hz,4.3 Hz),5.06-5.12(1H,m),5.20(2H,s), 5.93(1H,d, J=2.6 Hz),6.10(1H,dd,J=7.6,2.6 Hz), 7.04(2H,d,J=8.9 Hz), 7.27(2H,d,J=8.9 Hz),7.55(1H,d,J=7.6 Hz), 7.58(1H,d,J=8.3 Hz),8.01(1H,dd,J=8.3,2.5 Hz), 8.66(1H,d,J=2.5 Hz);

mass spectrum (ESI):476(M+H).

Example 127

4-[(5-Chloro-2-pyridinyl)methoxy]-1-(4-{[(3R)-1-acetyl-3-pyrrolidinyl]-oxy}phenyl)-1H-pyridin-2-one Example 126 was repeated except that methanesulfonyl chloride was replaced with acetic anhydride, to provide the title compound.

$^1$HNMR(300 MHz,DMSO-d$_6$,δppm):1.93(1.2H,s),1.97 (1.8H,s), 2.03-2.30(2H,m),348-3.67(3.6H,m), 3.82(0.4H,dd, J=11.7 Hz,4.7 Hz),5.02-5.09(0.6H,m), 5.10-5.17(0.4H,m), 5.20(2H,s),5.94(1H,d,J=2.6 Hz), 6.07-6.14(1H,m),6.98-7.08 (2H,m),7.22-7.30(2H,m), 7.51-7.55(1H,m),7.59(1H,d,J=8.3 Hz),8.01(1H,dd,J=8.3,2.4 Hz), 8.66(1H,d,J=2.4 Hz);

mass spectrum (ESI):440(M+H).

Example 128

4-[(5-Chloro-2-pyridinyl)methoxy]-1-(4-{[(2R)-1-(tert-butoxycarbonyl)-2-pyrrolidinyl]methoxy}phenyl)-1H-pyridin-2-one Example 120 was repeated except that tert-butyl (3S)-3-hydroxypyrrolidine-1-carboxylate was replaced with tert-butyl (2R)-2-(hydroxymethyl)pyrrolidine-1-carboxylate, to provide the title compound.

$^1$HNMR(300 MHz,DMSO-d$_6$,δppm):1.40(9H,s), 1.72-2.05(4H,m),3.20-3.40(2H,m),3.85-4.13(3H,m),5.20(2H,s), 5.93(1H,d,J=2.8 Hz),6.10(1H,dd,J=7.6 Hz,2.8 Hz), 7.03(2H, d,J=8.8 Hz),7.24(2H,d,J=8.8 Hz),7.52(1H,d,J=7.6 Hz), 7.58 (1H,d,J=8.4 Hz),8.01(1H,dd,J=8.4 Hz,2.5 Hz), 8.65(1H,d, J=2.5 Hz);

mass spectrum (ESI):512(M+H).

Example 129

4-[(5-Chloro-2-pyridinyl)methoxy]-1-(4-{[(2R)-2-pyrrolidinyl]methoxy}phenyl)-1H-pyridin-2-one Example 121 was repeated except that 4-[(5-chloro-2-pyridinyl)methoxy]-1-(4-{[(3R)-1-tert-butoxycarbonyl)-3-pyrrolidinyl]oxy}phenyl)-1H-pyridin-2-one was replaced with 4-[(5-chloro-2-pyridinyl)methoxy]-1-(4-{[(2R)-1-(tert-butoxycarbonyl)-2-pyrrolidinyl]methyloxy}phenyl)-1H-pyridin-2-one to provide the title compound.

$^1$HNMR(300 MHz,DMSO-d$_6$,δppm):1.38-1.51(1H,m), 1.55-1.77(2H,m),1.78-1.90(1H,m),2.74-2.84(2H,m), 3.33-3.43(1H,m),3.79-3.88(2H,m),5.20(2H,s), 5.93(1H,d,J=2.8 Hz),6.09(1H,dd,J=7.6 Hz,2.8 Hz), 6.99(2H,d, 3.0 Hz),7.23 (2H,d,J=9.0 Hz),7.53(1H,d,J=7.6 Hz), 7.58(1H,d,J=8.4 Hz), 8.01(1H,dd,J=8.4 Hz,2.5 Hz), 8.65(1H,d,J=2.5 Hz);

mass spectrum (ESI):412(M+H).

Example 130

4-[(5-Chloro-2-pyridinyl)methoxy]-1-(4-{[(2S)-2-pyrrolidinyl]methoxy}phenyl)-1H-pyridin-2-one Example 120 was repeated except that tert-butyl (3S)-3-hydroxypyrrolidine-1-carboxylate was replaced with tert-butyl (2S)-2-(hydroxymethyl)pyrrolidine-1-carboxylate. The resulting compound was used in placed of 4-[(5-chloro-2-pyridinyl)methoxy]-1-(4-{[(3R)-1-(tert-butoxycarbonyl)-3-pyrrolidinyl]oxy}phenyl)-1H-pyridin-2-one which was used in Example 121. Otherwise repeating Example 121, the title compound was obtained.

¹HNMR(400 MHz,CDCl₃,δppm):1.51-1.60(1H,m), 1.78-1.83(2H,m),1.89-1.99(1H,m),2.94-2.97(1H,m), 2.99-3.06(1H,m),3.47-3.56(1H,m),3.88(1H,dd,J=9.3,6.8 Hz), 3.94(1H,dd,J=9.3,4.8 Hz),5.15(2H,s),6.01(1H,d,J=2.8 Hz), 6.07(1H,dd,J=7.6,2.8 Hz),6.98(2H,d,J=8.8 Hz), 7.23(2H,d,J=7.6 Hz),7.24(1H,d,J=8.8 Hz),7.43(1H,d,J=8.3 Hz), 7.73(1H,dd,J=8.3,2.4 Hz),8.58(1H,d,J=2.4 Hz);

mass spectrum (ESI):412(M+H).

Examples 131-134

Example 122 was repeated except that 4-[(5-chloro-2-pyridinyl)methoxy]-1-(4-{(3R)-3-pyrrolidinyl}oxy}phenyl)-1H-pyridin-2-one and acetone were replaced with each corresponding 4-[(5-chloro-2-pyridinyl)methoxy]-1-(4-{[(2S)-2-pyrrolidinyl]methoxy}phenyl)-1H-pyridin-2-one or 4-[(5-chloro-2-pyridinyl)methoxy]-1-(4-{[(2R)-pyrrolidin-2-yl]methoxy}phenyl)-1H-pyridin-2-one and acetone, cyclobutanone or 37% formamide solution, to provide the compounds of Examples 131-134.

Example 131

4-[5-Chloro-2-pyridinyl]methoxy]-1-(4-{[(2S)-1-isopropyl-2-pyrrolidinyl]-methoxy}phenyl)-1H-pyridin-2-one ¹HNMR(300 MHz,DMSO-d₆,δppm):0.97(3H,d,J=6.4 Hz), 1.05(3H,d,J=6.4 Hz),1.63-1.95(4H,m),2.45-2.55(1H,m), 2.79-2.87(1H,m),2.89-3.00(1H,m),3.07-3.15(1H,m), 3.67(1H,dd,J=9.4,8.2 Hz),3.85(1H,dd,J=9.4,4.5 Hz),5.20(2H,s), 5.93(1H,d,J=2.8 Hz),6.09(1H,dd,J=7.7 Hz,2.8 Hz), 6.99(2H,d,J=9.0 Hz),7.22(2H,d,J=9.0 Hz),7.52(1H,d,J=7.7 Hz), 7.58(1H,d,J=8.3 Hz),8.01(1H,dd,J=8.3 Hz,2.6 Hz), 8.65(1H,d,J=2.6 Hz);

mass spectrum (ESI):454(M+H).

Example 132

4-[5-Chloro-2-pyridinyl]methoxy]-1-(4-{[(2R)-1-isopropyl-2-pyrrolidinyl]-methoxy}phenyl)-1H-pyridin-2-one ¹HNMR(300 MHz,DMSO-d₆,δppm):0.98(3H,d,J=6.4 Hz), 1.05(3H,d,J=6.4 Hz),1.63-1.87(4H,m),2.48-2.55(1H,m), 2.79-2.87(1H,m),2.89-3.00(1H,m),3.05-3.15(1H,m), 3.67(1H,dd,J=9.4,8.2 Hz),3.85(1H,dd,J=9.4,4.5 Hz),5.20(2H,s), 5.93(1H,d,J=2.8 Hz),6.10(1H,dd,J=7.6 Hz,2.8 Hz), 6.99(2H,d,J=9.0 Hz),7.22(2H,d,J=9.0 Hz),7.52(1H,d,J=7.6 Hz), 7.58(1H,d,J=8.3 Hz),8.01(1H,dd,J=8.3 Hz,2.6 Hz), 8.65(1H,d,J=2.6 Hz);

mass spectrum (ESI):454(M+H).

Example 133

4-[5-Chloro-2-pyridinyl]methoxy]-1-(4-{[(2R)-1-cyclobutyl-2-pyrrolidinyl]-methoxy}phenyl)-1H-pyridin-2-one ¹HNMR(300 MHz,DMSO-d₆,δppm):1.52-1.72(5H,m), 1.80-2.06(5H,m),2.29-2.29(1H,m),2.82-2.93(2H,m), 3.15-3.28(1H,m),3.71(1H,dd,J=9.4,7.5 Hz), 3.89(1H,dd,J=9.4,4.7 Hz),5.20(2H,s),5.93(1H,d,J=2.8 Hz), 6.09(1H,dd,J=7.6 Hz,2.8 Hz),6.99(2H,d,J=8.9 Hz), 7.23(2H,d,J=8.9 Hz),7.53(1H,d,J=7.6 Hz),7.58(1H,d,J=8.2 Hz), 8.01(1H,dd,J=8.2 Hz,2.4 Hz),8.65(1H,d,J=2.4 Hz);

mass spectrum (ESI):466(M+H).

Example 134

4-[(5-Chloro-2-pyridinyl)methoxy]-1-(4-{[(2S)-1-methyl-2-pyrrolidinyl]-methoxy}phenyl)-1H-pyridin-2-one ¹HNMR(400 MHz,DMSO-d₆,δppm):1.54-1.62(1H,m), 1.64-1.72(2H,m),1.90-2.01(1H,m),2.18(1H,q,J=8.6 Hz), 2.35(3H,s),2.56(1H,ddd,J=12.9,7.1,4.6 Hz),2.92-2.97(1H,m), 3.85(1H,dd,J9.8,5.9 Hz),4.00(1H,dd,J=9.8,5.4 Hz),5.20(2H,s), 5.93(1H,d,J=2.9 Hz),6.10(1H,dd,J=7.8,2.9 Hz), 7.00(2H,d,J=9.0 Hz),7.23(2H,d,J=9.0 Hz),7.53(1H,d,J=7.8 Hz), 7.59(1H,d,J=8.3 Hz),8.01(1H,dd,J=8.3,2.4 Hz), 8.66(1H,d,J=2.4 Hz);

mass spectrum (ESI):426(M+H).

Example 135

4-[(5-Chloro-2-pyridinyl)methoxy]-1-(4-{[(2S)-1-ethyl-2-pyrrolidinyl]-methoxy}phenyl)-1H-pyridin-2-one Example 123 was repeated except that 4-[(5-chloro-2-pyridinyl)methoxy]-1-4-{(3R)-3-pyrrolidinyl]oxy}phenyl)-2H-pyridin-2-one was replaced with 4-[(5-chloro-2-pyridinyl)methoxy]-1-(4-{[(2S)-2-pyrrolidinyl]methoxy}phenyl)-1H-pyridin-2-one, to provide the title compound.

¹HNMR(300 MHz,DMSO-d₆,δppm):1.02(1H,t,J=7.2 Hz) 1.54-1.74(3H,m),1.85-1.97(1H,m),2.12-2.22(1H,m), 2.28-2.37(1H,m),2.70-2.83(1H,m),2.85-2.96(1H,m), 3.01-3.08(1H,m),3.78(1H,dd,J=9.6,6.8 Hz), 3.97(1H,dd,J=9.6,5.0 Hz),5.20(2H,s),5.93(1H,d,J=2.7 Hz), 6.09(1H,dd,J=7.6,2.7 Hz),7.00(2H,d,J=8.9 Hz), 7.23(2H,d,J=8.9 Hz),7.53(1H,d,J=7.6 Hz),7.58(1H,d,J=8.4 Hz), 8.01(1H,dd,J=8.4,2.5 Hz),8.66(1H,d,J=2.5 Hz);

mass spectrum (ESI):440(M+H).

Examples 136, 137

Example 126 was repeated except that 4-[(5-chloro-2-pyridinyl)-methoxy]-1-4-{[(3R)-3-pyrrolidinyl]oxy}phenyl)-1H-pyridin-2-one and methanesulfonyl chloride were replaced with 4-[(5-chloro-2-pyridinyl)-methoxy]-1-(4-{[(2S)-2-pyrrolidinyl]methoxy}phenyl)-1H-pyridin-2-one or 4-[(5-chloro-2-pyridinyl)methoxy]-1-(4-{[(2R)-2-pyrrolidinyl]methoxy}-phenyl)-1H-pyridin-2-one, respectively, and with corresponding acid anhydride, to provide the compounds of Examples 136 and 137.

Example 136

4-[(5-Chloro-2-pyridinyl)methoxy]-1-(4-{[(2S)-1-acetyl-2-pyrrolidinyl]-methoxy}phenyl)-1H-pyridin-2-one ¹HNMR(300 MHz,DMSO-d₆,δppm):1.80-2.15(7H,m), 3.30-3.55(2H,m),3.85-4.35(3H,m),5.20(2H,s), 5.93(1H,d,J=2.7 Hz),6.09(1H,dd,J=7.6,2.7 Hz),7.05(2H,d,J=9.0 Hz), 7.23(2H,d,J=9.0 Hz),7.53(1H,d,J=7.6 Hz),7.58(1H,d,J=8.3 Hz), 8.01(1H,dd,J=8.3,2.5 Hz),8.65(1H,d,J=2.5 Hz);

mass spectrum (ESI):454(M+H).

Example 137

4-[(5-Chloro-2-pyridinyl)methoxy]-1-(4-{[(2R)-1-isobutyryl-2-pyrrolidinyl]-methoxy}phenyl)-1H-pyridin-2-one $^1$HNMR(300 MHz,DMSO-d$_6$,δppm):0.95-1.05(6H,m), 1.80-2.10(4H,m),2.60-2.75(1H,m),3.30-3.55(2H,m), 3.85-4.40(3H,m),520(2H,s),5.93(1H,d,J=2.8 Hz), 6.09(1H,dd, J=7.7,2.8 Hz),7.06(2H,d,J=8.9 Hz), 7.23(2H,d,J=8.9 Hz), 7.52(1H,d,J=7.7 Hz),7.58(1H,d,J=8.3 Hz), 8.01(1H,dd, J=8.3,2.5 Hz),8.65(1H,d,J=2.5 Hz);
mass spectrum (ESI):482(M+H).

Examples 138-143

Example 119 was repeated except that diethylamine was replaced with corresponding amine in each run, to provide racemic modifications of Examples 138-143. The racemic modifications were then separated and purified with CHIRALPAK™ AD, CHIRALPAK™ AS, CHIRALPAK™ IA, CHIRALCEL™ OD, CHIRALCEL™ OJ and the like, to provide the compounds of Examples 138-143.

Example 138

4-[(5-Chloro-2-pyridinyl)methoxy]-1-(4-{(2R)-2-[ethyl(methyl)amino]-propoxy}phenyl)-1H-pyridin-2-one and 4-[(5-chloro-2-pyridinyl)methoxy]-1-(4-{(2S)-2-[ethyl(methyl)amino]propoxy}phenyl)-1H-pyridin-2-one $^1$HNMR(400 MHz,CDCl$_3$,δppm):1.10(3H,t,J=7.0 Hz), 1.15(3H,d,J=6.8 Hz),2.33(3H,s),2.60(2H,q,J=7.0 Hz), 3.14-3.20(1H,m),3.86(1H,dd,J=9.2,6.5 Hz), 4.08(1H,dd,J=9.2,5.4 Hz),5.15(2H,s),6.02(1H,d,J=2.8 Hz), 6.07(1H,dd,J=7.7,2.8 Hz),6.98(2H,d,J=9.0 Hz),7.22-7.26(3H,m), 7.43(1H,dd, J=8.3,0.5 Hz),7.73(1H,dd,J=8.3,2.4 Hz), 8.58(1H,dd,J=2.4, 0.5 Hz);
mass spectrum (ESI):428(M+H).

Example 139

4-[(5-Chloro-2-pyridinyl)methoxy]-1-{4-[(2R)-2-(dimethylamino)propoxy]-phenyl}-1H-pyridin-2-one and 4-[(5-chloro-2-pyridinyl)methoxy]-1-{4-[(2S)-2-(dimethylamino)propoxy]phenyl}-1H-pyridin-2-one $^1$HNMR(400 MHz,CDCl$_3$,δppm):1.15(3H,d,J=6.8 Hz), 2.37(6H,s),2.97-3.02(1H,m),3.87(1H,dd,J=9.5,5.9 Hz), 4.06 (1H,dd,J=9.5,5.9 Hz),5.15(2H,s),6.02(1H,d,J=2.7 Hz), 6.07 (1H,dd,J=7.6,2.7 Hz),6.99(2H,d,J=9.0 Hz),7.23-7.26(3H, m), 7.43(1H,dd,J=8.5,0.7 Hz),7.73(1H,dd,J=8.5,2.4 Hz), 8.58(1H,dd,J=2.4,0.7 Hz);
mass spectrum (ESI):414(M+H).

Example 140

4-[(5-Chloro-2-pyridinyl)methoxy]-1-(4-{(2R)-2-[methyl(propyl)amino]-propoxy]phenyl)-1H-pyridin-2-one and 4-[(5-chloro-2-pyridinyl)methoxy]-1-(4-{(2S)-2-[methyl(propyl)amino]propoxy]phenyl)-1H-pyridin-2-one $^1$HNMR(400 MHz,CDCl$_3$,δppm):0.91(3H,t,J=7.3 Hz), 1.13(3H,d,J=6.6 Hz),1.45-1.55(2H,m),2.32(3H,s), 2.43-2.48 (2H,m),3.12-3.17(1H,m),3.84(1H,dd,J=9.3,6.6 Hz), 4.08 (1H,dd,J=9.3,5.6 Hz),5.15(2H,s),6.02(1H,d,J=2.7 Hz), 6.07 (1H,dd,J=7.6,2.7 Hz),6.98(2H,d,J=9.0 Hz),7.23-7.26(3H, m), 7.43(1H,dd,J=8.3,0.7 Hz),7.73(1H,dd,J=8.3,2.4 Hz), 8.58(1H,dd,J=2.4,0.7 Hz);
mass spectrum (ESI):442(M+H).

Example 141

4-[(5-Chloro-2-pyridinyl)methoxy]-1-(4-{(2R)-2-[isopropyl(methyl)amino]-propoxy]phenyl)-1H-pyridin-2-one and 4-[(5-chloro-2-pyridinyl)methoxy]-1-(4-{(2S)-2-[isopropyl(methyl)amino]propoxy]phenyl)-1H-pyridin-2-one $^1$HNMR(400 MHz,CDCl$_3$,δppm):1.07(3H,d,J=6.6 Hz), 1.09(3H,d,J=6.6 Hz),1.17(3H,d,J=6.6 Hz),229(3H,s), 2.94-3.03(1H,m),3.19-3.28(1H,m),3.77-3.83(1H,m), 4.01-4.06 (1H,m),5.15(2H,s),6.02(1H,d,J=2.7 Hz), 6.07(1H,dd,J=7.6, 2.7 Hz),6.97(2H,d,J=9.0 Hz), 7.22-7.26(3H,m),7.43(1H,d, J=8.4 Hz),7.73(1H,dd,J=8.4,2.6 Hz), 8.58(1H,dd,J=2.6 Hz);
mass spectrum (ESI):442(M+H).

Example 142

4-[(5-Chloro-2-pyridinyl)methoxy]-1-{4-[(2R)-2-(1-pyrrolidinyl)propoxy]-phenyl}-1H-pyridin-2-one and 4-[(5-chloro-2-pyridinyl)methoxy]-1-{4-[(2S)-2-(1-pyrrolidinyl)propoxy]phenyl}-1H-pyridin-2-one $^1$HNMR(400 MHz,CDCl$_3$,δppm):1.28(3H,d,J=6.6 Hz), 1.79-1.84(4H,m),2.64-2.77(5H,m),3.92(1H,dd,J=9.5,6.0 Hz), 4.10(1H,dd,J=9.5,4.4 Hz),5.14(2H,s),6.02(1H,d,J=2.7 Hz), 6.07(1H,dd,J=7.7,2.7 Hz),6.99(2H,d,J=9.0 Hz),7.22-7.26(3H,m), 7.43(1H,dd,J=8.4,0.7 Hz),7.73(1H,dd,J=8.4,2.6 Hz), 8.58(1H,dd,J=2.6,0.7 Hz);
mass spectrum (ESI):440(M+H).

Example 143

4-[(5-Chloro-2-pyridinyl)methoxy]-1-{4-[(2R)-2-(ethylamino)propoxyl]-phenyl}-1H-pyridin-2-one and 4-[(5-chloro-2-pyridinyl)methoxy]-1-{4-[(2S)-2-(ethylamino)propoxy]phenyl}-1H-pyridin-2-one $^1$HNMR(400 MHz,CDCl$_3$,δppm):1.16(3H,t,J=7.1 Hz), 1.18(3H,d,J=6.3 Hz),1.60(1H,brs),2.65-2.81(2H,m), 3.11-3.17(1H,m),3.86-3.93(2H,m),5.15(2H,s), 6.02(1H,d,J=2.7 Hz),6.07(1H,dd,J=7.6,2.7 Hz), 6.98(2H,d,J=9.0 Hz),7.22-7.26(3H,m),7.43(1H,dd,J=8.3,0.7 Hz), 7.73(1H,dd,J=8.3,2.4 Hz),8.58(1H,dd,J=2.4,0.7 Hz);
mass spectrum (ESI):414(M+H).

Examples 144-151

Example 115 was repeated except that isopropyl(methyl) amine was replaced with each corresponding amine, to provide the compounds of Examples 144-151.

Example 144

4-[(5-Chloro-2-pyridinyl)methoxy]-1-{4-[2-(methylamino)ethoxy]phenyl}-1H-pyridin-2-one $^1$HNMR(400 MHz,CDCl$_3$,δppm):2.52(3H,s),2.99(2H,t, J=5.1 Hz), 4.10(2H,t,J=5.1 Hz),5.15(2H,s),6.02(1H,d,J=2.7 Hz), 6.07(1H,dd,J=7.6,2.7 Hz),6.98(2H,d,J=9.0 Hz),7.23-

7.26(3H,m), 7.43(1H,dd,J=8.5,0.5 Hz),7.73(1H,dd,J=8.5,2.4 Hz), 8.58(1H,dd,J=2.4,0.5 Hz);

mass spectrum (ESI):386[M+H].

Example 145

4-[(5-Chloro-2-pyridinyl)methoxy]-1-{4-[2-(propylamino)ethoxy]phenyl}-1H-pyridin-2-one $^1$HNMR(400 MHz,CDCl$_3$,δppm):0.95(3H,t,J=7.3 Hz), 1.50-1.60(2H,m),2.65(2H,t,J=7.3 Hz),3.02(2H,t,J=5.2 Hz), 4.10(2H,t,J=5.2 Hz),5.15(2H,s),6.02(1H,d,J=2.7 Hz), 6.07 (1H,dd,J=7.6,2.7 Hz),6.98(2H,d,J=9.0 Hz),7.23-7.26(3H, m), 7.43(1H,d,J=8.3 Hz),7.73(1H,dd,J=8.3,2.4 Hz), 8.58 (1H,d,J=2.4 Hz);

mass spectrum (ESI):414[M+H].

Example 146

4-[(5-Chloro-2-pyridinyl)methoxy]-1-{4-[2-(isopropylamino)ethoxy]phenyl}-1H-pyridin-2-one $^1$HNMR(400 MHz,CDCl$_3$,δppm):1.11(6H,d,J=6.3 Hz), 2.85-2.92(1H,m),3.01(2H,t,J=5.2 Hz),4.10(2H,t,J=5.2 Hz), 5.15(2H,s),6.02(1H,d,J=2.7 Hz),6.07(1H,dd,J=7.6,2.7 Hz), 6.98(2H,d,J=9.0 Hz),7.23-7.26(3H,m),7.43(1H,dd,J=8.3,0.7 Hz), 7.73(1H,dd,J=8.3,2.4 Hz),8.58(1H,dd,J=2.4,0.7 Hz);

mass spectrum (ESI):414[M+H].

Example 147

4-[(5-Chloro-2-pyridinyl)methoxy]-1-(4-{2-[(2R)-2-butylamino)ethoxy]-phenyl}-1H-pyridin-2-one $^1$HNMR(400 MHz,CDCl$_3$,δppm):0.92(3H,t,J=7.4 Hz), 1.08(3H,d,J=6.3 Hz),1.30-1.42(1H,m),1.48-1.61(1H,m), 2.60-2.68(1H,m),2.95-3.07(2H,m),4.08-4.11(2H,m),5.15 (2H,s), 6.02(1H,d,J=2.8 Hz),6.07(1H,dd,J=7.7,2.8 Hz), 6.98 (2H,d,J=9.0 Hz),7.23-7.26(3H,m),7.43(1H,dd,J=8.5,0.5 Hz), 7.73(1H,dd,J=8.5,2.4 Hz),8.58(1H,dd,J=2.4,0.5 Hz);

mass spectrum (ESI):428[M+H].

Example 148

4-[(5-Chloro-2-pyridinyl)methoxy]-1-(4-{2-[(2S)-2-butylamino)ethoxy]-phenyl}-1H-pyridin-2-one $^1$HNMR(400 MHz,CDCl$_3$,δppm):0.92(3H,t,J=7.4 Hz), 1.08(3H,d,J=6.3 Hz),1.30-1.42(1H,m),1.48-1.61(1H,m), 2.60-2.68(1H,m),2.95-3.07(2H,m),4.08-4.11(2H,m),5.15 (2H,s), 6.02(1H,d,J=2.8 Hz),6.07(1H,dd,J=7.7,2.8 Hz), 6.98 (2H,d,J=9.0 Hz),7.23-7.26(3H,m),7.43(1H,dd,J=8.5,0.5 Hz), 7.73(1H,dd,J=8.5,2.4 Hz),8.58(1H,dd,J=2.4,0.5 Hz);

mass spectrum (ESI):428[M+H].

Example 149

1-{4-[2-(tert-butylamino)ethoxy]phenyl}-4-[(5-chloro-2-pyridinyl)methoxy]-1H-pyridin-2-one $^1$HNMR(400 MHz,CDCl$_3$,δppm):1.16(9H,s),2.98(2H,t, J=5.5 Hz), 4.10(2H,t,J=5.5 Hz),5.14(2H,s),6.01(1H,d,J=2.7 Hz), 6.07(1H,dd,J=7.7,2.7 Hz),6.98(2H,d,J=9.0 Hz),7.23-7.26(3H,m), 7.43(1H,dd,J=8.3,0.6 Hz),7.73(1H,dd,J=8.3,2.4 Hz), 8.58(1H,dd,J=2.4,0.6 Hz);

mass spectrum (ESI):428M+H].

Example 150

4-[(5-Chloro-2-pyridinyl)methoxy]-1-{4-[2-(cyclopropylamino)ethoxy]-phenyl}-1H-pyridin-2-one $^1$HNMR(400 MHz,CDCl$_3$,δppm):0.36-0.49(4H,m), 2.18-2.23(1H,m),3.10(2H,t,J=5.2 Hz),4.10(2H,t,J=5.2 Hz), 5.15 (2H,s),6.02(1H,d,J=2.7 Hz),6.07(1H,dd,J=7.6,2.7 Hz), 6.98 (2H,d,J=9.0 Hz),7.23-7.26(3H,m),7.43(1H,dd,J=8.4,0.5 Hz), 7.73(1H,dd,J=8.4,2.4 Hz),8.58(1H,dd,J=2.4,0.5 Hz);

mass spectrum (ESI):412[M+H].

Example 151

4-[(5-Chloro-2-pyridinyl)methoxy]-1-{4-[2-(cyclobutylamino)ethoxy]-phenyl}-1H-pyridin-2-one $^1$HNMR(400 MHz,CDCl$_3$,δppm):1.62-1.79(4H,m), 2.21-2.28(2H,m),2.95(2H,t,J=5.4 Hz),3.28-3.35(1H,m), 4.06(2H, t,J=5.4 Hz),5.15(2H,s),6.02(1H,d,J=2.7 Hz), 6.07(1H,dd, J=7.6,2.7 Hz),6.98(2H,d,J=8.8 Hz),7.23-7.26(3H,m), 7.43 (1H,d,J=8.3 Hz),7.73(1H,dd,J=8.3,2.4 Hz), 8.58(1H,d,J=2.4 Hz);

mass spectrum (ESI):426[M+H].

Example 152

4-[(5-Chloro-2-pyridinyl)methoxy]-1-{4-[2-(cyclopentylamino)ethoxy]-phenyl}-1H-pyridin-2-one $^1$HNMR(400 MHz,CDCl$_3$,δppm):1.32-141(2H,m), 1.52-1.62(2H,m),1.66-1.75(2H,m),1.84-1.93(2H,m), 3.01(2H,t, J=5.4 Hz),3.11-3.18(1H,m),4.10(2H,t,J=5.4 Hz), 5.15(2H,s), 6.02(1H,d,J=2.8 Hz),6.07(1H,dd,J=7.7,2.8 Hz), 6.98(2H,d, J=9.0 Hz),7.23-7.26(3H,m),7.43(1H,dd,J=8.3,0.7 Hz), 7.73 (1H,dd,J=8.3,2.4 Hz),8.58(1H,dd,J=2.4,0.7 Hz);

mass spectrum (ESI):440[M+H].

Examples 153-159

Step (1) of Example 109 was repeated except that dibromoethane was replaced with 1,3-dibromopropane, to provide 1-[4-(3-bromopropoxy)phenyl]-4-[(5-chloro-2-pyridinyl) methoxy]-1H-pyridin-2-one. Example 115 was then repeated except that the above product was used in place of 1-[4-(2-bromoethoxy)phenyl]-4-[(5-chloro-2-pyridinyl)methoxy]-1H-pyridin-2-one and isopropyl (methyl)amine was replaced with each compounding amine, to provide the compounds of Examples 153-159.

Example 153

4-[(5-Chloro-2-pyridinyl)methoxy]-1-{4-[3-(1-pyrrolidinyl)propoxy]phenyl)-1H-pyridin-2-one $^1$HNMR(400 MHz,CDCl$_3$,δppm):1.78-1.83(4H,m), 1.99-2.06(2H,m),2.52-2.57(4H,m),2.64(2H,t,J=7.5 Hz), 4.05(2H, t,J=6.3 Hz),5.14(2H,s),6.01(1H,d,J=2.7 Hz), 6.07(1H,dd, J=7.6,2.7 Hz),6.97(2H,d,J=9.0 Hz),7.22-7.25(3H,m), 743 (1H,dd,J=8.3,0.7 Hz),7.73(1H,dd,J=8.3,2.4 Hz), 8.58(1H, dd,J=2.4,0.7 Hz);

mass spectrum (ESI):440(M+H).

Example 154

4-[(5-Chloro-2-pyridinyl)methoxy]-1-{4-[3-(dimethylamino)propoxy]phenyl}-1H-pyridin-2-one $^1$HNMR(400 MHz,CDCl$_3$,δppm):1.93-2.00(2H,m),2.26(6H,s), 2.45(2H,t,J=7.1 Hz),4.04(2H,t,J=6.3 Hz),5.14(2H,s), 6.01(1H,d,J=2.7 Hz),6.07(1H,dd,J=7.6,2.7 Hz), 6.97(2H,d,J=9.0 Hz),7.22-7.25(3H,m),7.43(1H,d,J=8.5 Hz), 7.73(1H,dd,J=8.5,2.4 Hz),8.58(1H,d,J=2.4 Hz);

mass spectrum (ESI):414(M+H).

Example 155

4-[(5-Chloro-2-pyridinyl)methoxy]-1-{4-[3-(diethylamino)propoxy]phenyl}-1H-pyridin-2-one $^1$HNMR(400 MHz,CDCl$_3$,δppm):1.04(6H,t,J=7.1 Hz), 1.91-1.98(2H,m),2.56(4H,q,J=7.1 Hz),2.62(2H,t,J=7.1 Hz), 4.03(2H,t,J=6.2 Hz),5.14(2H,s),6.01(1H,d,J=2.7 Hz), 6.07 (1H,dd,J=7.6,2.7 Hz),6.97(2H,d,J=9.0 Hz),7.22-7.25(3H,m), 7.43(1H,dd,J=8.3,0.7 Hz),7.73(1H,dd,J=8.3,2.4 Hz), 8.58(1H,dd,J=2.4,0.7 Hz);

mass spectrum (ESI):442(M+H).

Example 156

4-[(5-Chloro-2-pyridinyl)methoxy]-1-(4-{3-[ethyl(methyl)amino]propoxy}-phenyl-1H-pyridin-2-one $^1$HNMR(400 MHz,CDCl$_3$,δppm):1.07(3H,t,J=7.1 Hz), 1.93-2.01(2H,m),226(3H,s),2.45(2H,q,J=7.1 Hz), 2.53(2H,t,J=7.1 Hz),4.04(2H,t,J=6.3 Hz),5.14(2H,s), 6.01(1H,d,J=2.7 Hz),6.07(1H,dd,J=7.6,2.7 Hz), 6.97(2H,d,J=9.0 Hz),7.22-7.25(3H,m),7.43(1H,d,J=8.3 Hz), 7.73(1H,dd,J=8.3,2.4 Hz), 8.58(1H,d,J=2.4 Hz);

mass spectrum (ESI):428(M+H).

Example 157

4-[(5-Chloro-2-pyridinyl)methoxy]-1-(4-{3-[isopropyl(methyl)amino]-propoxy}phenyl)-1H-pyridin-2-one $^1$HNMR(400 MHz,CDCl$_3$,δppm):1.01(6H,d,J=6.6 Hz), 1.90-1.98(2H,m),2.24(3H,s),2.52-2.58(2H,m),2.81-2.88(1H,m), 4.04(2H,t,J=6.2 Hz),5.14(2H,s),6.01(1H,d,J=2.7 Hz), 6.07(1H,dd,J=7.6,2.7 Hz),6.97(2H,d,J=9.0 Hz),7.22-7.25(3H,m), 7.43(1H,d,J=8.5 Hz),7.73(1H,dd,J=8.5,2.4 Hz), 8.58(1H,d,J=2.4 Hz);

mass spectrum (ESI):442(M+H).

Example 158

4-[(5-Chloro-2-pyridinyl)methoxy]-1-(4-{3-[methyl(propyl)amino]-propoxy}phenyl)-1H-pyridin-2-one $^1$HNMR(400 MHz,CDCl$_3$,δppm):0.90(3H,t,J=7.4 Hz), 1.45-1.54(2H,m),1.93-2.00(2H,m),2.25(3H,s), 2.32(2H,t,J=7.4 Hz),2.52(2H,t,J=7.1 Hz),4.04(2H,t,J=6.3 Hz), 5.14 (2H,s),6.01(1H,d,J=2.7 Hz),6.07(1H,dd,J=7.7,2.7 Hz), 6.97 (2H,d,J=9.0 Hz),7.22-7.25(3H,m),7.43(1H,dd,J=8.3,0.7 Hz), 7.73(1H,dd,J=8.3,2.4 Hz),8.58(1H,dd,J=2.4,0.7 Hz);

mass spectrum (ESI):442(M+H).

Example 159

4-[(5-Chloro-2-pyridinyl)methoxyl]-1-{4-[3-(ethylamino)propoxy]phenyl}-1H-pyridin-2-one $^1$HNMR(400 MHz,CDCl$_3$,δppm):1.13(3H,t,J=7.2 Hz), 1.47(1H,brs),1.96-2.02(2H,m),2.68(2H,q,J=7.2 Hz), 2.81(2H,t,J=7.0 Hz),4.07(2H,t,J=6.2 Hz),5.14(2H,s), 6.02(1H,d,J=2.7 Hz),6.07(1H,dd,J=7.6,2.7 Hz), 6.97(2H,d,J=9.0 Hz), 7.22-7.26(3H,m),7.43(1H,d,J=8.3 Hz), 7.73(1H,dd,J=8.3,2.4 Hz),8.58(1H,d,J=2.4 Hz);

mass spectrum (ESI):414(M+H).

Example 160

4-(4-Fluorobenzyloxy)-1-{2-methoxy-4-[2-(1-pyrrolidinyl)ethoxy]phenyl}-1H-pyridin-2-one Example 12 was repeated except that 4-benzyloxy-1H-pyridin-2-one and 2-[(4-iodophenyl)oxy]tetrahydropyran were replaced with 4-fluorobenzyloxy)-1H-pyridin-2-one and 2-[(4-iodo-3-methoxyphenyl)oxy]-tetrahydropyran, to provide the compound of Example 160.

$^1$HNMR(300 MHz,CDCl$_3$,δppm):1.78-1.95(4H,m), 2.67-2.84(4H,m),3.00(2H,t,J=5.8 Hz),3.78(3H,s), 4.19(2H,t,J=5.8 Hz),4.98(2H,s),5.98(1H,dd,J=7.6,2.7 Hz), 6.05(1H,d,J=2.7 Hz),6.55(1H,dd,J=8.6,2.5 Hz), 6.62(1H,d,J=2.5 Hz), 7.02-7.19(4H,m),7.40(2H,dd,J=8.6,5.3 Hz);

mass spectrum (ESI):439(M+H).

Formulation Example 1

Twenty (20.0) g of Example 1 compound, 417 g of lactose, 80 g of crystalline cellulose and 80 g of partially alphatized starch were mixed in a V-shaped mixer, and thereafter 3.0 g of magnesium stearate was added and mixed. The mixed powder was tabletted according to accepted practice to provide 3000 tablets of 7.0 mm in diameter and 150 mg in weight per tablet.

| Ingredients' contents per tablet (150 mg) | |
|---|---|
| compound of Example 1 | 5.0 mg |
| lactose | 104.25 mg |
| crystalline cellulose | 20.0 mg |
| partially alphatized starch | 20.0 mg |
| magnesium stearate | 0.75 mg |

Formulation Example 2

Dissolving 10.8 g of Hydroxypropyl Cellulose 2910 and 2.1 g of Polyethylene Glycol 6000 in 172.5 g of purified water, 2.1 g of titanium dioxide was dispersed in the solution to provide a coating liquid. The coating liquid was spray-coated on separately prepared 2500 tablets of Formulation Example 1 with High-Coater Mini, to provide film-coated tablets weighing 155 mg per tablet.

| Ingredients' contents per tablet (155 mg) | |
|---|---|
| tablet of Formulation Example 1 | 150 mg |
| Hydroxypropyl Cellulose 2910 | 3.6 mg |

-continued

| Ingredients' contents per tablet (155 mg) | |
|---|---|
| Polyethylene Glycol 6000 | 0.7 mg |
| titanium dioxide | 0.7 mg |

The invention claimed is:

1. A compound of formula (I):

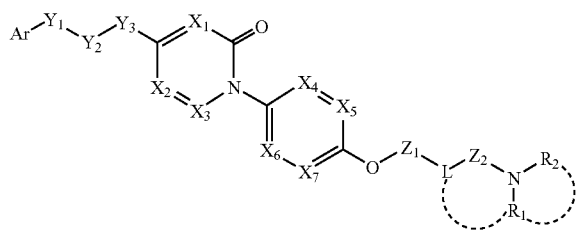

(I)

wherein:
- $R_1$ and $R_2$ are the same or different and are each independently selected from: hydrogen, optionally substituted lower alkyl, optionally substituted lower cycloalkyl, optionally substituted lower alkylcarbonyl, optionally substituted lower alkyloxycarbonyl and optionally substituted lower alkylsulfonyl; or $R_1$ and $R_2$ form an optionally substituted aliphatic nitrogen-containing heterocyclic group together with the nitrogen atom to which they bind;
- $X_1$, $X_2$ and $X_3$ are the same or different and are each independently selected from: unsubstituted methine and nitrogen atom, provided not all of $X_1$, $X_2$ and $X_3$ simultaneously stand for nitrogen;
- $X_4$, $X_5$, $X_6$ and $X_7$ are the same or different and are each independently selected from: optionally substituted methine and nitrogen, provided that three or more of $X_4$, $X_5$, $X_6$ and $X_7$ are not simultaneously nitrogen;
- $Y_1$ is selected from: a single bond, —O—, —NR—, —S—, —SO—, and —SO$_2$—;
- $Y_2$ is selected from: optionally substituted lower alkylene, optionally substituted lower alkenylene, and optionally substituted lower cycloalkylene;
- $Y_3$ is selected from: a single bond, —O—, —NR—, —S—, —SO—, and —SO$_2$—;
- R is selected from: hydrogen and optionally substituted lower alkyl;
- L is optionally substituted methylene;
- $Z_1$ and $Z_2$ are the same or different and are each independently selected from: a single bond and optionally substituted lower alkylene; or
- $R_1$, L and $Z_2$ together form an optionally substituted aliphatic nitrogen-containing heterocyclic group with the nitrogen to which $R_1$ binds; and
- Ar stands for an optionally substituted aromatic carbocyclic group, optionally substituted heteroaromatic group or optionally substituted aliphatic carbocyclic group;

or a pharmaceutically acceptable salt thereof.

2. The compound according to claim 1, wherein one of $X_1$, $X_2$ and $X_3$ is a nitrogen atom and the other two are unsubstituted methine groups; or a pharmaceutically acceptable salt thereof.

3. The compound according to claim 1, wherein $X_4$, $X_5$, $X_6$ and $X_7$ are each optionally substituted methine groups; or a pharmaceutically acceptable salt thereof.

4. The compound according to claim 1, wherein $Y_1$ is selected from a single bond and —O—; or a pharmaceutically acceptable salt thereof.

5. The compound according to claim 1, wherein $Y_2$ is selected from optionally substituted methylene, optionally substituted ethylene, and optionally substituted vinylene; or a pharmaceutically acceptable salt thereof.

6. The compound according to claim 1, wherein $Y_3$ is selected from a single bond and —O—; or a pharmaceutically acceptable salt thereof.

7. The compound according to claim 1, wherein $Z_1$ is selected from a single bond or optionally substituted methylene; or a pharmaceutically acceptable salt thereof.

8. The compound according to claim 7, wherein L is optionally substituted methylene; or a pharmaceutically acceptable salt thereof.

9. The compound according to claim 7, wherein $Z_2$ is selected from a single bond and optionally substituted methylene; or a pharmaceutically acceptable salt thereof.

10. The compound according to claim 1, wherein $R_1$, L, and $Z_2$, together with the nitrogen to which $R_1$ binds, form an optionally substituted pyrrolidine ring or an optionally substituted piperidine ring; or a pharmaceutically acceptable salt thereof.

11. The compound according to claim 10, wherein $R_2$ is selected from: hydrogen, optionally substituted $C_1$-$C_4$ alkyl, and optionally substituted $C_3$-$C_5$ cycloalkyl; or a pharmaceutically acceptable salt thereof.

12. The compound according to claim 1, wherein $R_1$ and $R_2$ are each independently selected from hydrogen, optionally substituted $C_1$-$C_4$ alkyl, and optionally substituted $C_3$-$C_5$ cycloalkyl; or a pharmaceutically acceptable salt thereof.

13. The compound according to claim 1, wherein $R_1$ and $R_2$, together with the nitrogen atom to which they bind, form an optionally substituted pyrrolidine ring or an optionally substituted piperidine ring; or a pharmaceutically acceptable salt thereof.

14. The compound according to claim 1, in which Ar is selected from optionally substituted phenyl and optionally substituted pyridinyl; or a pharmaceutically acceptable salt thereof.

15. The compound according to claim 14, wherein the optional Ar substituent is selected from the group consisting of fluorine, chlorine, methyl, ethyl, hydroxyl, methoxy, ethoxy, trifluoromethyl, difluoromethoxy and trifluoromethoxy, or a pharmaceutically acceptable salt thereof.

16. The compound according to claim 2, wherein:
- $X_4$, $X_5$, $X_6$ and $X_7$ are each optionally substituted methine groups,
- $Y_1$ is selected from a single bond and —O—,
- $Y_2$ is selected from optionally substituted methylene, optionally substituted ethylene, and optionally substituted vinylene,
- $Y_3$ is selected from a single bond and —O—,
- $Z_1$ is selected from a single bond and optionally substituted methylene,
- L is optionally substituted methylene,
- $Z_2$ is selected from a single bond and optionally substituted methylene,
- $R_1$ and $R_2$ are each independently selected from hydrogen, optionally substituted $C_1$-$C_4$ alkyl, and optionally substituted $C_3$-$C_5$ cycloalkyl, and
- Ar is selected from an optionally substituted phenyl and an optionally substituted pyridinyl, wherein the optional Ar substituent is selected from the group consisting of fluorine, chlorine, methyl, ethyl, hydroxyl, methoxy, ethoxy, trifluoromethyl, difluoromethoxy, and trifluoromethoxy;

or a pharmaceutically acceptable salt thereof.

17. The compound according to claim 2, wherein:

$X_4$, $X_5$, $X_6$ and $X_7$ are each optionally substituted methine groups, $Y_1$ is selected from a single bond and —O—, $Y_2$ is selected from optionally substituted methylene, optionally substituted ethylene, and optionally substituted vinylene, $Y_3$ is selected from a single bond and —O—, $Z_1$ is selected from a single bond, and optionally substituted methylene, $R_1$, L, and $Z_2$, together with the nitrogen to which $R_1$ binds, form an optionally substituted pyrrolidine ring or an optionally substituted piperidine ring, $R_2$ is selected from hydrogen, optionally substituted $C_1$-$C_4$ alkyl, and optionally substituted $C_3$-$C_5$ cycloalkyl, and Ar is selected from an optionally substituted phenyl, and an optionally substituted pyridinyl, wherein the optional Ar substituent is selected from the group consisting of fluorine, chlorine, methyl, ethyl, hydroxyl, methoxy, ethoxy, trifluoromethyl, difluoromethoxy and trifluoromethoxy;

or a pharmaceutically acceptable salt thereof.

18. The compound according to claim 2, wherein:

$X_4$, $X_5$, $X_6$ and $X_7$ are each optionally substituted methine groups, $Y_1$ is selected from a single bond and —O—, $Y_2$ is selected from optionally substituted methylene, optionally substituted ethylene, and optionally substituted vinylene, $Y_3$ is selected from a single bond and —O—, $Z_1$ is selected from a single bond and optionally substituted methylene, L is optionally substituted methylene, $Z_2$ is selected from a single bond and optionally substituted methylene, $R_1$ and $R_2$ together with the nitrogen atom to which they bind, form an optionally substituted pyrrolidine ring or an optionally substituted piperidine ring, and Ar is selected from optionally substituted phenyl, and optionally substituted pyridinyl, wherein the optional Ar substituent is selected from the group consisting of fluorine, chlorine, methyl, ethyl, hydroxyl, methoxy, ethoxy, trifluoromethyl, difluoromethoxy, and trifluoromethoxy;

or a pharmaceutically acceptable salt thereof.

19. A compound according to claim 1, selected from the group consisting of:

4-benzyloxy-1-{4-[2-(dimethylamino)ethoxy]phenyl}-1H-pyridin-2-one, 4-benzyloxy-1-{4-[2-(diethylamino)ethoxy]phenyl}-1H-pyridin-2-one, 1-{4-[2-(diethylamino)ethoxy]phenyl}-4-(4-fluorobenzyloxy)-1H-pyridin-2-one, 4-(4-fluorobenzyloxy)-1-{4-[2-(diethylamino)ethoxy]phenyl}-1H-pyrimidin-2-one, 4-[(5-chloro-2-pyridinyl)methoxy]-1-{4-[2-(dimethylamino)ethoxy]phenyl}-1H-pyridin-2-one, 4-[(5-chloro-2-pyridinyl)methoxy]-1-{4-[2-(diethylamino)ethoxy]phenyl}-1H-pyridin-2-one, 4-[(5-chloro-2-pyridinyl)methoxy]-1-(4-{2-[ethyl(methyl)amino]ethoxy}-phenyl)-1H-pyridin-2-one, 4-[(5-chloro-2-pyridinyl)methoxy]-1-(4-{2-[isopropyl(methyl)amino]-ethoxy}phenyl)-1H-pyridin-2-one, 4-(4-fluorobenzyloxy)-1-(4-{2-[isopropyl(methyl)amino]ethoxy}phenyl)-1H-pyridin-2-one, 4-[(5-chloro-2-pyridinyl)methoxy]-1-{4-[2-(isopropylamino)ethoxy]phenyl}-1H-pyridin-2-one, 4-[(5-chloro-2-pyridinyl)methoxy]-1-(4-{2-[(2R)-2-butylamino]ethoxy}-phenyl)-1H-pyridin-2-one, 4-[(5-chloro-2-pyridinyl)methoxy]-1-(4-{2-[(2S)-2-butylamino]ethoxy}-phenyl)-1H-pyridin-2-one, and 4-[(5-chloro-2-pyridinyl)methoxy]-1-{4-[2-(cyclopentylamino)ethoxy]phenyl}-1H-pyridin-2-one, or a pharmaceutically acceptable salt thereof.

20. A compound according to claim 1, selected from the group consisting of:

4-benzyloxy-1-(4-{[(2S)-1-methyl-2-pyrrolidinyl]methoxy}phenyl)-1H-pyridin-2-one, 4-[(5-chloro-2-pyridinyl)methoxy]-1-{4-[(2R)-2-(diethylamino)propoxy]-phenyl}-1H-pyridin-2-one, 4-[(5-chloro-2-pyridinyl)methoxy]-1-{4-[(2S)-2-(diethylamino)propoxy]-phenyl}-1H-pyridin-2-one, 4-[(5-chloro-2-pyridinyl)methoxy]-1-(4-{[(2S)-1-isopropyl-2-pyrrolidinyl]-methoxy}phenyl-1H-pyridin-2-one, 4-[(5-chloro-2-pyridinyl)methoxy]-1-(4-{[(2S)-1-methyl-2-pyrrolidinyl]-methoxy}phenyl)-1H-pyridin-2-one, 4-[(5-chloro-2-pyridinyl)methoxy]-1-(4-{[(2S)-1-ethyl-2-pyrrolidinyl]-methoxy}phenyl)-1H-pyridin-2-one, 4-[(5-chloro-2-pyridinyl)methoxy]-1-{4-[(2R)-2-(dimethylamino)propoxy]-phenyl}-1H-pyridin-2-one, 4-[(5-chloro-2-pyridinyl)methoxy]-1-{4-[(2S)-2-(dimethylamino)propoxy]-phenyl}-1H-pyridin-2-one, 4-[(5-chloro-2-pyridinyl)methoxy]-1-{4-[(2R)-2-(1-pyrrolidinyl)propoxy]-phenyl}-1H-pyridin-2-one, and 4-[(5-chloro-2-pyridinyl)methoxy]-1-{4-[(2S)-2-(1-pyrrolidinyl)-propoxy]phenyl}-1H-pyridin-2-one, or a pharmaceutically acceptable salt thereof.

21. A compound according to claim 1, selected from the group consisting of:

4-benzyloxy-1-{4-[2-(1-pyrrolidinyl)ethoxy]phenyl}-1H-pyridin-2-one, 4-(4-fluorobenzyloxy)-1-{4-[2-(1-pyrrolidinyl)ethoxy]phenyl}-1H-pyridin-2-one, 4-[(5-chloro-2-pyridinyl)methoxy]-1-{4-[2-(1-pyrrolidinyl)ethoxy]phenyl}-1H-pyridin-2-one, 4-[(E)-2-(4-fluorophenyl)vinyl]-1-{4-[2-(1-pyrrolidinyl)ethoxy]phenyl}-1H-pyridin-2-one, 4-[(E)-2-phenylvinyl]-1-{4-[2-(1-pyrrolidinyl)ethoxy]phenyl}-1H-pyridin-2-one, 4-(4-chlorobenzyloxy)-1-{4-[2-(1-pyrrolidinyl)ethoxy]phenyl}-1H-pyridin-2-one, 4-(4-fluorobenzyloxy)-1-{4-[2-(1-pyrrolidinyl)ethoxy]phenyl}-1H-pyrimidin-2-one, 4-[(5-chloro-2-pyridinyl)methoxy]-1-(4-{[(3R)-1-isopropyl-3-pyrrolidinyl]-oxy}phenyl)-1H-pyridin-2-one, 4-[(5-chloro-2-pyridinyl)methoxy]-1-(4-{[(3R)-1-ethyl-3-pyrrolidinyl]oxy}-phenyl)-1H-pyridin-2-one, and 4-[(5-chloro-2-pyridinyl)methoxy]-1-(4-{[(3R)-1-methyl-3-pyrrolidinyl]-oxy}phenyl)-1H-pyridin-2-one, or a pharmaceutically acceptable salt thereof.

22. A composition comprising a compound according to claim 1, and a pharmaceutically acceptable carrier.

23. A method of preventing or treating obesity in a subject in need of such prevention or treatment comprising administration of prophylactically or therapeutically effective amount of a compound according to claim 1.

* * * * *